United States Patent
Ebneth et al.

(10) Patent No.: US 11,453,881 B2
(45) Date of Patent: Sep. 27, 2022

(54) MODIFIED OLIGONUCLEOTIDES FOR USE IN TREATMENT OF TAUOPATHIES

(71) Applicant: Janssen Pharmaceutica NV, Beerse (BE)

(72) Inventors: Andreas Ebneth, Turnhout (BE); Constantin Van Outryve D'Ydewalle, Herent (BE); Sergei Gryaznov, San Mateo, CA (US); Saúl Martinez Montero, San Bruno, CA (US); Leonid Beigelman, San Mateo, CA (US); Vivek Kumar Rajwanshi, Cupertino, CA (US)

(73) Assignee: Janssen Pharmaceutica NV, Beerse (BE)

( * ) Notice: Subject to any disclaimer, the term of this patent is extended or adjusted under 35 U.S.C. 154(b) by 67 days.

(21) Appl. No.: 16/980,389

(22) PCT Filed: Mar. 13, 2019

(86) PCT No.: PCT/EP2019/056312
§ 371 (c)(1),
(2) Date: Sep. 12, 2020

(87) PCT Pub. No.: WO2019/175260
PCT Pub. Date: Sep. 19, 2019

(65) Prior Publication Data
US 2021/0095284 A1    Apr. 1, 2021

Related U.S. Application Data

(60) Provisional application No. 62/642,499, filed on Mar. 13, 2018.

(51) Int. Cl.
*C12N 15/113*   (2010.01)
*A61P 25/28*    (2006.01)

(52) U.S. Cl.
CPC ............ *C12N 15/113* (2013.01); *A61P 25/28* (2018.01); *C12N 2310/11* (2013.01); *C12N 2310/315* (2013.01); *C12N 2310/321* (2013.01); *C12N 2310/3341* (2013.01); *C12N 2310/346* (2013.01); *C12N 2320/50* (2013.01)

(58) Field of Classification Search
None
See application file for complete search history.

(56) References Cited

U.S. PATENT DOCUMENTS

2014/0121261 A1    5/2014    Gryaznov et al.

FOREIGN PATENT DOCUMENTS

| WO | 2001018015 A1 | 3/2001 |
|----|---------------|--------|
| WO | 2007107789 A3 | 5/2008 |
| WO | 2014153236 A1 | 9/2014 |
| WO | 2015010135 A3 | 4/2015 |
| WO | 2016126995 A1 | 8/2016 |
| WO | 2017109679 A1 | 6/2017 |

OTHER PUBLICATIONS

Conay, L., et al., "The synthesis, conformation and hydrolytic stability of an N,S-bridging thiophosphoramidate analogue of thymidylyl-3',5'-thymidine", Organic & Biomolucular chemistry, Jan. 1, 2016, pp. 7361-7367, vol. 14 (30).
Pongracz K., et al, Novel short Oligonucleotide Conjugates as Inhibitors of Human Telomerase, Nucleosides, Nucleotides and Nucleic acids., Oct. 1, 2003, pp. 1627-1629, vol. 22 (5-8).
Schultz ,R., et al, "Oligo-2'-fluoro-2'-deoxynucleotide N3", Nucleic Acids Research, Aug. 1, 1996, pp. 2966-2973, vol. 24(15).
International Search Report & Written Opinion dated Oct. 16, 2019 for PCT Patent Applicantion No. PCT/EP2019/056312.
Chen, et al., Synthesis of Oligodeoxyribonucelotide N3'-P5', Nucleic Acids Research, vol. 23 (14); pp. 2661-2668 (1995).
Devos, S. L., et al., "Tau reduction prevents neuronal loss and reverses pathological tau deposition and seeding in mice with tauopathy", Sci. Transl. Med., vol. 9; pp. 1-14 (eaag0481), (Jan. 25, 2017).
Morris, et al., "The Many Faces of Tau, Neuron" vol. 70; pp. 410-426 (May 2011).
Wischik, et al., "Structural characterization of the core of the paired helical filament of Alzheimer disease", Proc. Natl. Acad. Sci. USA, vol. 85; pp. 4884-4888 (Jul. 1988).

*Primary Examiner* — Tracy Vivlemore

(57) ABSTRACT

Oligonucleotides comprising modifications at the 2' and/or 3' positions(s) along with methods of making and use against Alzheimer disease and other tauopathies are disclosed.

32 Claims, No Drawings

Specification includes a Sequence Listing.

MODIFIED OLIGONUCLEOTIDES FOR USE IN TREATMENT OF TAUOPATHIES

BACKGROUND

Antisense oligonucleotide therapies have been considered for treatment or prevention of various diseases and conditions such as viral diseases, neurological diseases, neurodegenerative diseases, fibrotic diseases and hyperproliferative diseases.

Neurodegenerative diseases associated with the pathological aggregation of tau protein in neurofibrillary or gliofibrillary tangles in the human brain are known as tauopathies. Tangles are composed of hyperphosphorylated microtubule-associated protein tau, aggregated in an insoluble form. Neurofibrillary tangles (NFT) may lead to neuronal death and therefore be a primary causative factor in tauopathies, including Alzheimer's disease.

Alzheimer's disease (AD) is a chronic neurodegenerative brain disorder and accounts for 50-70% of all cases of dementia. Approximately 47 million people worldwide live with dementia and the number is expected to rise to 131 million by 2050. Only symptomatic treatments are available illustrating the necessity to find disease-modifying therapies which slow or even halt disease progression.

Pathologically, AD is characterized by the abnormal accumulation of extracellular amyloid β plaques and the intracellular formation of NFTs consisting of hyperphosphorylated tau proteins. tau is a microtubule-associated protein (MAP) encoded by the MAPT gene. The location and intensity of NFT accumulation strongly correlate with cognitive decline in AD, and mutations in the MAPT gene cause frontotemporal dementia with Parkinsonism (FTD). These facts support the development of tau-based therapies. Reducing aggregation, removing intracellular aggregates, stopping spreading, increasing intracellular clearance and altering post-translational modifications are some therapeutic strategies aiming to reduce tau pathology.

Antisense oligonucleotides (ASOs) are small single-stranded nucleic acid molecules that bind to their RNA targets through classical Watson-Crick basepairing resulting in an ASO:RNA duplex. Depending on the chemical modifications of the phosphate-sugar backbone, the formed ASO: RNA duplex can recruit RNase-H that will cleave the RNA strand of the duplex leaving the ASO intact. The cleaved RNA is then further degraded resulting in reduced mRNA and protein expression levels of the target gene. The chemical modifications of the ASO backbone can also change the binding affinity, resistance to nuclease activity and binding capacity to (serum) proteins.

Accordingly, there is a need in the art to discover and develop new therapies with different mechanisms of action, increased potency, increased affinity and/or decreased side-effects.

SUMMARY

The present disclosure relates to compounds and compositions containing oligonucleotides and their use in preventing or treating diseases and conditions, e.g., tauopathies such as Alzheimer's disease.

Some embodiments include an oligonucleotide comprising a sequence complementary to at least a portion of the MAPT gene sequence where one or more nucleotides of the oligonucleotide are nucleotides of Formula (I):

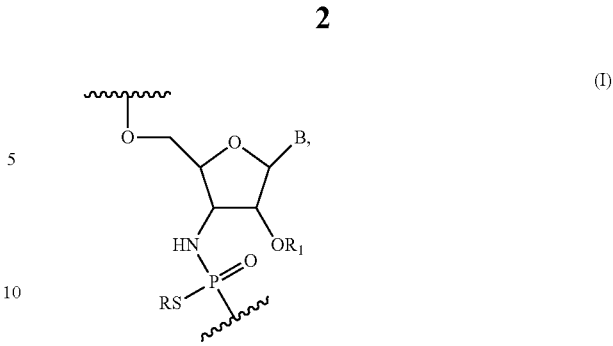

wherein R is H or a positively charged counter ion, B is a nucleobase, $R_1$ is $-(CR'_2)_2OCR'_3$, and R' is independently in each instance H or F. In some embodiments, each nucleotide of said oligonucleotide is a nucleotide of Formula (I). In some embodiments, the oligonucleotide comprises 2 to 40 nucleotides. In some embodiments, the oligonucleotide comprises 2-26 nucleotides of Formula (I). In some embodiments, the oligonucleotide comprises 5-10 nucleotides of Formula (I). In some embodiments, B is an unmodified nucleobase in at least one nucleotide of Formula (I). In some embodiments, B is a modified nucleobase in at least one nucleotide of Formula (I). In some embodiments, B is an unmodified nucleobase in each nucleotide of Formula (I). In some embodiments, B is a modified nucleobase in each nucleotide of Formula (I). In some embodiments, each R' is H in at least one nucleotide of Formula (I). In some embodiments, each R' is H in each nucleotide of Formula (I). In some embodiments, $R_1$ is $-(CH_2)_2OCH_3$ in at least one nucleotide of Formula (I). In some embodiments, $R_1$ is $-(CH_2)_2OCH_3$ in each nucleotide of Formula (I).

In some embodiments, the oligonucleotide comprises one or more nucleotides of Formula (II):

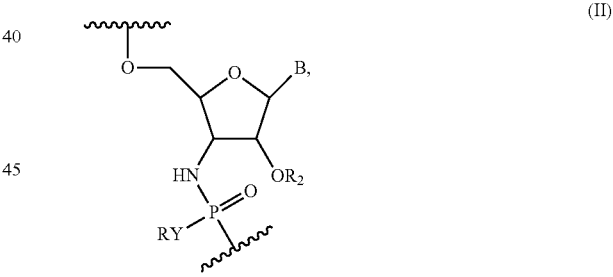

wherein Y is S or O, R is H or a positively charged counter ion, B is a nucleobase, $R_2$ is $-CR'_3$, $-CR'_2OCR'_3$, $-(CR'_2)_3OCR'_3$ or $-(CR'_2)_{1-2}CR'_3$, or $R_2$ is $-(CR'_2)_2OCR'_3$ and Y is O, and R' is independently in each instance H or F. In some embodiments, the oligonucleotide comprises at least one nucleotide of Formula (II), where $R_2$ is $-CR'_3$. In some embodiments, the oligonucleotide comprises at least one nucleotide of Formula (II), where $R_2$ is $-(CR'_2)_{1-20}CR'_3$. In some embodiments, the oligonucleotide comprises at least one nucleotide of Formula (II), where $R_2$ is $-(CR'_2)_{1-2}CR'_3$. In some embodiments, B is a modified nucleobase in at least one nucleotide of Formula (II). In some embodiments, Y is S in at least one nucleotide of Formula (II). In some embodiments, Y is O in at least one nucleotide of Formula (II). In some embodiments, Y is S in each nucleotide of Formula (II). In some embodiments, Y is O in each nucleotide of Formula (II).

In some embodiments, the oligonucleotide further comprises one or more nucleotides of Formula (IIIa) or Formula (IIIb):

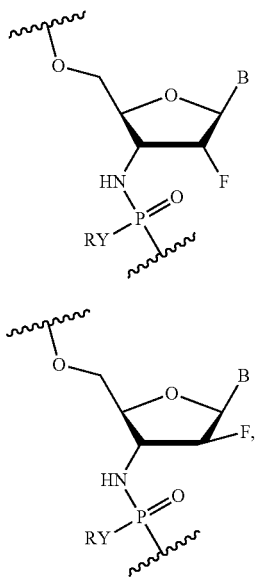

(IIIa)

(IIIb)

wherein Y is S or O, R is H or a positively charged counter ion, and B is a nucleobase.

In some embodiments, the oligonucleotide further comprises one or more nucleotides of Formula (V'):

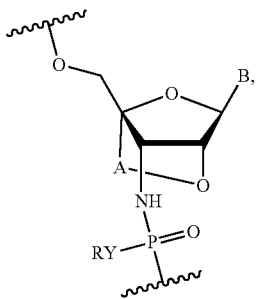

(V')

wherein Y is S or O, R is H or a positively charged counter ion, B is independently in each instance a natural or an unmodified nucleobase or a modified nucleobase, A is —(CR"R")$_{1-2}$— and R" is independently in each instance H, F or Me.

In some embodiments, the oligonucleotide is arranged in a construct of Formula (VI): 5' X-Y-Z 3' (VI), wherein each of X, Y and Z is a domain comprising 2-14 nucleotides, at least one of the X and Z domains comprising at least one nucleotide of Formula (I), and wherein each of the nucleotides of the Y domain is a 2'-deoxynucleotide. In some embodiments, the oligonucleotide comprises 18 to 22 nucleosides. In some embodiments, the X and Z domains each comprise 5-10 nucleotides. In some embodiments, the Y domain comprises 5-10 nucleotides. In some embodiments, the X and Z domains each comprise 5-10 nucleotides, and the Y domain comprises 5-10 nucleotides. In some embodiments, the X and Z domains each comprise 5 nucleotides, and the Y domain comprises 10 nucleotides. In some embodiments, each nucleotide of the X and Z domains is a nucleotide of Formula (I). In some embodiments, at least one nucleotide of the X domain and at least one nucleotide of the Z domain are each independently selected from the group consisting of a nucleotide of Formula (II), a nucleotide of Formula (IIIa), and a nucleotide of Formula (IIIb). In some embodiments, each of the at least one nucleotide of the X and Z domains are the same nucleotide. In some embodiments, each nucleotide of the Y domain is linked through thiophosphate intersubunit linkages. In some embodiments, the oligonucleotide is single stranded. In some embodiments, the oligonucleotide is an antisense oligonucleotide.

In embodiments, the oligonucleotide is complementary to at least a portion of exon 5 of the human MAPT gene.

Other embodiments include a chimeric oligonucleotide comprising a sequence complementary to at least a portion of the MAPT gene sequence where one or more nucleotides of the oligonucleotide are nucleotides of Formula (VI):

$$5'\text{-X-Y Z-}3' \qquad (VI),$$

wherein X-Y-Z is a chimeric oligonucleotide comprising a sequence of 18 to 22 nucleosides, and is optionally conjugated at the 5' and/or 3' end to a ligand targeting group; X is a domain comprising a sequence of modified nucleosides that is 3-10 nucleosides in length; Z is a domain comprising a sequence of modified nucleosides that is 3-10 nucleosides in length; and Y is a domain comprising a sequence of 2 to 14 2'-deoxy-nucleosides linked through thiophosphate intersubunit linkages. In some embodiments, the Y domain is 6 to 10 nucleosides in length. In some embodiments, X and/or Z domains comprise a sequence of modified nucleosides linked through N3'→P5' phosphoramidate or N3'→P5' thiophosphoramidate intersubunit linkages. In some embodiments, the Y domain comprises at least one phosphodiester intersubunit linkage. In some embodiments, the Y domain consists of 2'-deoxy-nucleosides linked through thiophosphate intersubunit linkages, and optionally one or two phosphodiester intersubunit linkage. In some embodiments, the X domain comprises modified nucleosides where the modification is independently selected from the group consisting of 2'-F, 2'-F—N3'→P5', 2'-OMe, 2'-OMe-N3'→P5', 2'-O-methoxyethoxy, 2'-O-methoxyethoxy-N3'→P5', conformationally restricted nucleosides, 2'-OH—N3'→P5' thiophosphoramidate and 2'-OH—N3'→P5' phosphoramidate. In some embodiments, the functional domain of Z comprises modified nucleosides where the modification is selected from the group consisting of 2'-F, 2'-F—N3'→P5', 2'-OMe, 2'-OMe-N3'→P5', 2'-O-methoxyethoxy, 2'-O-methoxyethoxy-N3'→P5', conformationally restricted nucleosides, 2'-OH—N3'→P5' thiophosphoramidate and 2'-OH—N3'→P5' phosphoramidate. In some embodiments, the X and/or Z domains comprise one or more 2'-deoxy-nucleosides linked through a N3'→P5' phosphoramidate intersubunit linkage. In some embodiments, the X and Z domains comprise one or more 2'-arabino-F and/or 2'-ribo-F modified nucleoside, wherein each said nucleoside is independently linked through at least one of an N3'→P5' phosphoramidate or N3'→P5' thiophosphoramidate intersubunit linkage. In some embodiments, the X and Z domains comprise one or more 2'-OMe modified nucleosides, wherein each said nucleoside is independently linked through at least one of N3'→P5' phosphoramidate, N3'→P5' thiophosphoramidate, or thiophosphate intersubunit linkages. In some embodiments, the modified nucleosides in each of the X and Z domains are 2'-OMe modified nucleosides linked through thiophosphate intersubunit linkages, and wherein the modified nucleosides include 5-methylcytosine nucleobases, but optionally not cytosine. In some embodiments, the modified nucleosides include 2,6-diaminopurine nucleobases, but optionally not adenine. In some embodiments, the modified nucleosides include 5-methyluracil nucleobases, but optionally not uracil. In some embodiments, the modified nucleosides include 2,6-diaminopurine nucleobases, but not adenine and 5-methyluracil nucleobases, but optionally not uracil. In some embodiments, the Y domain comprises 6-8 2'-deoxy-nucleosides. In some embodiments, the modified nucleosides in each of the X and Z domains comprise 2'-OMe modified nucleosides and conformationally restricted nucleosides optionally linked through thiophosphate intersubunit linkages, and wherein the 2'-OMe modified nucleosides include 5-methylcytosine nucleobases, but optionally not cytosine. In some embodiments, the modified nucleosides in each of the X and Z domains comprise 2'-OMe and conformationally restricted nucleosides. In some embodiments, the modified nucleosides in each of the X and Z domains comprise conformationally restricted nucleosides and, wherein at least one modified nucleoside includes a N3'→P5' phosphoramidate or a N3'→P5' thiophosphoramidate intersubunit linkage. In some embodiments, the Y domain comprises 7-8 2'-deoxy-nucleosides. In some embodiments, the 2'-OMe modified nucleosides include 5-methyluracil nucleobases, but optionally not uracil. In some embodiments, the Y domain comprises 9-10 2'-deoxy-nucleosides.

In some embodiments, the X and Z domains comprise nucleotides represented by the Formula (A1):

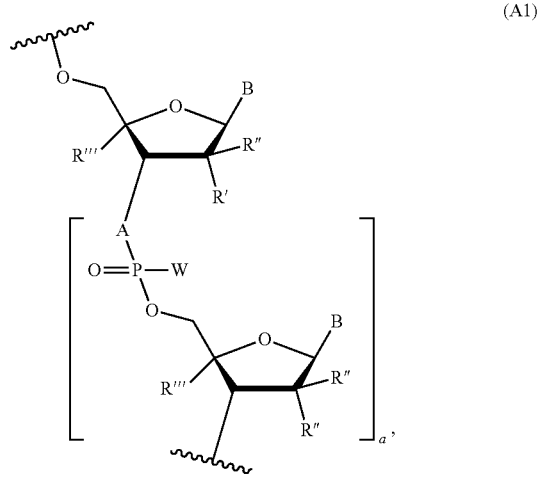

(A1)

wherein A is independently in each instance NH or O; B is independently in each instance an unmodified or modified nucleobase; W is independently in each instance OR or SR, where R is H or a positively charged counter ion; R' and R" are each independently in each instance selected from the group consisting of H, F, Cl, OH, OMe, Me, and O-methoxyethoxy; R''' is H, or R' and R''' together form —O—CH$_2$— or —O—(CH$_2$)$_2$—, and a is an integer of 3 to 9, wherein when R', R" and R''' are each H, then A is NH, and optionally when A is O, then W is SR.

In some embodiments, the ligand targeting group is selected from the group consisting of tocopherols, palmitic acid and lipoic acid and combinations thereof.

In some embodiments, the X and/or Z domain comprises one or more oligonucleotide where the modification is 2'-O-methoxyethoxy-N3'→P5'. In some embodiments, the X domain comprises one or more oligonucleotide where the modification is 2'-O-methoxyethoxy-N3'→P5'. In some embodiments, the Z domain comprises one or more oligonucleotide where the modification is 2'-O-methoxyethoxy-N3'→P5'. In some embodiments, the construct of said oligonucleotide corresponds to a construct of Table B.

Other embodiments include a chimeric oligonucleotide comprising a sequence complementary to at least a portion of the MAPT gene sequence where one or more nucleotides of the oligonucleotide are nucleotides of Formula (VII):

$$5'\text{-}X'\text{-}Y'\text{-}Z'\text{-}3'$$

(VII), wherein X'-Y'-Z' is a chimeric oligonucleotide comprising a sequence of 16 to 22 nucleosides, and is optionally conjugated at the 5' and/or 3' end; X' is a domain comprising a sequence of modified nucleosides that is 3-10 nucleosides in length; Z' is a domain comprising a sequence of modified nucleosides that is 3-10 nucleosides in length; and Y' is a domain comprising a sequence of 2 to 4 2'-deoxy-nucleosides linked through intersubunit linkages, wherein the X' and/or Z' domains comprise a sequence of modified nucleosides linked through N3'→P5' phosphoramidate or N3'→P5' thiophosphoramidate intersubunit linkages. In some embodiments, the Y' domain consists of 2'-deoxy-nucleosides linked through thiophosphate intersubunit linkages, and optionally one phosphodiester intersubunit linkage. In some embodiments, the X' domain is 9 or 10 nucleosides in length. In some embodiments, the X' domain comprises modified nucleosides where the modification is selected from the group consisting of 2'-F, 2'-F—N3'→P5', 2'-OMe, 2'-OMe-N3'→P5', 2'-O-methoxyethoxy, 2'-O-methoxyethoxy-N3'→P5', and conformationally restricted nucleosides. In some embodiments, the Z' domain comprises modified nucleosides where the modification is selected from the group consisting of 2'-F, 2'-F—N3'→P5', 2'-OH, 2'-OMe, 2'-OMe-N3'→P5', 2'-O-methoxyethoxy, 2'-O-methoxyethoxy-N3'→P5', and conformationally restricted nucleosides. In some embodiments, the X' and/or Z' domains comprise one or more 2'-arabino-F and/or 2'-ribo-F modified nucleoside. In some embodiments, the modified nucleosides in the X' and/or Z' domains comprise 2'-OMe and conformationally restricted nucleosides. In some embodiments, the modified nucleosides in the X' and/or Z' domains comprise conformationally restricted nucleosides and a N3'→P5' modification. In some embodiments, the sequence is selected from those in Table B having a 2-4 nucleotide Y domain.

Other embodiments include a chimeric oligonucleotide comprising a sequence complementary to at least a portion of the MAPT gene sequence, wherein the nucleobase sequence of the oligonucleotide corresponds to a sequence listed in Table D.

Other embodiments include an oligonucleotide comprising a sequence complementary to at least a portion of the MAPT gene sequence where one or more nucleotides of the oligonucleotide are nucleotides of the following Formula (VIII):

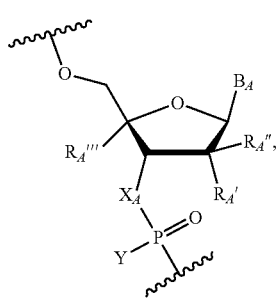

(VIII)

wherein $X_A$ is NH or O, Y is OR or SR, where R is H or a positively charged counter ion, $B_A$ is independently in each instance a natural or an unmodified nucleobase or a modified nucleobase, $R_A'$ and $R_A''$ are each independently in each instance selected from H, F, OH, OMe, Me, O-methoxyethoxy, and $R_A'''$ is H or $R_A'$ and $R_A'''$ together form —O—CH$_2$— or —O—(CH$_2$)$_2$—. In some embodiments, $R_A'$ and $R_A'''$ are H; and $R_A''$ is F. In some embodiments, $R_A'$ and $R_A''$ are H; and $R_A'''$ is F, OH, H or OMe. In some embodiments, $X_A$ is NH; $B_A$ is an unmodified or modified nucleobase; $R_A'$ and $R_A'''$ together form a conformationally restricted nucleoside (e.g., —O—CH$_2$— or —O—(CH$_2$)$_2$—); and $R_A''$ is H. In some embodiments, at least one of $R_A'$ and $R_A''$ is H. In some embodiments, when $B_A$ is a purine nucleobase at least one of $R_A'$ and $R_A''$ is OH or F, and/or when $B_A$ is a pyrimidine nucleobase at least one of $R_A'$ and $R_A''$ is OMe, OH or F. In some embodiments, the modified nucleobase is selected from 5-methylcytosine, 2,6-diaminopurine, 5-methyluracil, and a g-clamp.

Other embodiments include an oligonucleotide comprising a sequence complementary to at least a portion of the MAPT gene sequence where ten or more nucleotides of the oligonucleotide are nucleotides of the following Formula (IX):

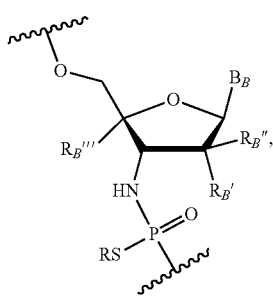

(IX)

wherein R is H or a positively charged counter ion, $B_B$ is independently in each instance a natural or an unmodified nucleobase or a modified nucleobase, $R_B'$ and $R_B''$ are each independently in each instance selected from H, F, OMe, Me, O-methoxyethoxy, and $R_B'''$ is H or $R_B'$ and $R_B'''$ together form —O—CH$_2$— or —O—(CH$_2$)$_2$—. In some embodiments, $R_B'$ and $R_B''$ are H; and $R_B'''$ is F. In some embodiments, $R_B'$ and $R_B''$ are H; and $R_B'''$ is F, OH, H or OMe. In some embodiments, $B_B$ is an unmodified or modified nucleobase; $R_B'$ and $R_B'''$ together form a conformationally restricted nucleoside (e.g., —O—CH$_2$— or —O—(CH$_2$)$_2$—); and $R_B''$ is H. In some embodiments, at least one of $R_B'$ and $R_B''$ is H. In some embodiments, when $B_B$ is a purine nucleobase at least one of $R_B'$ and $R_B''$ is OH or F, and/or when $B_B$ is a pyrimidine nucleobase at least one of $R_B'$ and $R_B''$ is OMe, OH or F. In some embodiments, the modified nucleobase is selected from 5-methylcytosine, 2,6-diaminopurine, 5-methyluracil, and a g-clamp.

In some embodiments, the nucleotides of Formula (B) include those in Table A where $X_A$ is NH. In some embodiments, the nucleotide of Formula (B) are arranged and modified in accordance with the constructs listed in Table B. In some embodiments, the construct of Formula (B) includes a sequence 1, 2, 3, 4, or 5 nucleobases different from a sequence selected from those in Table D. In some embodiments, every oligonucleotide is a nucleotide of Formula (B).

In embodiments, the nucleobase sequence of the oligonucleotide corresponds to SEQ ID NO: 1. In embodiments, the sequence of SEQ ID NO: 1 is modified according to at least one of the disclosed modifications. In embodiments, at least the first two nucleotides from the 5' and 3' ends of the oligonucleotide having a nucleobase sequence corresponding to SEQ ID NO: 1 are modified to include a phosphoramidate linkage and further modified to include a 2'-methoxyethoxy (2'MOE) modification. In embodiments, at least the first three nucleotides from the 5' and 3' ends of the oligonucleotide having a nucleobase sequence corresponding to SEQ ID NO: 1 are further modified to include a 2'MOE modification. In embodiments, at least the first four nucleotides from the 5' and 3' ends of the oligonucleotide having a nucleobase sequence corresponding to SEQ ID NO: 1 are further modified to include a 2'MOE modification. In embodiments, at least the first five nucleotides from the 5' and 3' ends of the oligonucleotide having a nucleobase sequence corresponding to SEQ ID NO: 1 are further modified to include a 2'MOE modification. In embodiments, at least the first six nucleotides from the 5' and 3' ends of the oligonucleotide having a nucleobase sequence corresponding to SEQ ID NO: 1 are further modified to include a 2'MOE modification.

Other embodiments include a pharmaceutical composition comprising an oligonucleotide of any of the preceding embodiments and a pharmaceutically acceptable excipient. In some embodiments, the composition is suitable for intrathecal or intracerebroventricular delivery. Other embodiments include a method of inhibiting MAPT gene expression in a central nervous system (CNS) cell, such as a neuron, astrocyte, oligodendrocyte and microglia, comprising contacting the cell with an oligonucleotide or composition of any of the preceding embodiments. Other embodiments include a method of inhibiting transcription or translation of MAPT in a CNS cell comprising contacting the cell with an oligonucleotide or composition of any of the preceding embodiments. Other embodiments include a method of treating a subject having tauopathy such as Alzheimer's disease (AD) and/or any tauopathy-related disorder comprising administering to the subject a therapeutically effective amount of an oligonucleotide or composition of any of the preceding embodiments. Other embodiments include an oligonucleotide of any of the preceding embodiments, wherein said oligonucleotide complexed with at least a portion of the MAPT gene sequence has a melting temperature (Tm) of >37° C. Other embodiments include a method of treating a subject having tauopathy such as Alzheimer's disease (AD) and/or any tauopathy-related disorder comprising administering to the subject a therapeutically effective amount of an oligonucleotide or composition of any of the preceding embodiments. Other embodiments include a method of inhibiting expression of a target RNA in a CNS cell comprising contacting the cell with an oligonucleotide or composition comprising said oligonucleotide of any of the preceding embodiments, wherein the chimeric oligonucleotide contains a nucleobase sequence that is complementary or hybridizes to a portion of the target RNA. Other embodiments include a method of inhibiting transcription or translation of the MAPT gene in a CNS cell comprising contacting the cell with an oligonucleotide or composition comprising said oligonucleotide of any of the preceding embodiments, comprising said oligonucleotide contains a nucleobase sequence that is complementary or hybridizes to at least a portion of the MAPT gene. Other embodiments include a method of treating a subject having tauopathy such as Alzheimer's disease (AD) and/or any tauopathy-related disorder, comprising administering to the subject a therapeutically effective amount of an oligonucleotide or composition comprising said oligonucleotide of any of the preceding embodiments, wherein the oligonucleotide contains a nucleobase sequence that is complementary or hybridizes to at least a portion of the MAPT gene. Other embodiments include a method of modulating expression of a target by contacting a target nucleic acid with an antisense compound comprising an oligonucleotide or composition comprising said oligonucleotide of any of the preceding embodiments, wherein the oligonucleotide contains a nucleobase sequence that is complementary to, or hybridizes to, a portion of the target nucleic acid.

DETAILED DESCRIPTION

The present disclosure is directed to oligonucleotides comprising a sequence complementary to at least a portion of the MAPT gene sequence where one or more nucleotides of the oligonucleotide are modified nucleotides and two or more nucleotides contain modified linkages between the nucleotides. The present disclosure is also directed to constructs of the oligonucleotides, which include domains, regions or portions within the oligonucleotide having common features and additional components conjugated to the oligonucleotide such as targeting moieties. The present disclosure is further directed to methods of using and preparing the oligonucleotides and their constructs.

As known in the art and as set forth in the present disclosure, a modified nucleotide is any nucleotide that is not a deoxyribonucleotide. For example, the 2' carbon of the deoxyribose may be substituted by a substituent other than the hydroxy (OH); the 3' carbon of the deoxyribose may be substituted by a substituent other than the oxygen atom (O). As known in the art and as set forth in the present disclosure, a modified linkage between two nucleotides is any linkage that is not a phosphodiester bond between the 3' carbon of the deoxyribose of the first nucleotide and the 5' carbon of the deoxyribose of the second nucleotide.

1. 2', 3'-Modified Nucleotides and Related Oligonucleotides

Compounds of the present disclosure include oligonucleotides comprising a sequence complementary to at least a portion of the MAPT gene sequence where one or more nucleotides of the oligonucleotide are modified nucleotides with particular 2' and 3' modifications. In embodiments, compounds of the present disclosure include replacement of the hydroxy, or substitution, at the 2' carbon of the deoxyribose sugar. In addition, these compounds of the present disclosure include modifications of the linkage between two nucleosides, which includes replacement of the oxygen atom, or substitution, with a nitrogen atom (N) at the 3' carbon of the deoxyribose sugar. Modifications of the linkage further include replacement of another oxygen atom, or substitution, in the phosphodiester bond.

These modified nucleotides may be used, e.g., in oligonucleotides such as chimeric oligonucleotides allowing for enzymatic cleavage of the genetic target by RNase H or modified antisense oligonucleotides.

2', 3'-Modified Nucleotides

Accordingly, compounds of the present disclosure include oligonucleotides comprising a sequence complementary to at least a portion of the MAPT gene sequence where one or more nucleotides of the oligonucleotides are nucleotides of Formula (I):

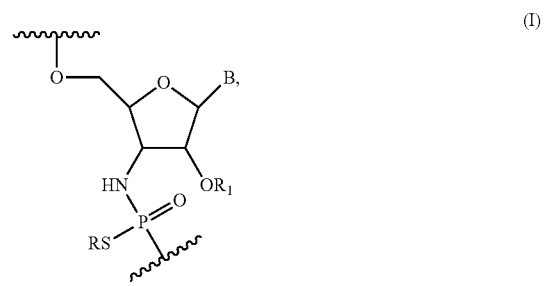

(I)

wherein R is H or a positively charged counter ion, B is independently in each instance a natural or an unmodified nucleobase or a modified nucleobase, $R_1$ is $-(CR'_2)_2OCR'_3$, and R' is independently in each instance H or F.

In nucleotides of Formula (I), $R_1$ is $-(CR'_2)_2OCR'_3$. In some embodiments, R' is H in each instance. In other embodiments, at least one R' is F, for example, 1, 2, 3, 4, 5, 6, or 7 R's are F. In some embodiments, $CR'_3$ contains 1, 2 or 3 F moieties. For example, in embodiments, $R_1$ is selected from the group consisting of $-CH_2CH_2OCH_3$ (or MOE), $-CF_2CH_2OCH_3$, $-CH_2CF_2OCH_3$, $-CH_2CH_2OCF_3$, $-CF_2CF_2OCH_3$, $-CH_2CF_2OCF_3$, $-CF_2CH_2OCF_3$, $-CF_2CF_2OCF_3$, $-CHFCH_2OCH_3$, $-CHFCHFOCH_3$, $-CHFCH_2OCFH_2$, $-CHFCH_2OClF_2$ and $-CH_2CHFOCH_3$. In embodiments, the nucleotide of Formula I is:

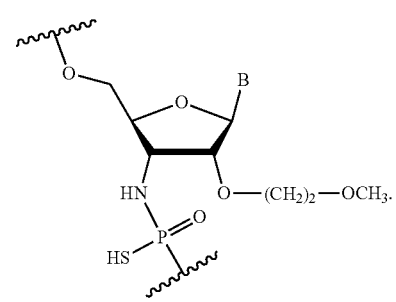

In embodiments, compounds of the present disclosure include oligonucleotides comprising a sequence complementary to at least a portion of the MAPT gene sequence where one or more nucleotides of the oligonucleotides are nucleotides of Formula (II):

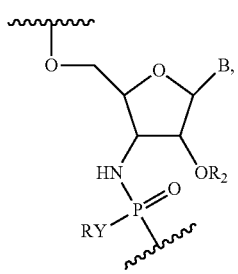

(II)

wherein Y is S or O, R is H or a positively charged counter ion, B is a nucleobase, R$_2$ is —CR'$_3$, —CR'$_2$OCR'$_3$, —(CR'$_2$)$_3$OCR'$_3$ or —(CR'$_2$)$_{1-2}$CR'$_3$, or R$_2$ is —(CR'$_2$)$_2$OCR'$_3$ and Y is O and R' is independently in each instance H or F.

In the nucleotide of Formula (II), R$_2$ is —CR'$_3$, —(CR'$_2$)$_{1-3}$OCR'$_3$, or —(CR'$_2$)$_1$-2CR'$_3$. In some embodiments, R$_2$ is —CR'$_3$ or —CR'$_2$CR'$_3$. In some embodiments, R' is H in each instance. In other embodiments, at least one R' is F, for example, 1, 2, 3, 4, or 5 R's are F. In some embodiments, CR'$_3$ contains 1, 2 or 3 F moieties. For example, in embodiments, R$_2$ is selected from the group consisting of —CH$_3$ (or Me), —CFH$_2$, —CHF$_2$, CF$_3$, —CH$_2$OCH$_3$, —CFH$_2$OCH$_3$, —CHF$_2$OCH$_3$, —CF$_3$OCH$_3$, —CH$_2$OCFH$_2$, —CH$_2$OCHF$_2$, —CH$_2$OCF$_3$, —CFH$_2$OCH$_3$, —CFH$_2$OCFH$_2$, —CFH$_2$OCHF$_2$, —CFH$_2$OCF$_3$, —CHF$_2$OCH$_3$, —CHF$_2$OCFH$_2$, —CHF$_2$OCHF$_2$, —CHF$_2$OCF$_3$, —(CR'$_2$)$_3$OCR'$_3$, —CH$_2$CH$_3$ (or Et), —CFH$_2$CH$_3$, —CHF$_2$CH$_3$, —CF$_3$CH$_3$, —CH$_2$CFH$_2$, —CH$_2$CHF$_2$, —CH$_2$CF$_3$, —CFH$_2$CH$_3$, —CFH$_2$CFH$_2$, —CFH$_2$CHF$_2$, —CFH$_2$CF$_3$, —CHF$_2$CH$_3$, —CHF$_2$CFH$_2$, —CHF$_2$CHF$_2$, —CHF$_2$CF$_3$, —CH$_2$CH$_2$CH$_3$, CF$_2$CH$_2$CH$_3$, CH$_2$CF$_2$CH$_3$, CH$_2$CH$_2$CF$_3$, CF$_2$CF$_2$CH$_3$, CH$_2$CF$_2$CF$_3$, CF$_2$CH$_2$CF$_3$, CF$_2$CF$_2$CF$_3$, CHFCH$_2$CH$_3$, CHFCHFOCH$_3$, CHFCH$_2$CFH$_2$, CHFCH$_2$CHF$_2$ and CH$_2$CHFCH$_3$. In embodiments, R$_2$ is —CH$_3$ (or Me) or —CH$_2$CH$_3$ (or Et).

In embodiments, the nucleotides of Formula II are selected from the group consisting of

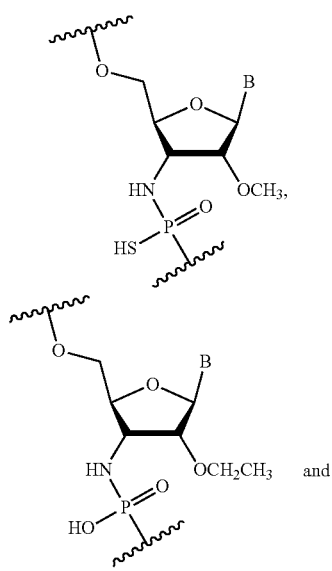

and

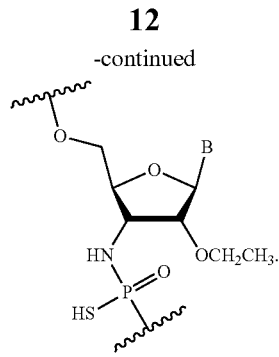

In compounds of Formulae (I) or (II), Y may be O or S. In some embodiments, Y is S in at least one instance (e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30 etc.). In other embodiments, Y is S in at least one instance and O in at least another instance. In other embodiments, Y is S in each instance. In some embodiments, Y is O in at least one instance (e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30 etc.).

The disclosed oligonucleotides comprise at least one nucleotide of Formula (I). In embodiments, the disclosed oligonucleotides comprise 1, 2, 3, 4, 5, 6, 7, 8, 9, 10, 11, 12, 13, 14, 15, 16, 17, 18, 19, 20, 21, 22, 23, 24 nucleotides of Formula (I). In embodiments, the disclosed oligonucleotides comprise 1, 2, 3, 4, 5, 6, 7, 8, 9, 10, 11, 12, 13, 14, 15, 16, 17, 18, 19, 20, 21, 22, 23, 24 nucleotides of Formula (II). In some embodiments, the oligonucleotide comprises from 2 to 40 nucleotides, for example, 8 to 26 nucleotides or integers therebetween.

In embodiments where more than one nucleotide of Formula (I) are included in the oligonucleotide, the nucleotide may be the same or different. In some embodiments one or more nucleotides of Formula (II) are included and may be the same or different. For example, in some embodiments, the oligonucleotide comprises at least one nucleotide of Formula (I) and at least one nucleotide of Formula (II). In some embodiments, the oligonucleotide comprises at least one nucleotide of Formula (I), wherein at least one R$_1$ is MOE and at least one nucleotide of Formula (II), wherein R$_2$ is Me or Et. In some embodiments, the oligonucleotide comprises at least 2 alternating nucleotides of Formula (I) and Formula (II). For example, 2, 3, 4, 5, 6, 7, 8, 9, 10, 11, 12, 13, 14, 15, 16, 17, 18, 19, 20, 21, 22, 23, 24 nucleotides with alternating 2' modification (e.g., Me-MOE-Me-MOE . . . or Et-MOE-Et-MOE-Et-MOE . . . ).

In some embodiments, the nucleotide of Formula (I) and/or Formula (II) is represented by the following:

(I')

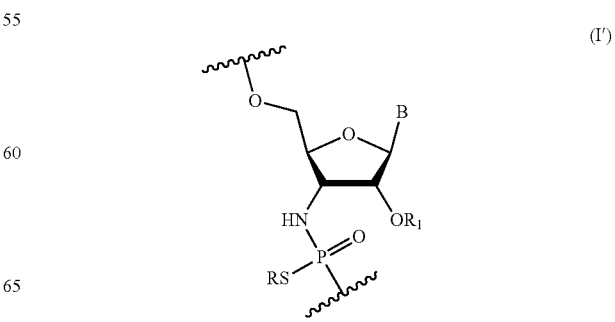

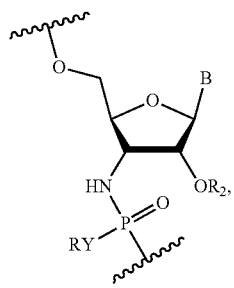
(II')

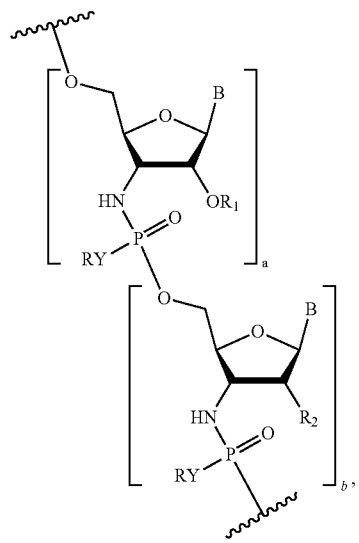
(IV)

In some embodiments, the oligonucleotide comprising the nucleotide of Formula (I) further comprises a 2'-fluoronucleotide of the Formula (IIIa) and/or (IIIb):

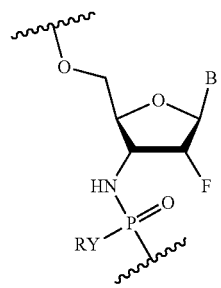
(IIIa)

wherein Y is S or O, R is H or a positively charged counter ion, B is a nucleobase, $R_1$ is —$(CR'_2)_2OCR'_3$, $R_2$ is selected from —$OCR'_3$, —$OCR'_2OCR'_3$, —$O(CR'_2)_3OCR'_3$ or —$O(CR'_2)_{1-2}CR'_3$ and F, R' is independently in each instance H or F, and a is an integer of 1-10 and b is an integer from 1-10, where the to 20, e.g., 1, 2, 3, 4, 5, 6, 7, 8, 9, 10, 11, 12, 13, 14, 15, 16, 17, 18, 19 and 20.

Compounds of the present disclosure include oligonucleotides comprising a sequence complementary to at least a portion of the MAPT gene sequence where one or more nucleotides of the oligonucleotides are nucleotides of Formula (III'):

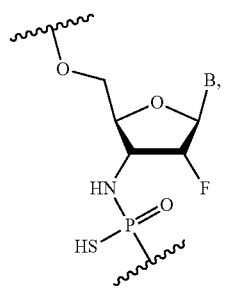
(III')

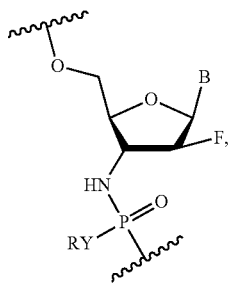
(IIIb)

wherein Y is S or O, R is H or a positively charged counter ion, and B is independently in each instance a natural or an unmodified nucleobase or a modified nucleobase; and optionally comprising one or more of formula (I), (II), and/or (IV).

The nucleobases, B, of the nucleotides of Formulae (I), (II), (IIIa), (IIIb), (IV) and (V) may each independently be a natural or an unmodified nucleobase or a modified nucleobase. In some embodiments, the modified nucleotides include 2,6-diaminopurine nucleobases, but optionally not adenine. In some embodiments, the modified nucleotides include 5-methyluracil nucleobases, but optionally not uracil. In some embodiments, the modified nucleotides include 2,6-diaminopurine nucleobases, but not adenine and 5-methyluracil nucleobases, but optionally not uracil.

wherein Y is S or O, R is H or a positively charged counter ion, and B is a nucleobase.

In some embodiments, the oligonucleotide comprises at least 4 alternating nucleotides of Formulae (I) and (IIIa). For example, the oligonucleotide comprises 4, 5, 6, 7, 8, 9, 10, 11, 12, 13, 14, 15, 16, 17, 18, 19, 20, 21, 22, 23, 24 alternating nucleotides.

Certain embodiments include an oligonucleotide comprising 4-40 nucleotides, and comprising Formula (IV):

Y in each nucleotide of Formulae (II), (IIIa), (IIIb), (IV) and (V) may be independently O or S. In some embodiments, Y is S in at least one instance (e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30 etc.). In other embodiments, Y is S in at least one instance and O in at least another instance. In other embodiments, Y is S in each instance. In some embodiments, Y is O in at least one instance (e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30 etc.).

In embodiments where more than one nucleotide of each of Formulae (I), (II), (IIIa), (IIIb), (IV) and (V) are included, the more than one nucleotide of such Formulae may be the same or different. For example, in some embodiments, the nucleotide comprises at least one nucleotide of Formula (II), (III), (IV), (V) and/or (V') in addition to at least one nucleotide of Formula (I). In some embodiments, the nucleotide comprises at least 2 alternating nucleotides of Formula (I) and/or Formula (II) and/or (III) and/or (IV), (V) and/or (V'). For example, disclosed oligonucleotides may include 2, 3, 4, 5, 6, 7, 8, 9, 10, 11, 12, 13, 14, 15, 16, 17, 18, 19, 20, 21, 22, 23, 24 nucleotides with alternating 2' modifications.

In embodiments, the nucleotides of the oligonucleotide are selected from the group consisting of:

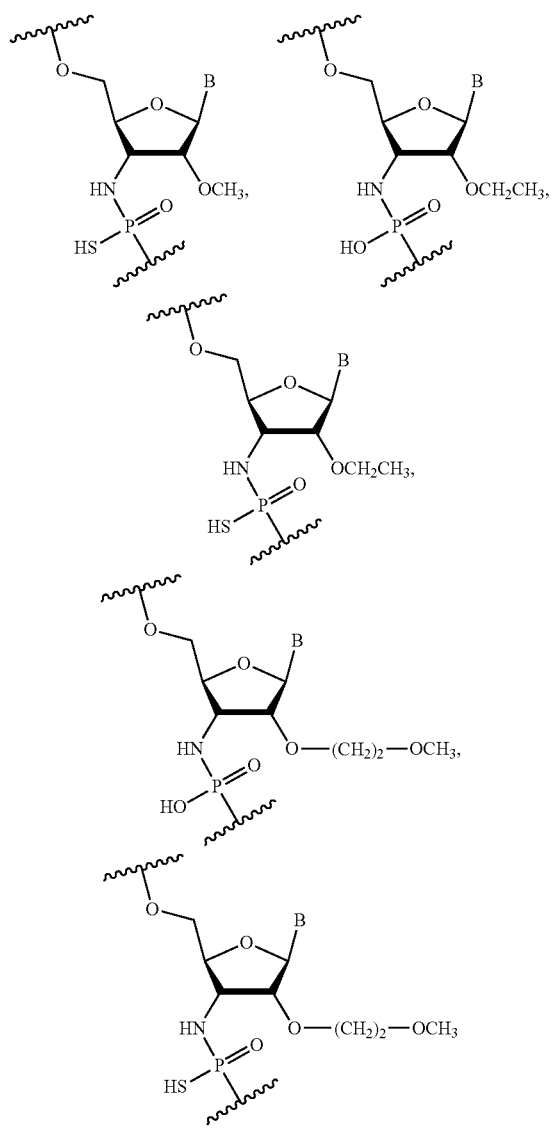

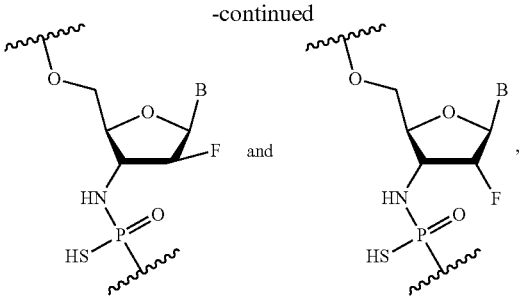

-continued where B can be any natural or modified base.

Compounds of the present disclosure include oligonucleotides comprising a sequence complementary to at least a portion of the MAPT gene sequence where one or more nucleotides of the oligonucleotides are nucleotides of Formula (V'):

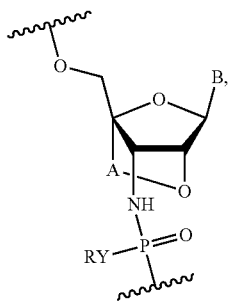

(V')

wherein Y is S or O, R is H or a positively charged counter ion, B is independently in each instance a natural or an unmodified nucleobase or a modified nucleobase, A is —(CR"R")$_{1-2}$— and R" is independently in each instance H, F or Me, and optionally comprising one or more of Formulae (I), (II), (III), (IV) or (V).

In the compound comprising formula (V'), A is —(CR"R")$_{1-2}$—. In some embodiments, A is —(CR"R")— in other embodiments, A is —(CR"R")$_2$—. R" is independently in each instance H or Me. In some embodiments, one R" is Me and remaining are H. In other embodiments, all R" are H.

In some embodiments, when A is CH$_2$, then Y is S. In other embodiments, when A is CH$_2$CH$_2$, then Y is O or S. In some embodiments, A is CH$_2$CH(Me) or CH(Me) and Y is O or S.

In the compound comprising formula (V'), Y is O or S. In some embodiments, Y is S in at least one instance (e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30 etc.). In other embodiments, Y is S in at least one instance and O in at least another instance. In other embodiments, Y is S in each instance. In some embodiments, Y is O in at least one instance (e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30 etc.).

The compound of Formula (V') (and optionally Formulae (I), (II), (III), (IV), (V) and/or (V')) may be part of an oligonucleotide. In some embodiments, the compound comprising Formula (IV) (and optionally Formulae (I), (II), (III), (IV), (V) and/or (V')) is an oligonucleotide comprising 1, 2, 3, 4, 5, 6, 7, 8, 9, 10, 11, 12, 13, 14, 15, 16, 17, 18, 19, 20, 21, 22, 23, 24 nucleotides of Formula (V') (and Formulae (I), (II), (III), (IV), (V) and/or (V')). In some embodiments, the oligonucleotide comprises from 2 to 40 nucleotides, for example, 8 to 26 nucleotides or integers there between.

In embodiments where more than one nucleotide of Formula (V') are included, the more than one nucleotide of Formula (V') may be the same or different. In some embodiments one or more nucleotides of Formulae (I), (II), (III), (IV), (V) and/or (V') are included and may be the same or different. For example, in some embodiments, the nucleotide comprises at least one nucleotide of Formula (V') and at least one nucleotide of Formulae (I), (II), (III), (IV), (V) and/or (V'). In some embodiments, the nucleotide comprises at least 2 alternating nucleotides of Formula (V') and Formula (I) and/or (II). For example, 2, 3, 4, 5, 6, 7, 8, 9, 10, 11, 12, 13, 14, 15, 16, 17, 18, 19, 20, 21, 22, 23, 24 nucleotides with alternating 2' modification.

In some embodiments, the nucleotide comprising the nucleotide of Formula (V') (and optionally Formulae (I), (II), (III), (IV), (V) and/or (V')) further comprises a 2-fluoronucleotide of the following structures:

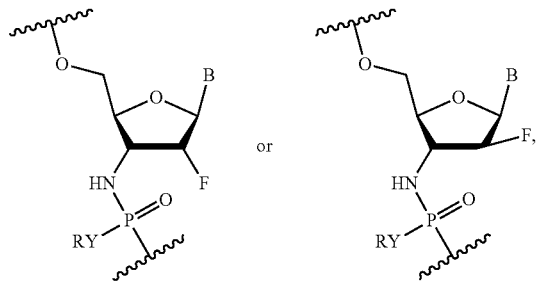

where Y, R and B are the same as for Formula (I). In some embodiments, the nucleotide comprises at least 4 alternating nucleotides of Formula (V') and 2-fluoronucleotides.

Compounds of the present disclosure include oligonucleotides comprising a sequence complementary to at least a portion of the MAPT gene sequence where one or more nucleotides of the oligonucleotides are nucleotides of Formula (V):

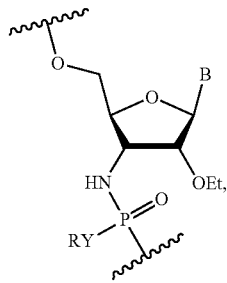

wherein Y is S or O, R is H or a positively charged counter ion, and B is independently in each instance a natural or an unmodified nucleobase or a modified nucleobase; and optionally comprising one or more of formula (I), (II), (III), (IV) and/or (V').

Chimeric Oligonucleotides

The present disclosure is directed to constructs of oligonucleotides comprising a sequence complementary to at least a portion of the MAPT gene sequence, which include domains, regions or portions within the oligonucleotide having common features. Oligonucleotides having these domains are referred to herein as chimeric oligonucleotides. In some embodiments, chimeric oligonucleotides are represented by Formula (VI):

$$5'\text{-}X\text{-}Y\text{-}Z\text{-}3' \qquad (VI),$$

wherein the chimeric oligonucleotide comprises a sequence of 14 to 22 nucleosides, wherein X is a domain comprising a sequence of modified nucleotides that is 3-10 nucleotides in length; Z is a domain comprising a sequence of modified nucleotides that is 3-10 nucleosides in length; and Y is a domain comprising a sequence of 2-10 2'-deoxy-nucleotides, or unmodified nucleotides. Each of the nucleosides in each of the domains is linked through intersubunit linkages.

In some embodiments, chimeric oligonucleotides comprising a sequence complementary to at least a portion of the MAPT gene sequence include one or more nucleotides of Formula (VI'):

$$5'\text{-}X\text{-}Y\text{-}Z\text{-}3' \qquad (VI'),$$

wherein the chimeric oligonucleotide comprises a sequence of 14 to 22 nucleosides, wherein X is a domain comprising a sequence of modified nucleotides that is 2-10 nucleotides in length; Z is a domain comprising a sequence of modified nucleotides that is 2-10 nucleosides in length; and Y is a domain comprising a sequence of 6-14 2'-deoxy-nucleotides, or unmodified nucleotides. Each of the nucleosides in each of the domains is linked through intersubunit linkages.

Nucleotides of formula (I), (II), (IIIa), (IIIb), (IV), (V) and/or (V') may be present in the X and/or Z domain. Chimeric oligonucleotide may be conjugated at the 5' and/or 3' end to a ligand-targeting group.

In some embodiments, the Y domain contains 2'deoxy-nucleosides linked by thiophosphate intersubunit linkages. In embodiments, the Y domain contains 2'deoxy-nucleosides linked by at least one phosphodiester intersubunit linkage. In embodiments, the Y domain contains 2'deoxy-nucleosides linked by two phosphodiester intersubunit linkages. In embodiments, the Y domain contains 2'deoxy-nucleosides linked by thiophosphate intersubunit linkages and one or two phosphodiester intersubunit linkages. In some embodiments, the Y domain is 6 to 10 nucleotides in length.

In some embodiments, the X domain comprises nucleotides of formulae (I), (II), (IIIa), (IIIb), (IV), (V) and/or (V'). In some embodiments, the X domain comprises modified nucleotides where the modification is independently selected from 2'-OMe, 2'-OEt, 2'-O-methoxyethoxy, and conformationally restricted nucleotides. In some embodiments, the X domain is 9 or 10 nucleotides in length.

In some embodiments, the Z domain comprises nucleotides of formulae (I), (II), (IIIa), (IIIb), (IV), (V) and/or (V'). In some embodiments, the Z domain comprises 2' modified nucleotides where the modification is 2'-OMe, 2'-OEt or 2'-MOE. In some embodiments, the Z domain is 9 or 10 nucleotides in length.

In embodiments, the chimeric oligonucleotide comprises a sequence of 14 to 22 nucleotides. For example, the oligonucleotide may include 14, 15, 16, 17, 18, 19, 20, 21 or 22 nucleotides.

In embodiments, X is a domain consisting of a sequence containing one or more modified nucleotides that is 3-10 nucleotides in length; Z is a domain consisting of a sequence containing one or more modified nucleotides that is 3-10 nucleotides in length; and Y is a domain consisting of a sequence of 2 to 10 2'-deoxy-nucleosides linked through thiophosphate intersubunit linkages and optionally one or two phosphodiester intersubunit linkages. In some embodiments, X is 5-9, Y is 6-10 and Z is 5-9. In some embodiments, the number of nucleotides in each of X, Y and Z, respectively is: 6/6/6, 6/6/7, 6/6/8, 6/7/6, 6/7/7, 6/7/8, 6/8/6, 6/8/7, 6/8/8, 3/10/3, 4/10/4, 5/10/5, 5/10/6, 2/12/2, 3/12/3, 2/14/2, 5/9/5, 5/9/6, 5/8/5, 5/8/6, 5/8/7, 7/5/7, 7/5/8, 7/5/9, 7/6/6, 7/6/7, 7/6/8, 7/6/9, 7/7/6, 7/7/7, 7/7/8, 7/7/9, 7/5/7, 7/5/8, 7/5/9, 7/4/7, 7/4/8, 7/4/9, 8/4/7, 8/4/8, 8/4/9, 7/3/7, 7/3/8, 7/3/9, 8/3/7, 8/3/8, 8/3/9, 8/3/10, 9/3/7, 9/3/8, 9/3/9, 9/3/10, 8/2/7, 8/2/8, 8/2/9, 8/2/10, 9/2/7, 9/2/8, 9/2/9, 9/2/10, 10/2/8, 10/2/9, 10/2/10. The X domain and the Z domain each, respectively, comprise a sequence of modified nucleotides, where the domain is 4-10 nucleotides in length. For example, the X domain and/or Z domain may comprise a sequence of 4, 5, 6, 7, 8, 9, or 10 nucleotides. One or more of these nucleotides is modified (e.g., 1, 2, 3, 4, 5, 6, 7, 8, 9 or 10). For example, in some embodiments, all the nucleotides in each of the X domain and/or Z domain are modified.

The nucleotides of the X and Z domains may be modified according to Formulae (I), (II), (IIIa), (IIIb), (IV), (V) and/or (V') with respect to one or more of their nucleobases, the 2' and/or 3' positions on the ribose sugar and their intersubunit linkages. Embodiments include wherein the 2' position is modified with an F (ribo or arabino) and the 3' position is O or NH. Embodiments also include wherein the 2' position is modified with an OMe and the 3' position is O or NH. Embodiments include wherein the 2' position is modified with an F (ribo or arabino) as well as Me or OMe, and the 3' position is O or NH. Embodiments include wherein the 2' position is modified with an F (ribo or arabino) and the 3' position is O or NH. Embodiments include wherein the 2' position is modified with an O-methoxyethoxy and the 3' position is O or NH. Embodiments also include wherein the 2' position is modified with an F (ribo or arabino) and the 3' position is O or NH. Embodiments include wherein the 2' and 4' positions are modified bridging group (as described elsewhere herein) to form a conformationally restricted nucleotide and the 3' position is O or NH. Each of these embodiments may include thiophosphate (or thiophosphoramidate depending on the 3' substitution) and phosphoramidate intersubunit linkages.

Embodiments also include oligonucleotides where the 2' position of at least one nucleotide is H, and the 3' position is NH. Each of these embodiments may include thiophosphoramidate and/or phosphoramidate intersubunit linkages.

In some embodiments, the modified nucleotides of the X domain and the Z domain each, respectively, include a modification independently selected from at least one of 2'-F, 2'-F—N3'→P5', 2'-OMe, 2'-OMe-N3'→P5', 2'-O-methoxyethoxy, 2'-O-methoxyethoxy-N3'→P5', conformationally restricted nucleotides.

In some embodiments, the modified nucleotide contains a nucleoside represented by the following Formula (A):

(A)

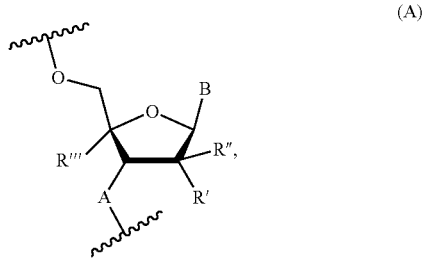

wherein A is independently in each instance NH or O, B is independently in each instance a natural or an unmodified nucleobase or a modified nucleobase, and R' and R" are each independently in each instance selected from H, F, OH, OMe, OEt, O-methoxyethoxy, and R'" is H, or R' and R'" together form a 2-4 atom bridge to form a conformationally restricted nucleoside (e.g., —O—$CH_2$—, —O—CH(Me)-, or —O—$(CH_2)_2$—).

In some embodiments, R' is selected from F, OH, —OMe, —OEt, O-methoxyethoxy; R" is H and F; and R'" is H, Me or —OMe. In other embodiments, R" and R'" are H; and R' is selected from F, OMe, OEt and O-methoxyethoxy. In some embodiments, A is NH in each instance.

Some embodiments include one or more modified nucleosides represented by Formula (A), wherein A is NH; B is a G-clamp; R' is F or OMe and R" is H; or R' is H and R" is H or F; and R'" is H.

Some embodiments include one or more modified nucleosides represented by Formula (A), wherein A is NH; B is an unmodified or modified nucleobase; R' and R'" together form a conformationally restricted nucleoside (e.g., —O—$CH_2$—, —O—CH(Me)-, or —O—$(CH_2)_2$—); and R" is H. In some embodiments, B is an unmodified or a modified nucleobase selected from the group consisting of 5-methylcytosine, 2,6-diaminopurine, and 5-methyluracil.

Some embodiments include one or more modified nucleosides represented by Formula (A), wherein A is NH; B is an unmodified or modified nucleobase; R' is F or OMe, R" is H and R'" is H.

Some embodiments include one or more modified nucleosides represented by Formula (A), wherein A is NH; B is an unmodified or modified nucleobase; R' is H, R" is F and R'" is H.

In some embodiments, the X and Z domains are represented by the Formula (A1):

(A1)

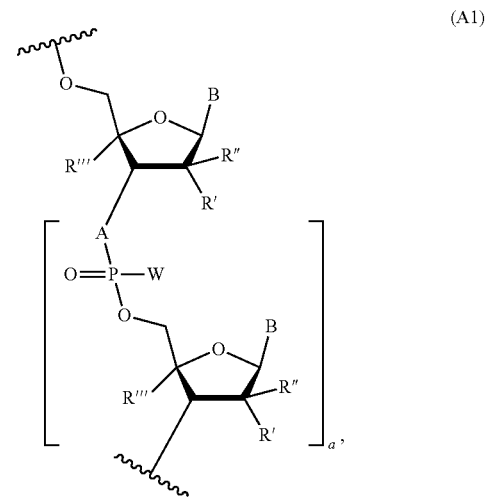

wherein W is independently in each instance OR or SR, where R is H or a positively charged counter ion; R', R", R'", A and B are as described for Formula (A). In other embodiments, A is O and R', R" are independently H or OEt, where at least one of R', R" is OEt.

For example, in addition to at least one nucleotide in each of the X and Z domains where A is NH, W is S, and R' is MOE, the nucleotides of X and/or Z may include one or more nucleotides of Formula A2 as described in Table A2 or one or more nucleotides of Formula A3 as described in Table A3.

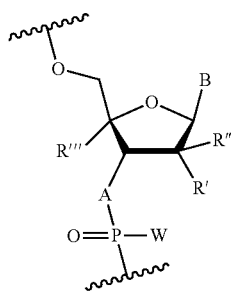

(A2)

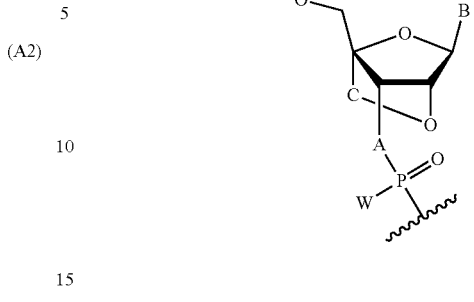

(A3)

TABLE A2

| Nucleotide No. | R' | R'' | R''' | A | W |
|---|---|---|---|---|---|
| 1 | F | H | H | NH | S |
| 2 | F | H | H | NH | O |
| 3 | F | H | H | O | S |
| 4 | F | H | H | O | O |
| 5 | H | F | H | NH | S |
| 6 | H | F | H | NH | O |
| 7 | H | F | H | O | S |
| 8 | H | F | H | O | O |
| 9 | OMe | H | H | NH | S |
| 10 | OMe | H | H | NH | O |
| 11 | OMe | H | H | O | S |
| 12 | OMe | H | H | O | O |
| 13 | H | F | H | NH | S |
| 14 | H | F | H | NH | O |
| 15 | H | F | H | O | S |
| 16 | H | F | H | O | O |
| 17 | O-methoxyethoxy | H | H | NH | S |
| 18 | O-methoxyethoxy | H | H | NH | O |
| 19 | O-methoxyethoxy | H | H | O | S |
| 20 | O-methoxyethoxy | H | H | O | O |
| 21 | H | H | H | NH | S |
| 22 | H | H | H | NH | O |
| 23 | OH | H | H | NH | S |
| 24 | OH | H | H | NH | O |
| 25 | OH | H | H | O | S |
| 26 | H | OH | H | NH | O |
| 27 | H | OH | H | NH | S |
| 28 | H | OEt | H | NH | O |
| 29 | H | OEt | H | NH | S |
| 30 | H | OEt | H | O | O |
| 31 | H | OEt | H | O | S |
| 32 | OEt | H | H | NH | O |
| 33 | OEt | H | H | NH | S |
| 34 | OEt | H | H | O | O |
| 35 | OEt | H | H | O | S |

TABLE A3

| Nucleotide No. | C | A | W |
|---|---|---|---|
| 36 | —O—CH$_2$— | NH | S |
| 37 | —O—CH$_2$— | NH | O |
| 38 | —O—CH$_2$— | O | S |
| 39 | —O—CH$_2$— | O | O |
| 40 | —O—(CH$_2$)$_2$— | NH | S |
| 41 | —O—(CH$_2$)$_2$— | NH | O |
| 42 | —O—(CH$_2$)$_2$— | O | S |
| 43 | —O—(CH$_2$)$_2$— | O | O |
| 44 | —O—CH(Me)— | NH | S |
| 45 | —O—CH(Me)— | NH | O |
| 46 | —O—CH(Me)— | O | S |
| 47 | —O—CH(Me)— | O | O |

In some embodiments, the X domain and Z domain each independently comprise two, three or more different nucleotides 1-47.

The nucleosides of the X domain are linked through intersubunit linkages, for example, N3'→P5' phosphoramidate, N3'→P5' thiophosphoramidate, thiophosphate, phosphodiester intersubunit linkages or combinations thereof. In some embodiments, the X domain is linked through intersubunit linkages selected from N3'→P5' phosphoramidate, N3'→P5' thiophosphoramidate, and combinations thereof.

The X domain of the chimeric oligonucleotide may include a certain arrangement of modified nucleotides. For example, in some embodiments, the X domain comprises one or more conformationally restricted nucleotides. Conformationally restricted nucleotides can include BNA, such as, LNA and ENA. (e.g., 1, 2, 3, 4, 5, 6, 7, 8, 9, 10 conformationally restricted nucleotides). In some embodiments, the X domain comprises one or more 2'-F and/or 2'-OMe modified nucleotides. In some embodiments, the X domain comprises alternating conformationally restricted nucleotides, e.g., every other nucleotide is a conformationally restricted nucleotide. In some embodiments, the X domain comprises one or more 2'-F and/or 2'-OMe modified nucleotide (e.g., 1, 2, 3, 4, 5, 6, 7, 8, 9, 10 2'-F and/or 2'-OMe modified nucleotides). In some embodiments, the X domain comprises alternating 2'-F and 2'-OMe modified nucleotides. In embodiments, the X domain comprises 2'-F or 2'-OMe and conformationally restricted nucleotides, for example, in an alternating sequence.

The Y domain comprises a sequence of 2 to 14 2'-deoxynucleotides. For example, the Y domain may comprise a sequence of 2, 3, 4, 5, 6, 7, 8, 9, 10, 11, 12, 13 or 14 2'-deoxynucleotides. One or more of the 2'-deoxynucleosides may be linked through thiophosphate intersubunit linkages (e.g., 1, 2, 3, 4, 5, 6, 7, 8, 9, 10, 11, 12, 13 or 14 thiophosphate intersubunit linkages). In some embodiments, each of the 2'-deoxynucleosides is linked through a thiophosphate intersubunit linkage. In some embodiments, the Y domain comprises at least one phosphodiester intersubunit linkage (e.g., 1, 2 or 3 phosphodiester intersubunit linkages). In other embodiments, the Y domain consists of 2'-deoxynucleosides linked through thiophosphate intersubunit linkages, and optionally one or two phosphodiester intersubunit linkages.

In embodiments, the Y domain comprises nucleotides that induce RNase H cleavage.

In some embodiments, the nucleotides of Formula (A) include those in Table A where $X_A$ is NH. In some embodiments, the nucleotide of Formula (A) are arranged and modified in accordance with the constructs listed in Table B. In some embodiments, the construct of Formula (A) includes a sequence 1, 2, 3, 4, or 5 nucleobases different from a sequence selected from those in Table D. In some embodiments, every nucleotide in an oligonucleotide is a nucleotide of Formula (A).

In some embodiments, the 2'-deoxynucleoside linked through a thiophosphate intersubunit linkage may be represented by the following Formula (B):

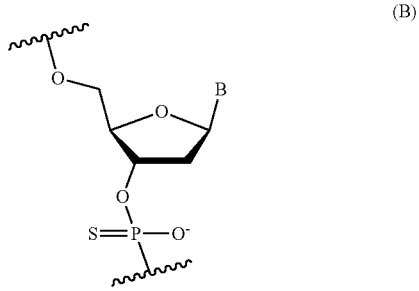

where B is independently in each instance an unmodified or modified nucleobase. In some embodiments, B is an unmodified or a modified nucleobase selected from the group consisting of 5-methylcytosine, 2,6-diaminopurine, and 5-methyluracil.

In other embodiments, the 2'-deoxynucleoside linked through a thiophosphate intersubunit linkage comprises a modified 2'-deoxynucleoside, which may be modified in the same manner as in the X and Z domain. For example, the modified 2'-deoxynucleoside linked through a thiophosphate intersubunit linkage may be represented by the following Formula (C):

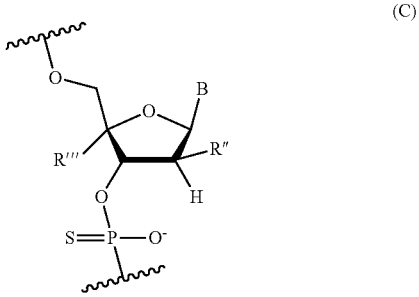

wherein B is independently in each instance an unmodified or modified nucleobase, and R" and R''' are each independently in each instance selected from H, F, Cl, OH, OMe, Me, O-methoxyethoxy, or R' and R''' together form a 2-4 atom bridge to form a conformationally restricted nucleoside. In some embodiments, B is an unmodified or a modified nucleobase selected from the group consisting of 5-methylcytosine, 2,6-diaminopurine, and 5-methyluracil.

[0081] The Z domain comprises a sequence of modified nucleotides, where the Z domain is 4-10 nucleotides in length. For example, the Z domain may comprise a sequence of 4, 5, 6, 7, 8, 9, or 10 nucleotides. One or more of these nucleotides is modified (e.g., 1, 2, 3, 4, 5, 6, 7, 8, 9, 10, 11, 12, 13, 14, 15, 16, 17, 18, 19, 20, 21 or 22). For example, in some embodiments, all the nucleotides in the Z domain are modified.

The modified nucleotides of the Z domain include, for example, a modification independently selected from at least one of 2'-F, 2'-F—N3'→P5', 2'-OMe, 2'-OMe-N3'→P5', 2'-OEt-N3'→P5', 2'-O-methoxyethoxy, 2'-O-methoxyethoxy-N3'→P5', conformationally restricted nucleotides, 2'-OH—N3'→P5' thiophosphoramidate and 2'-OH—N3'→P5' phosphoramidate.

The nucleotides of the Z domain may be linked through intersubunit linkages such as, for example, N3'→P5' phosphoramidate, N3'→P5' thiophosphoramidate, thiophosphate or phosphodiester intersubunit linkages. In some embodiments, the Z domain is linked through N3'→P5' phosphoramidate, N3'→P5' thiophosphoramidate, intersubunit linkages, and combinations thereof.

The Z domain of the chimeric oligonucleotide may include a certain arrangement of modified nucleotides. For example, in some embodiments, the Z domain comprises one or more (e.g., 1, 2, 3, 4, 5, 6, 7, 8, 9 or 10, or more) conformationally restricted nucleotides (e.g., BNA, such as, LNA, ENA, each of which may be optionally substituted). In some embodiments, the Z domain comprises alternating conformationally restricted nucleotides, e.g., every other nucleotide is a conformationally restricted nucleotide (e.g., BNA, such as, LNA, ENA, each of which may be optionally substituted). In some embodiments, the Z domain comprises one or more (e.g., 1, 2, 3, 4, 5, 6, 7, 8, 9 or 10, or more)$_2$'-F and/or 2'-OMe modified nucleotide. For example, some embodiments include where the Z domain comprises alternating 2'-F and 2'-OMe modified nucleotides, or the Z domain comprises alternating 2'-F or 2'-OMe and conformationally restricted nucleotides.

In some embodiments, the modified nucleotides of Formula (VI) or (VI') include 5-methylcytosine nucleobases, but not cytosine. In some embodiments, the modified nucleotides of Formula (VI) or (VI') include 2,6-diaminopurine nucleobases, but not adenine. In some embodiments, the modified nucleotides of Formula (VI) or (VI') include 5-methyluracil nucleobases, but not uracil. In some embodiments, the modified nucleotides of Formula (VI) or (VI') include 2'-OMe and conformationally restricted nucleotides, and are linked through thiophosphate intersubunit linkages, and the modified nucleotides include 5-methylcytosine nucleobases, but not cytosine. In some embodiments, the modified nucleotides of Formula (VI) or (VI') include the 2'-OMe modified nucleotides with 5-methyluracil nucleobases, but not uracil.

In certain embodiments, the nucleotides of Formula (VI) or (VI') in the chimeric oligonucleotide comprising a sequence complementary to at least a portion of the MAPT gene sequence are arranged according to at least one of the constructs of Table B where at least one intersubunit linkage in the X and Z domains is an NPS linkage.

TABLE B

| X Domain | | | Y Domain | | | Z Domain | | |
|---|---|---|---|---|---|---|---|---|
| Number of Nucs | Inter-subunit Linkages | Nucleo-base Substi-tutions | Number of Nucs | Inter-subunit Linkages | Nucleo-base | Number of Nucs | Inter-subunit Linkages | Nucleo-base Substi-tutions |
| 2, 3, 4, 5, 6, 7, 8, 9, 10, 11 and 12 | np, nps, ps, PO | A, G, C, T, U, DAP, 5meC, 5meU, G clamp, DAP | 2, 3, 4, 5, 6, 7, 8, 9, 10, 11 12, 13 and 14 | ps | A, G, C, T, U | 2, 3, 4, 5, 6, 7, 8, 9, 10, 11, and 12 | np, nps, ps, PO | A, G, C, T, U DAP, 5meC, 5meU, G clamp, DAP |

In Table B, the nucleotides in /5 each of the X and Z domains can be one or more of the numbered nucleotides in Tables A2 and A3. In some embodiments, the chimeric oligonucleotides of Table B include at least 1, 2, 3, 4, 5, 6, 7, 8 or more of the modified nucleotides in Table A. In some embodiments, all of the nucleotides of X and/or Z are modified nucleotides. In some embodiments, the nucleotides in Table B are selected from certain modified nucleotides listed in Table A such as nucleotide numbers 1-4 or 5-8 or 9-12 or 13-16 or 17-20 or 21-24 or 25-28 or 29-30 or 31-32 or 33. In some embodiments the nucleotides in Table B are selected from certain modified nucleotides listed in Table A such as nucleotide numbers 9-12 and 21-28, or 9-12 and 21-24, or 1-4 and 21-28, or 1-4 and 21-24, or 5-8 and 21-28, or 5-8 and 21-24. In some embodiments, the nucleotides in Table B are selected from one or two or three modified nucleotides listed in Table A such as nucleotide numbers 29-31 or 31-32 or 33. In some embodiments, the nucleotides in Table B are selected from certain modified nucleotides listed in Table A such as nucleotide numbers 29 or 31 or 33. The nucleotides in the Y domain of Table B can include nucleotides of Formula B.

In some embodiments, the oligonucleotide of Table B is conjugated at the 5' and/or 3' end to a ligand-targeting group and/or lipid moiety.

In some embodiments, the oligonucleotide compounds of the present disclosure include the following nucleobase sequences set forth in Table C.

TABLE C

| Nucleobase Sequences (5'-3') |
|---|
| 5'-GCTTTTACTGACCATGCGAG-3' (SEQ ID NO: 1) |

In embodiments, the oligonucleotide includes the sequence of SEQ ID NO: 1. In embodiments, the sequence of SEQ ID NO: 1 is modified according to at least one of the disclosed modifications. In embodiments, SEQ ID NO: 1 is modified having a thiophosphoramidate linkage and 2'-methoxyethoxy (2'MOE) modification in at least the first two nucleotides from the 5' and 3' ends of the oligonucleotide. In embodiments, SEQ ID NO: 1 is modified having a 2'MOE modification in at least the first three nucleotides from the 5' and 3' ends of the oligonucleotide. In embodiments, SEQ ID NO: 1 is modified having a 2'MOE modification in at least the first four nucleotides from the 5' and 3' ends of the oligonucleotide. In embodiments, SEQ ID NO: 1 is modified having a 2'MOE modification in at least the first five nucleotides from the 5' and 3' ends of the oligo-nucleotide. In embodiments, SEQ ID NO: 1 is modified having a 2'MOE modification in at least the first six nucleotides from the 5' and 3' ends of the oligonucleotide.

In some embodiments, the oligonucleotide comprising a sequence complementary to at least a portion of the MAPT gene sequence comprises a modified sequence in accordance with the modified sequence of Table D where X is independently in each instance a natural or an unmodified nucleobase or a modified nucleobase. In some embodiments, each X is independently selected from A, C, G, U, T, 2,6-diaminopurine, a 5-Me pyrimidine (e.g., 5-methylcytosine, 5-methyluracil), and a g-clamp. In embodiments, SEQ ID NO: 1 is modified in accordance with the modified sequences of Table D such that each X in Table D corresponds to each of the nucleobases of SEQ ID NO: 1.

TABLE D

| Modified Sequence (5'-3') |
|---|
| 5'-moeXnpsmoeXnpsmoeXnpsmoeXnpsmoeXnpsXpsXpsXpsXps XpsXpsXpsXpsXpsXpsmoeXnpsmoeXnpsmoeXnpsmoeXnpsmoe Xn-3' |
| 5'-moeGnpsmoeCnps(5m)moeUnps(5m)moeUnps(5m)moeUnps TpsApsCpsTpsGpsApsCpsCpsApsTpsmoeGnpsmoeCnpsmoe GnpsmoeAnpsmoeGn-3'-NPS Modified SEQ ID NO: 1 |

In embodiments, each of the nucleotides of a domain are modified. In embodiments, each of the nucleotides of a domain have the same modifications. In embodiments, each of the nucleotides of the X and Z domains are modified. In embodiments, each of the nucleotides of the X and Z domains have the same modifications. In embodiments, each of the nucleotides of a domain are modified with 2' MOE. In embodiments, each of the nucleotides of the X and Z domains are modified with 2' MOE. In embodiments, each of the nucleotides of a domain are modified with 2' OMe. In embodiments, each of the nucleotides of the X and Z domains are modified with 2' OMe. In embodiments, each of the nucleotides of a domain are modified with 2' OEt. In embodiments, each of the nucleotides of the X and Z domains are modified with 2' OEt. In embodiments, each of the nucleotides of the X and Z domains are linked by an NPS linkage. In embodiments, the X and Z domains have the same number of nucleotides. In embodiments, the X and Z domains each have 4-8 nucleotides. In embodiments, the X and Z domains each have 5-6 nucleotides. In embodiments, the X and Z domains each have 5 nucleotides. In embodiments, the Y domain has at least twice the number of nucleotides as each of the X and Z domains. In embodiments, the Y domain has 8-12 nucleotides. In embodiments, the Y domain has 10 nucleotides. In embodiments, each of the nucleotides of the Y domain are linked by a PS linkage.

In embodiments, at least one nucleobase of the oligonucleotide is modified. In embodiments, at least one nucleobase adjacent to the 3' terminal end of the oligonucleotide is modified. In embodiments, at least one nucleobase in the Z domain of the oligonucleotide is modified. In embodiments, at least one nucleobase in the Y domain of the oligonucleotide is modified.

Oligonucleotides of the present disclosure also include an oligonucleotide comprising a sequence that is at least 90% identical to a nucleobase sequence selected from the sequences listed in Table C, independent of the modifications of the sequences listed in Table B and D. In some embodiments, 1, 2, 3, 4, 5 nucleobases are different from the sequences listed in Table C, independent of the modifications of the sequences listed in Tables B and D.

In embodiments, the disclosed oligonucleotides display an increased affinity for a target nucleic acid sequence compared to an unmodified oligonucleotide of the same sequence. For example, in some sequences the disclosed oligonucleotide has a nucleobase sequence that is complementary or hybridizes to a target nucleic acid sequence at a higher affinity than an unmodified oligonucleotide of the same sequence. In embodiments, the disclosed oligonucleotide complexed with a complementary target nucleic acid sequence has a melting temperature (Tm) of >37° C. The complex may be formed under physiological conditions or nearly physiological conditions such as in phosphate-buffered saline (PBS). In embodiments, the Tm of the complex is >50° C. In embodiments, the Tm of the complex is 50-100° C. In embodiments, the Tm of a disclosed oligonucleotide duplexed with a target nucleic acid sequence under physiological conditions or nearly physiological conditions is >50° C.

In certain embodiments, the target nucleic acid sequence may be selected from a nucleic acid sequence of a known DNA or RNA sequence such as the MAPT gene. The MAPT gene may be a DNA or RNA sequence such as exon 5, exon 10 or exon 12.

In embodiments, the disclosed oligonucleotides display an affinity for at least a portion of the MAPT gene or its RNA equivalents, such as MAPT mRNA, and/or display stability complexed to at least a portion of the MAPT gene or its RNA equivalents. In embodiments, the oligonucleotide complexed with a complementary MAPT gene sequence has a melting temperature (Tm) of >37° C. The MAPT gene may include an RNA sequence such as exon 5, exon 10 or exon 12. The complex may be formed under physiological conditions or nearly physiological conditions such as in phosphate-buffered saline (PBS). In embodiments, the Tm of the complex is >50° C. In embodiments, the Tm of the complex is 50-100° C. In embodiments, the Tm of a disclosed oligonucleotide duplexed with the MAPT gene under physiological conditions or nearly physiological conditions is >50° C.

Compounds of the present disclosure include an oligonucleotide construct having a nucleobase sequence complimentary to at least a portion of the MAPT gene, the construct having the following Formula (VII):

5'-X'-Y'-Z'-3'  (VII)

wherein X'-Y'-Z' is a chimeric oligonucleotide comprising a sequence of 14 to 22 nucleosides, and is optionally conjugated at the 5' and/or 3' end to a ligand targeting group, X' is a domain comprising a sequence of modified nucleosides that is 3-14 nucleosides in length; Y' is a domain comprising a sequence of 2 to 4 2'-deoxynucleosides linked through intersubunit linkages; and Z' is a domain comprising a sequence of modified nucleosides that is 3-14 nucleosides in length, wherein the X' and/or Y' domains comprise one or more modified nucleoside which is linked through a N3'→P5' phosphoramidate or a N3'→P5' thiophosphoramidate intersubunit linkage.

The chimeric oligonucleotide represented by X'-Y'-Z' of Formula (VII) comprises a sequence of 14 to 22 nucleotides, for example, 14, 15, 16, 17, 18, 19, 20, 21, or 22 nucleotides. In some embodiments, the number of nucleotides in each of X', Y' and Z', respectively is: 8/2/10, 9/2/10, 10/2/10, 7/3/10, 8/3/10, 9/3/10, 8/4/8, 9/4/9, 6/4/8. In some embodiments, X' is 6-10, Y' is 2-4 and Z' is 8-10.

In some embodiments, the compound of Formula (VII) consists of the X'-Y'-Z' chimeric oligonucleotide consisting of a sequence of 14 to 22 nucleotides, and is optionally conjugated at the 5' and/or 3' end (e.g., 5' end, 3' end or both 5' and 3' ends) to a ligand targeting group, where X' is a domain consisting of a sequence containing one or more modified nucleotides that is 3-10 nucleotides in length; Z' is a domain consisting of a sequence containing one or more modified nucleotides that is 3-10 nucleotides in length; and Y' is a domain consisting of a sequence of 2 to 4 2'-deoxynucleotides linked through thiophosphate intersubunit linkages and optionally one phosphodiester intersubunit linkage, wherein the X' and/or Y' domains contain one or more modified nucleotide which is linked through a N3'→P5' phosphoramidate or a N3'→P5' thiophosphoramidate intersubunit linkage.

The X' domain comprises a sequence of modified nucleotides, where the X' domain is 4-10 nucleotides in length. For example, the X' domain may comprise a sequence of 4, 5, 6, 7, 8, 9, or 10 nucleotides. One or more (e.g., 1, 2, 3, 4, 5, 6, 7, 8, 9, 10, 11, 12, 13, 14, 15, 16, 17, 18, 19, 20, 21 or 22) of these nucleotides is modified. For example, in some embodiments, all the nucleotides in the X' domain are modified.

The modified nucleotides of the X' domain may be the same as disclosed for X in Formula (VI) or (VI'). For example, the nucleotides of the X' domain may be modified with respect to one or more of their nucleobases, the 2' and/or 3' positions on the ribose sugar and their intersubunit linkages. Embodiments include wherein the 2' position is modified with an F (ribo or arabino) and the 3' position is O or NH. Embodiments also include wherein the 2' position is modified with an OMe and the 3' position is O or NH. Embodiments include wherein the 2' position is modified with an F (ribo or arabino) as well as Me or OMe, and the 3' position is O or NH. Embodiments include wherein the 2' position is modified with an F (ribo or arabino) and the 3' position is O or NH. Embodiments include wherein the 2' position is modified with an O-methoxyethoxy and the 3' position is O or NH. Embodiments also include wherein the 2' position is modified with an F (ribo or arabino) and the 3' position is O or NH. Embodiments include wherein the 2' and 4' positions are modified bridging group (as described elsewhere herein) to form a conformationally restricted nucleotide and the 3' position is O or NH. Each of these embodiments may include thiophosphate (or thiophosphoramidate depending on the 3' substitution) and phosphoramidate intersubunit linkages.

Embodiments also include where the 2' position is OH, and the 3' position is NH, or where the 2' position is H, and the 3' position is NH. Each of these embodiments may include thiophosphoramidate and/or phosphoramidate intersubunit linkages.

The nucleotides of the X' domain are linked through intersubunit linkages, for example, N3'→P5' phosphoramidate, N3'→P5' thiophosphoramidate, thiophosphate or phosphodiester intersubunit linkages. In some embodiments, the X' domain is linked through intersubunit linkages selected from N3'→P5' phosphoramidate, N3'→P5' thiophosphoramidate, and combinations thereof. In some embodiments, the X' domain comprises at least 1, 2, 3, 4, 5, 6, 7, 8, 9 or 10 from N3'→P5' phosphoramidate and/or N3'→P5' thiophosphoramidate intersubunit linkages.

The Y' domain comprises a sequence of 2 to 4 2'-deoxynucleotides. For example, the Y' domain may comprise a sequence of 2, 3, or 4 2'-deoxynucleotides. One or more of the 2'-deoxynucleotides may be linked through thiophosphate or phosphodiester intersubunit linkages (e.g., 1, 2, 3, 4, 5, 6, 7, 8, 9, 10, 11, 12, 13, 14, 15, 16, 17, 18, 19, 20, 21 or 22). In some embodiments, each of the 2'-deoxynucleotides is linked through a thiophosphate intersubunit linkage. In other embodiments, each of the 2'-deoxynucleotides is linked through a phosphodiester intersubunit linkage. In other embodiments, the Y' domain consists of 2'-deoxynucleotides linked through thiophosphate intersubunit linkages, and optionally one phosphodiester intersubunit linkage.

The Z' domain comprises a sequence of modified nucleotides, where the Z' domain is 4-10 nucleotides in length. For example, the Z' domain may comprise a sequence of 4, 5, 6, 7, 8, 9, or 10 nucleotides. One or more of these nucleotides is modified (e.g., 1, 2, 3, 4, 5, 6, 7, 8, 9, 10, 11, 12, 13, 14, 15, 16, 17, 18, 19, 20, 21 or 22). For example, in some embodiments, all the nucleotides in the Z' domain are modified.

The modified nucleotides of the Z' domain may be the same as disclosed for Z in Formula (VI) or (VI'). For example, the nucleotides of the Z' domain may be modified with respect to one or more of their nucleobases, the 2' and/or 3' positions on the ribose sugar and their intersubunit linkages. Embodiments include wherein the 2' position is modified with an F (ribo or arabino) and the 3' position is O or NH. Embodiments also include wherein the 2' position is modified with an OMe and the 3' position is O or NH. Embodiments include wherein the 2' position is modified with an F (ribo or arabino) as well as Me or OMe, and the 3' position is O or NH. Embodiments include wherein the 2' position is modified with an F (ribo or arabino) and the 3' position is O or NH. Embodiments include wherein the 2' position is modified with an O-methoxyethoxy and the 3' position is O or NH. Embodiments also include wherein the 2' position is modified with an F (ribo or arabino) and the 3' position is O or NH. Embodiments include wherein the 2' and 4' positions are modified bridging group (as described elsewhere herein) to form a conformationally restricted nucleotide and the 3' position is O or NH. Each of these embodiments may include thiophosphate (or thiophosphoramidate depending on the 3' substitution) and phosphoramidate intersubunit linkages.

Embodiments also include oligonucleotides comprising nucleotides where the 2' position is OH, and the 3' position is NH, or where the 2' position is H, and the 3' position is NH. Each of these embodiments may include thiophosphoramidate and/or phosphoramidate intersubunit linkages.

The nucleotides of the Z' domain are linked through intersubunit linkages, for example, N3'→P5' phosphoramidate, N3'→P5' thiophosphoramidate, thiophosphate or phosphodiester intersubunit linkages. In some embodiments, the Z' domain is linked through intersubunit linkages selected from N3'→P5' phosphoramidate, N3'→P5' thiophosphoramidate, and combinations thereof. In some embodiments, the Z' domain comprises at least 1, 2, 3, 4, 5, 6, 7, 8, 9 or 10 from N3'→P5' phosphoramidate and/or N3'→P5' thiophosphoramidate intersubunit linkages.

Additional embodiments include an oligonucleotide comprising:
(A) one or more nucleotides of the following formula:

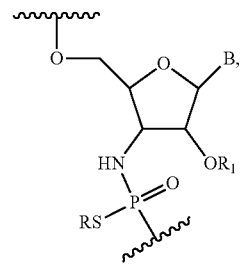

wherein R is H or a positively charged counter ion, B is a nucleobase, $R_1$ is —$(CH_2)_2OCH_3$ or —$OCH_3$ and
(B) a domain comprising a sequence of 2 to 10 2'-deoxynucleosides linked through thiophosphate intersubunit linkages. In some embodiments, the oligonucleotide includes 20 nucleotides. In some embodiments, the oligonucleotide includes a domain comprising a sequence of 10 2'-deoxynucleosides linked through thiophosphate intersubunit linkages.

Modified Antisense Oligonucleotides

Other compounds include modified antisense oligonucleotides. In some embodiments the ASO includes the nucleotide of formula (I), (II), (IIIa), (IIIb), (IV), (V) and/or (V').

Other compounds of the present disclosure include an oligonucleotide having a nucleobase sequence complimentary to at least a portion of the MAPT gene, the oligonucleotide comprising at least one nucleotide having the following Formula (VIII):

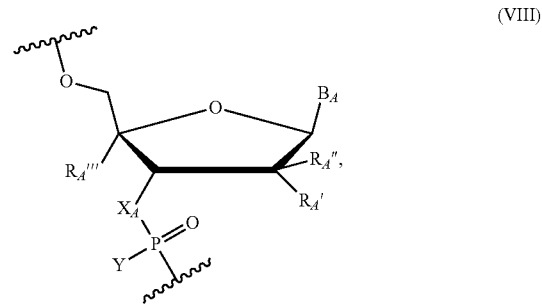

(VIII)

wherein $X_A$ is NH or O, Y is OR SR, where R is H or a positively charged counter ion, $B_A$ is independently in each instance a natural or an unmodified nucleobase or a modified nucleobase, $R_A'$ and $R_A''$ are each independently in each instance selected from H, F, OH, OMe, O-methoxyethoxy, and $R_A'''$ is H or $R_A'$ and $R_A'''$ together form —O—$CH_2$—, —O—CH(Me)- or —O—$(CH_2)_2$—.

In some embodiments, $R_A'$ and $R_A'''$ are H; and $R_A''$ is selected from F, OH, OMe, Me, O-methoxyethoxy. In other embodiments, $R_A''$ and $R_A'''$ are H; and $R_A'$ is selected from F, OMe, Me, O-methoxyethoxy. In some embodiments, $X_A$ is NH in each instance.

Some embodiments include one or more modified nucleotides represented by Formula (VIII), wherein $X_A$ is NH; $B_A$ is a G-clamp; $R_A'$ is F or OMe and $R_A''$ is H; or $R_A'$ is H and $R_A''$ is H or F; and $R_A'''$ is H.

Some embodiments include one or more modified nucleotides represented by Formula (VIII), wherein $X_A$ is NH; $B_A$ is an unmodified or modified nucleobase; $R_A'$ and $R_A'''$ together form a conformationally restricted nucleotide (e.g., —O—CH$_2$— or —O—(CH$_2$)$_2$—); and $R_A''$ is H. In some embodiments, $B_A$ is an unmodified or a modified nucleobase selected from the group consisting of 5-methylcytosine, 2,6-diaminopurine, and 5-methyluracil.

Some embodiments include one or more modified nucleotides represented by Formula (VIII), wherein $X_A$ is NH; B is an unmodified or modified nucleobase; $R_A'$ is F or OMe, $R_A''$ is H and $R_A'''$ is H.

Some embodiments include one or more modified nucleotides represented by Formula (VIII), wherein $X_A$ is NH; $B_A$ is an unmodified or modified nucleobase; $R_A'$ is H, $R_A''$ is F and $R_A'''$ is H.

In some embodiments, $X_A$ is NH. In other embodiments, Y is O⁻ or S⁻ (with a positively charged counter ion). In some embodiments, $R_A'$ or $R_A''$ is H and the other is F, OH, OMe, Me, O-methoxyethoxy (e.g. arabino-F or ribo-F or OMe).

In some embodiments, $B_A$ is selected from A, C, G, U and T. In additional embodiments, $B_A$ is selected from A, C, G, U, T, 2,6-diaminopurine, a 5-Me pyrimidine (e.g., 5-methylcytosine, 5-methyluracil). In some embodiments, at least one of $R_A'$ and $R_A''$ is H. For example, in some embodiments, $R_A'$ is F, OH, OMe, Me, O-methoxyethoxy and $R_A''$ is H. In other embodiments, $R_A'$ is H and $R_A''$ is F.

In some embodiments, when $B_A$ is a purine nucleobase at least one of $R_A'$ and $R_A''$ is OH or F, and/or when $B_A$ is a pyrimidine nucleobase at least one of $R_A'$ and $R_A''$ is OMe, OH or F.

In other embodiments, the nucleotides include one or more of the nucleotides in Table E or Table F.

TABLE E

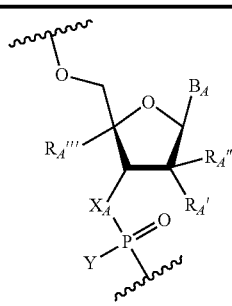

| Nucleotide No. | R' | R'' | R''' | A | W |
|---|---|---|---|---|---|
| 48 | F | H | H | NH | S |
| 49 | F | H | H | NH | O |
| 50 | F | H | H | O | S |
| 51 | F | H | H | O | O |
| 52 | H | F | H | NH | S |
| 53 | H | F | H | NH | O |
| 54 | H | F | H | O | S |
| 55 | H | F | H | O | O |
| 56 | OMe | H | H | NH | S |
| 57 | OMe | H | H | NH | O |
| 58 | OMe | H | H | O | S |
| 59 | OMe | H | H | O | O |
| 60 | H | F | H | NH | S |
| 61 | H | F | H | NH | O |
| 62 | H | F | H | O | S |
| 63 | H | F | H | O | O |
| 64 | O-methoxyethoxy | H | H | NH | S |
| 65 | O-methoxyethoxy | H | H | NH | O |
| 66 | O-methoxyethoxy | H | H | O | S |

TABLE E-continued

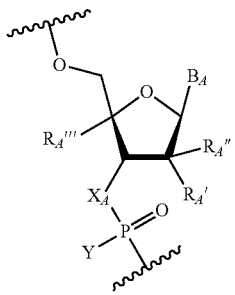

| Nucleotide No. | R' | R'' | R''' | A | W |
|---|---|---|---|---|---|
| 67 | O-methoxyethoxy | H | H | O | O |
| 68 | H | H | H | NH | S |
| 69 | H | H | H | NH | O |
| 70 | OH | H | H | NH | S |
| 71 | OH | H | H | NH | O |
| 72 | OH | H | H | O | S |
| 73 | H | OH | H | NH | O |
| 74 | H | OH | H | NH | S |
| 75 | H | OEt | H | NH | O |
| 76 | H | OEt | H | NH | S |
| 77 | H | OEt | H | O | O |
| 78 | H | OEt | H | O | S |
| 79 | OEt | H | H | NH | O |
| 80 | OEt | H | H | NH | S |
| 81 | OEt | H | H | O | O |
| 82 | OEt | H | H | O | S |

TABLE F

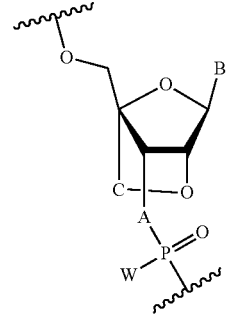

| Nucleotide No. | C | A | W |
|---|---|---|---|
| 83 | —O—CH$_2$— | NH | S |
| 84 | —O—CH$_2$— | NH | O |
| 85 | —O—CH$_2$— | O | S |
| 86 | —O—CH$_2$— | O | O |
| 87 | —O—(CH$_2$)$_2$— | NH | S |
| 88 | —O—(CH$_2$)$_2$— | NH | O |
| 89 | —O—(CH$_2$)$_2$— | O | S |
| 90 | —O—(CH$_2$)$_2$— | O | O |
| 91 | —O—CH(Me)— | NH | S |
| 92 | —O—CH(Me)— | NH | O |
| 93 | —O—CH(Me)— | O | S |
| 94 | —O—CH(Me)— | O | O |

Compounds of the present disclosure also include an oligonucleotide having a nucleobase sequence complimentary to at least a portion of the MAPT gene, the oligonucleotide comprising at least ten nucleotides having the following Formula (IX):

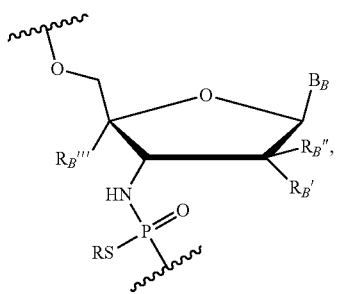

(IX)

wherein R is H or a positively charged counter ion, $B_B$ is independently in each instance a natural or an unmodified nucleobase or a modified nucleobase, $R_B'$ and $R_B''$ are each independently in each instance selected from H, F, OMe, O-methoxyethoxy, and $R_B'''$ is H or $R_B'$ and $R_B'''$ together form —O—CH$_2$—, —O—CH(Me)-, or —O—(CH$_2$)$_2$—.

In some embodiments, every oligonucleotide is a nucleotide of the Formula (IX).

In some embodiments, $R_B'$ and $R_B'''$ are H and $R_B''$ is selected from F, OH, OMe, Me, O-methoxyethoxy. In other embodiments, $R_B''$ and $R_B'''$ are H; and $R_B'$ is selected from F, OMe, Me, O-methoxyethoxy.

Some embodiments include one or more modified nucleotides represented by Formula (IX), wherein $B_A$ is a G-clamp; $R_B'$ is F or OMe and $R_B''$ is H; or $R_B'$ is H and $R_B''$ is H or F; and $R_B'''$ is H.

Some embodiments include one or more modified nucleotides represented by Formula (IX), wherein $B_A$ is an unmodified or modified nucleobase; $R_B'$ and $R_B'''$ together form a conformationally restricted nucleotide (e.g., —O—CH$_2$— or —O—(CH$_2$)$_2$—); and $R_B''$ is H. In some embodiments, $B_A$ is an unmodified or a modified nucleobase selected from the group consisting of 5-methylcytosine, 2,6-diaminopurine, and 5-methyluracil.

Some embodiments include one or more modified nucleotides represented by Formula (IX), wherein B is an unmodified or modified nucleobase; $R_B'$ is F or OMe, $R_B''$ is H and $R_B'''$ is H.

Some embodiments include one or more modified nucleotides represented by Formula (IX), wherein $B_A$ is an unmodified or modified nucleobase; $R_B'$ is H, $R_B''$ is F and $R_B'''$ is H.

In other embodiments, Y is S$^-$ (with a positively charged counter ion). In some embodiments, $R_B'$ or $R_B''$ is H and the other is F, OH, OMe, Me, O-methoxyethoxy (e.g. arabino-F or ribo-F or OMe).

In some embodiments, $B_B$ is selected from A, C, G, U and T. In additional embodiments, $B_B$ is selected from A, C, G, U, T, 2,6-diaminopurine, a 5-Me pyrimidine (e.g., 5-methylcytosine). In some embodiments, at least one of $R_B'$ and $R_B''$ is H. For example, in some embodiments, $R_A'$ is F, OH, OMe, Me, O-methoxyethoxy and $R_B''$ is H. In other embodiments, $R_B'$ is H and $R_B''$ is F.

In some embodiments, when $B_B$ is a purine nucleobase at least one of $R_B'$ and $R_B''$ is OH or F, and/or when $B_B$ is a pyrimidine nucleobase at least one of $R_B'$ and $R_B''$ is OMe, OH or F.

In some embodiments, the nucleobase sequence of the oligonucleotide of Formulae (VIII) or (IX) comprises a sequence selected from those in Table A. In some embodiments, the nucleobase sequence of the oligonucleotide of Formulae (VIII) or (IX) comprises a sequence 1, 2, 3, 4, or 5 nucleobases different from a sequence selected from those in Table D.

In embodiments, the disclosed oligonucleotides display an affinity for at least a portion of the MAPT gene or its RNA equivalents and/or display stability complexed to at least one of the following six sequences of at least a portion of the MAPT gene or its RNA equivalents. In embodiments, the oligonucleotide complexed with a complementary MAPT gene sequence has a melting temperature (Tm) of >37° C. The MAPT gene may be an RNA sequence such as exon 5, exon 10 or exon 12. The complex may be formed under physiological conditions or nearly physiological conditions such as in phosphate-buffered saline (PBS). In embodiments, the Tm of the complex is >50° C. In embodiments, the Tm of the complex is 50-100° C. In embodiments, the Tm of a disclosed oligonucleotide duplexed with at least a portion of the MAPT gene under physiological conditions or nearly physiological conditions is >50° C.

In some aspects of the disclosure, the nucleobase sequence of the oligonucleotide of Formula (VIII) or (IX) comprises a sequence of 12-22 nucleotides, for example, 14-20 nucleotides or 16-19 nucleotides. In some embodiments, the nucleobase sequence of the oligonucleotide of Formula (VIII) or (IX) is 12, 13, 14, 15, 16, 17, 18, 19, 20, 21 or 22 nucleotides in length.

In another aspect of the disclosure, the oligonucleotides described herein are conjugated or modified at one or more ends of the oligonucleotide.

For example, in some embodiments, a terminal end of the oligonucleotide is protected from hydrolytic cleavage by at least one modified nucleotide at said terminal end. In some embodiments, the modified nucleotide is a modified nucleotide comprising a modified nucleotide comprising a 3'-N modification and may include a thiophosphoramidate subunit linkage. In some embodiments, the oligonucleotides of Formulae (VIII) and (IX) further comprise at least one nucleotide (e.g. 1 or 2) at the 3' and/or 5' end that contains a thiophosphate intersubunit linkage and a thymine nucleobase. In some embodiments, the oligonucleotides of Formulae (VIII) and (IX) further comprise at least one nucleotide (e.g. 1 or 2) at the 3' and/or 5' end that contains a 2'-OMe modified nucleotide and a thymine nucleobase. In some embodiments, the oligonucleotides of Formulae (VIII) and (IX) further comprise at least one 2'-OMe modified nucleotide at the 3' and/or 5' end that contains a thiophosphate intersubunit linkage and an uracil nucleobase. In some embodiments, an inverted dT can be incorporated at the 3'-end of the oligonucleotides of Formulae (VIII) and (IX), leading to a 3'-3' linkage which may inhibit degradation by 3' exonucleases and/or extension by DNA polymerases.

Conjugated Oligonucleotides

The present disclosure is also directed to additional components conjugated to the oligonucleotide such as targeting moieties and oligonucleotides modified at one or more ends.

In some embodiments, the oligonucleotides described herein are conjugated to one or more ligand targeting group, optionally through a linking moiety, such as a HEG linker or a C6 or C7 amino linker. In some embodiments, oligonucleotides described herein further comprises a ligand targeting group conjugated at the 5' and/or 3' end through an optional linker. In preferred embodiments, the oligonucleotides described herein further comprise a ligand-targeting group conjugated at the 5' and/or 3' end through an optional linker. In some embodiments, the conjugation is at the 3'-end of the oligonucleotides described herein.

In some embodiments, the ligand-targeting group enhances the activity, cellular distribution or cellular uptake of the oligonucleotide by a particular type of cell such as CNS cells.

In some embodiments, the ligand targeting group may be a lipid moiety such as tocopherols and fatty acids such as hexadecanoic acids (palmitic acid) and octanoic acids such as dithiooctanoic acid (lipoic acid), a palmitoyl moiety.

In some embodiments, a terminal end of the oligonucleotide is protected from hydrolytic cleavage by at least one modified nucleotide at the terminal end. In some embodiments, the modified nucleotide is a modified nucleotide comprising a modified nucleotide comprising a 3'-N modification and may include a thiophosphoramidate subunit linkage. In some embodiments, the oligonucleotide strand further comprises at least one nucleotide (e.g. 1 or 2) at the 3' and/or 5' end that contains a thiophosphate intersubunit linkage and a thymine nucleobase. In some embodiments, the oligonucleotide strand further comprises at least one nucleotide (e.g. 1 or 2) at the 3' and/or 5' end that contains a 2'-F, 2'-OMe, 2'-OEt, or 2'-MOE modified nucleotide. In some embodiments, the oligonucleotide strand further comprises at least one 2'-OMe modified nucleotide at the 3' and/or 5' end that contains a thiophosphate intersubunit linkage and an uracil nucleobase. In embodiments, the 3' end of the ASO is attached through an np or po linkage to a C6 amino linker further linked to a targeting moiety.

In some embodiments, an inverted dT can be incorporated at the 3'-end of the oligonucleotide strand, leading to a 3'-3' linkage that may inhibit degradation by 3' exonucleases and/or extension by DNA polymerases.

2. Compositions

The present disclosure also encompasses pharmaceutical compositions comprising oligonucleotides of the present disclosure. One embodiment is a pharmaceutical composition comprising an oligonucleotide of Formula (I), (II), (III), (IV), (V), or (VI), or other oligonucleotide of the present disclosure and a pharmaceutically acceptable diluent or carrier.

In some embodiments, the pharmaceutical composition containing the oligonucleotide of the present disclosure is formulated for delivery to the central nervous system (CNS) such as intrathecal or intracerebroventricular delivery. In other embodiments, the pharmaceutical composition containing the oligonucleotide of the present disclosure is formulated for systemic administration via parenteral delivery. Parenteral administration includes intravenous, intra-arterial, subcutaneous, intraperitoneal or intramuscular injection or infusion; also, subdermal administration, e.g., via an implanted device. In a preferred embodiment, the pharmaceutical composition containing the oligonucleotide of the present disclosure is formulated for intrathecal or intracerebroventricular delivery. Formulations for CNS administration may include sterile aqueous suspension, which may also contain buffers, diluents and other pharmaceutically acceptable additives as understood by the skilled artisan.

The pharmaceutical compositions containing the oligonucleotide of the present disclosure are useful for treating a disease or disorder, e.g., associated with the expression or activity of an AD gene.

3. Methods of Use

One aspect of the present technology includes methods for treating a subject diagnosed as having, suspected as having, or at risk of having tauopathy such as Alzheimer's disease (AD) and/or any other tau-related disorder. In therapeutic applications, compositions comprising the oligonucleotides of the present disclosure are administered to a subject suspected of, or already suffering from tauopathy such as AD and/or any tauopathy-related disorder in an amount sufficient to cure, or at least partially arrest, the symptoms of the disease, including its complications and intermediate pathological phenotypes in development of the tauopathy.

In some embodiments the oligonucleotides of the present disclosure show affinity to tau cDNA sequences including an exon and/or an intronic region. In some embodiments the oligonucleotides of the present disclosure show affinity to microglial targets such as PLCG2, CD33, TREM2) or astroglial targets such as ApoE as well as other neuronal targets such as APP. In some embodiments the oligonucleotides of the present disclosure show affinity to at least one of the following regions of the MAPT gene in Table G.

Table G

| Region | Targeted MAPT gene sequences | Tau Proteins Affected |
|---|---|---|
| Exon 5 | CTCGCATGGTCAGTAAAAGCA (SEQ ID NO: 45) | All 8 isoforms: NP_058519.3, NP_005901.2, NP_058518.1, NP_058525.1, NP_001116539.1, NP_00116538.2, NP_001 190180.1, NP_001190181.1 |
| Exon 5 | GGAAGCGATGACAAAAAAGCA (SEQ ID NO: 46) | All 8 isoforms: NP_058519.3, NP_005901.2, NP_058518.1, NP_058525.1, NP_001116539.1, NP_001165382, NP_001190180.1, NP_001190181.1 |
| Exon 10 | GGCTCAAAGGATAATATCAAA (SEQ ID NO: 47) | All 8 isoforms: NP_058519.3, NP_005901.2, NP_058518.1, NP_058525.1, NP_001116539.1, NP_00116538.2, NP_001190180.1, NP_001190181.1 |
| Exon 12 | GGTCCCTGGACAATATCACC (SEQ ID NO: 48) | All 8 isoforms: NP_058519.3, NP_005901.2, NP_058518.1, NP_058525.1, NP_001116539.1, NP_001165382, NP_001190180.1, NP_001190181.1 |

In an embodiment, the nucleotides of the present disclosure show affinity to exon 10 or exon 12 of Tau mRNA.

In another general aspect, the present disclosure relates to a method of treating or reducing symptoms of a disease, disorder or condition, such as a tauopathy, in a subject in need thereof, comprising administering to the subject a pharmaceutical composition of the present disclosure.

In another general aspect, the present disclosure relates to a method of reducing pathological tau aggregation or spreading of tauopathy in a subject in need thereof, comprising administering to the subject a pharmaceutical composition of the present disclosure.

According to embodiments of the present disclosure, the pharmaceutical composition comprises a therapeutically effective amount of an oligonucleotide of the present disclosure. As used herein with reference to oligonucleotides of the present disclosure, a therapeutically effective amount means an amount of the oligonucleotides of the present disclosure that results in treatment of a disease, disorder, or condition; prevents or slows the progression of the disease, disorder, or condition; or reduces or completely alleviates symptoms associated with the immune disease, disorder, or condition.

According to particular embodiments, a therapeutically effective amount refers to the amount of therapy which is sufficient to achieve one, two, three, four, or more of the following effects: (i) reduce or ameliorate the severity of the disease, disorder or condition to be treated or a symptom associated therewith; (ii) reduce the duration of the disease, disorder or condition to be treated, or a symptom associated therewith; (iii) prevent the progression of the disease, disorder or condition to be treated, or a symptom associated therewith; (iv) cause regression of the disease, disorder or condition to be treated, or a symptom associated therewith; (v) prevent the development or onset of the disease, disorder or condition to be treated, or a symptom associated therewith; (vi) prevent the recurrence of the disease, disorder or condition to be treated, or a symptom associated therewith; (vii) reduce hospitalization of a subject having the disease, disorder or condition to be treated, or a symptom associated therewith; (viii) reduce hospitalization length of a subject having the disease, disorder or condition to be treated, or a symptom associated therewith; (ix) increase the survival of a subject with the disease, disorder or condition to be treated, or a symptom associated therewith; (xi) inhibit or reduce the disease, disorder or condition to be treated, or a symptom associated therewith in a subject; and/or (xii) enhance or improve the prophylactic or therapeutic effect(s) of another therapy.

According to particular embodiments, the disease, disorder or condition to be treated is a tauopathy. According to more particular embodiments, the disease, disorder or condition to be treated, includes, but is not limited to, familial Alzheimer's disease, sporadic Alzheimer's disease, frontotemporal dementia with parkinsonism linked to chromosome 17 (FTDP-17), progressive supranuclear palsy, corticobasal degeneration, Pick's disease, progressive subcortical gliosis, tangle only dementia, diffuse neurofibrillary tangles with calcification, argyrophilic grain dementia, amyotrophic lateral sclerosis parkinsonism-dementia complex, Down syndrome, Gerstmann-Straussler-Scheinker disease, Hallervorden-Spatz disease, inclusion body myositis, Creutzfeld-Jakob disease, multiple system atrophy, Niemann-Pick disease type C, prion protein cerebral amyloid angiopathy, subacute sclerosing panencephalitis, myotonic dystrophy, non-Guamanian motor neuron disease with neurofibrillary tangles, postencephalitic parkinsonism, chronic traumatic encephalopathy, or dementia pugulistica (boxing disease).

A tauopathy-related behavioral phenotype includes, but is not limited to, cognitive impairments, early personality change and disinhibition, apathy, abulia, mutism, apraxia, perseveration, stereotyped movements/behaviors, hyperorality, disorganization, inability to plan or organize sequential tasks, selfishness/callousness, antisocial traits, a lack of empathy, halting, agrammatic speech with frequent paraphasic errors but relatively preserved comprehension, impaired comprehension and word-finding deficits, slowly progressive gait instability, retropulsions, freezing, frequent falls, non-levodopa responsive axial rigidity, supranuclear gaze palsy, square wave jerks, slow vertical saccades, pseudobulbar palsy, limb apraxia, dystonia, cortical sensory loss, and tremor.

Patients amenable to treatment include, but are not limited to, asymptomatic individuals at risk of AD or other tauopathy, as well as patients presently showing symptoms. Patients amenable to treatment include individuals who have a known genetic risk of AD, such as a family history of AD or presence of genetic risk factors in the genome. Exemplary risk factors are mutations in the amyloid precursor protein (APP), especially at position 717 and positions 670 and 671 (Hardy and Swedish mutations, respectively). Other risk factors are mutations in the presenilin genes PS1 and PS2 and in ApoE4, family history of hypercholesterolemia or atherosclerosis. Individuals presently suffering from AD can be recognized from characteristic dementia by the presence of risk factors described above. In addition, a number of diagnostic tests are available to identify individuals who have AD. These include measurement of cerebrospinal fluid tau and Abeta 42 levels. Elevated tau and decreased Abeta 42 levels signify the presence of AD. Individuals suffering from AD can also be diagnosed by AD and Related Disorders Association criteria.

Oligonucleotides of the present disclosure are suitable both as therapeutic and prophylactic agents for treating or preventing neurodegenerative diseases that involve pathological aggregation of tau, such as AD or other tauopathies. In asymptomatic patients, treatment can begin at any age (e.g., at about 10, 15, 20, 25, 30 years). Usually, however, it is not necessary to begin treatment until a patient reaches about 40, 50, 60, or 70 years. Treatment typically entails multiple dosages over a period of time.

In prophylactic applications, pharmaceutical compositions or medicaments are administered to a patient susceptible to, or otherwise at risk of, AD in an amount sufficient to eliminate or reduce the risk, lessen the severity, or delay the outset of the disease, including biochemical, histologic and/or behavioral symptoms of the disease, its complications and intermediate pathological phenotypes presented during development of the disease. In therapeutic applications, compositions or medicaments are administered to a patient suspected of, or already suffering from, such a disease in an amount sufficient to reduce, arrest, or delay any of the symptoms of the disease (biochemical, histologic and/or behavioral). Administration of a therapeutic can reduce or eliminate mild cognitive impairment in patients that have not yet developed characteristic Alzheimer's pathology.

The therapeutically effective amount or dosage can vary according to various factors, such as the disease, disorder or condition to be treated, the means of administration, the target site, the physiological state of the subject (including, e.g., age, body weight, health), whether the subject is a human or an animal, other medications administered, and whether the treatment is prophylactic or therapeutic. Treatment dosages are optimally titrated to optimize safety and efficacy.

The oligonucleotides of the present disclosure can be prepared as pharmaceutical compositions containing a therapeutically effective amount of the oligonucleotides of the present disclosure as an active ingredient in a pharmaceutically acceptable carrier. The carrier can be liquids, such as water and oils, including those of petroleum, animal, vegetable or synthetic origin, such as peanut oil, soybean oil, mineral oil, sesame oil and the like. For example, 0.4% saline and 0.3% glycine can be used. These solutions are sterile and generally free of particulate matter. They can be sterilized by conventional, well-known sterilization techniques (e.g., filtration). The compositions can contain pharmaceutically acceptable auxiliary substances as required to approximate physiological conditions such as pH adjusting and buffering agents, stabilizing, thickening, lubricating and coloring agents, etc. The concentration of the oligonucleotides of the present disclosure in such pharmaceutical formulation can vary widely, i.e., from less than about 0.5%, usually at or at least about 1% to as much as 15 or 20% by weight and will be selected primarily based on required dose, fluid volumes, viscosities, etc., according to the particular mode of administration selected.

The mode of administration for therapeutic use of the oligonucleotides of the present disclosure can be any suitable route that delivers the agent to the host. For example, the compositions described herein can be formulated to be suitable for parenteral administration, e.g., intradermal, intramuscular, intraperitoneal, intravenous, subcutaneous, intranasal or intracranial administration, or they can be administered into the cerebrospinal fluid of the brain or spine.

In some embodiments the injectable formulation in accordance with the present disclosure may be administered directly to the central nervous system (CNS). As herein defined the term "central nervous system" is defined as the part of the nervous system which in vertebrates consists of the brain and spinal cord, to which sensory impulses are transmitted and from which motor impulses pass out, and which coordinates the activity of the entire nervous system.

Examples of direct administration into the CNS include intrathecal (IT) administration, and direct administration into the brain, such as intra-cerebral (IC), intra-ventricular, intra-cerebroventricular (ICV), intra-cranial or subdural routes of administration. Such routes of administration may be particularly beneficial for diseases affecting the central nervous system.

Thus, in certain aspects and embodiments of the present disclosure the non-systemic administration is selected from the group consisting of intrathecal, intra-cerebral, intra-ventricular, intra-cerebroventricular, intracranial, and subdural administration.

In some embodiments the non-systemic administration as herein defined is intrathecal administration. As known to a skilled artisan the term "intrathecal administration" refers to the introduction of a therapeutic substance by injection into the subarachnoid space of the spinal cord, while bypassing the blood-brain barrier.

In other embodiments the non-systemic administration as herein defined is intra-cerebroventricular administration.

As known in the art, the ventricular system is a set of four interconnected cavities (ventricles) in the brain, where the cerebrospinal fluid (CSF) is produced. Within each ventricle there is a region of choroid plexus, a network of ependymal cells involved in the production of CSF. The ventricular system is continuous with the central canal of the spinal cord allowing for flow of CSF to circulate.

Despite the protective role that blood brain barrier plays in shielding the brain, it limits access to the central nervous system (CNS) of potential therapeutics designed for neurodegenerative disorders. Neurodegenerative diseases such as but not limited to Alzheimer's disease can benefit greatly from introducing the therapeutic agents directly into the CNS. One of the direct routes of administration into the CNS is injecting directly into cerebral lateral ventricles, by intracerebroventricular administration, which results in delivery of materials into the CNS through the cerebrospinal fluid.

Therefore as known in the art and as used herein the term "intra-cerebroventricular administration" refers to injecting directly into cerebral lateral ventricles.

The term "injection" or "injectable" as used herein refers to a bolus injection (administration of a discrete amount of an agent for raising its concentration in a bodily fluid), slow bolus injection over several minutes, or prolonged infusion, or several consecutive injections/infusions that are given at spaced apart intervals.

The treatment can be given in a single dose schedule, or as a multiple dose schedule in which a primary course of treatment can be with 1-10 separate doses, followed by other doses given at subsequent time intervals required to maintain and or reinforce the response, for example, at 1-4 months for a second dose, and if needed, a subsequent dose(s) after several months. Examples of suitable treatment schedules include: (i) 0, 1 month and 6 months, (ii) 0, 7 days and 1 month, (iii) 0 and 1 month, (iv) 0 and 6 months, or other schedules sufficient to elicit the desired responses expected to reduce disease symptoms or reduce severity of disease.

According to particular embodiments, a composition used in the treatment of a tauopathy can be used in combination with other agents that are effective for treatment of related neurodegenerative diseases. In the case of AD, oligonucleotides of the present disclosure can be administered in combination with agents that reduce or prevent the deposition of amyloid-beta (Abeta). It is possible that PHF-tau and Abeta pathologies are synergistic. Therefore, combination therapy targeting the clearance of both PHF-tau and Abeta and Abeta-related pathologies at the same time can be more effective than targeting each individually. In the case of Parkinson's Disease and related neurodegenerative diseases, immune modulation to clear aggregated forms of the alpha-synuclein protein is also an emerging therapy. A combination therapy which targets the clearance of both tau and alpha-synuclein proteins simultaneously can be more effective than targeting either protein individually.

In another general aspect, the present disclosure relates to a method of producing a pharmaceutical composition comprising an oligonucleotide of the present disclosure, comprising combining the oligonucleotide with a pharmaceutically acceptable carrier to obtain the pharmaceutical composition.

In some embodiments, subjects treated with the oligonucleotide composition of the present disclosure will show amelioration or elimination of one or more of the following conditions or symptoms: familial Alzheimer's disease, sporadic Alzheimer's disease, frontotemporal dementia with parkinsonism linked to chromosome 17 (FTDP-17), progressive supranuclear palsy, corticobasal degeneration, Pick's disease, progressive subcortical gliosis, tangle only dementia, diffuse neurofibrillary tangles with calcification, argyrophilic grain dementia, amyotrophic lateral sclerosis parkinsonism-dementia complex, Down syndrome, Gerstmann-Straussler-Scheinker disease, Hallervorden-Spatz disease, inclusion body myositis, Creutzfeld-Jakob disease, multiple system atrophy, Niemann-Pick disease type C, prion protein cerebral amyloid angiopathy, subacute sclerosing panencephalitis, myotonic dystrophy, non-Guamanian motor neuron disease with neurofibrillary tangles, postencephalitic parkinsonism, chronic traumatic encephalopathy, and dementia pugulistica (boxing disease).

In some embodiments, subjects treated with the oligonucleotide composition of the present disclosure will show a reduction in the expression levels of one or more biomarkers selected from among tau protein and MAPT mRNA, compared to untreated subjects suffering from tauopathy such as AD and/or any other tau-associated disorder.

The present disclosure provides a method for treating a subject diagnosed as having or suspected as having tauopathy such as AD and/or any other tau-associated disorder comprising administering to the subject an effective amount of an oligonucleotide composition of the present disclosure.

The oligonucleotides and compositions of the present disclosure may be used in antisense therapy. For example, the oligonucleotide may contain a nucleobase sequence that is complementary or hybridizes to a target nucleic acid sequence of a known DNA or RNA sequence implicated in AD such as at least a portion of the MAPT gene.

Some embodiments include a method of modulating expression of a target by contacting a target nucleic acid with an antisense compound comprising the oligonucleotide of the present disclosure. In some embodiments, the target nucleic acid is in a cell, for example, in an animal such as a human.

Some embodiments, include a method of inhibiting expression of an MAPT gene in an animal, comprising administering to the animal an antisense compound comprising the oligonucleotide of the present disclosure. The oligonucleotide may be complementary or hybridize to a portion of the MAPT gene.

Some embodiments include a method for reducing tau mRNA expression or levels of tau protein in a subject with AD comprising administering a therapeutically effective amount of a oligonucleotide or a composition of the present disclosure to the subject in need thereof thereby reducing tau mRNA expression or levels of tau protein in the subject. The oligonucleotide may be complementary or hybridize to a portion of the target RNA involved in the expression of tau mRNA such as MAPT mRNA.

The oligonucleotides and compositions of the present disclosure may be used, e.g., to inhibit or reduce tau or MAPT gene expression or inhibit transcription or translation of tau or MAPT for treatment of a subject having AD or for reducing tau or MAPT protein levels in a subject having or diagnosed with AD. In embodiments, the disclosed chimeric oligonucleotides are used to induce RNase H activity at a target gene such as the MAPT gene.

The present disclosure is also directed to methods of stabilizing an oligonucleotide for delivery to a subject. Stabilization of an oligonucleotide is characterized [quantified] herein as increasing the melting point or temperature, $T_m$, of an oligonucleotide.

The disclosed oligonucleotide constructs may be administered alone or in combination with one or more additional treatments for the targeted ailment. The disclosed oligonucleotide constructs may be administered alone or in combination with one or more additional treatments for AD. In combination therapies, the oligonucleotide constructs and one or more additional treatments for AD may be administered simultaneously in the same or separate compositions, or administered separately, at the same time or sequentially.

In some embodiments, the disclosed oligonucleotide constructs are administered in combination with tau or MAPT transcription or translation inhibitors or in regimens that combine anti-AD oligonucleotide agents with tau or MAPT transcription or translation inhibitors. In embodiments, the disclosed oligonucleotide constructs are administered in combination with standard of care treatment for tauopathies such as AD. Standard of care treatment for tauopathies such as AD can include acetylcholine esterase inhibitors, NMDA receptor modulators, BACE inhibitors, protein aggregation inhibitors, anti-tau antibodies, anti-Abeta antibodies, tau vaccination, Abeta vaccination and other known treatments for tauopathies. In embodiments, the disclosed oligonucleotide constructs are administered in combination with one or more oligonucleotides after either simultaneous (co-administration) or sequential dosing. Oligonucleotides can include siRNA oligonucleotides, antisense oligonucleotides such as Tau$^{ASO-12}$ (Devos et al., Sci Transl Med. 2017 Jan. 25; 9(374)), miRNA mimics or inhibitors, aptamers, steric blockers, saRNA, shRNA, and/or immunomodulatory oligonucleotides.

Some embodiments include inhibition of MAPT gene expression in a cell or subject comprising contacting the cell with an oligonucleotide or composition of the present disclosure, or administering a therapeutically effective amount of a oligonucleotide or composition of the present disclosure to a subject in need thereof.

Some embodiments include the treatment of a disease or disorder associated with the expression or activity of the MAPT gene comprising administering a therapeutically effective amount of an oligonucleotide or composition of the present disclosure to a subject in need thereof.

Some embodiments include a method for reducing tau mRNA expression or levels of tau protein of a tauopathy such as Alzheimer's disease (AD) in a subject having a tauopathy comprising administering a therapeutically effective amount of an oligonucleotide or composition of the present disclosure to the subject in need thereof thereby tau mRNA expression or levels of tau protein in the subject.

Some embodiments include a method for reducing MAPT mRNA expression or levels of MAPT protein of a tauopathy such as Alzheimer's disease (AD) in a subject having a tauopathy comprising administering a therapeutically effective amount of an oligonucleotide or composition of the present disclosure to the subject in need thereof thereby reducing MAPT mRNA expression or levels of MAPT protein in the subject.

In one embodiment, an oligonucleotide or composition of the present disclosure targeting MAPT is administered to a subject having a tauopathy such as Alzheimer's disease and/or any tauopathy-related disorder such that the expression of the MAPT gene and/or tau protein level, e.g., in a cell, tissue, blood or other tissue or fluid of the subject are reduced by at least about 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 62%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or at least about 99% or more, or values between two of these numbers, upon administration to the subject of the oligonucleotide or composition of the present disclosure. In some embodiments, the tau protein levels are decreased by the previously recited amount. In some embodiments the expression of one or more genes, including the MAPT gene, are decreased by the previously recited amount.

Administration of the oligonucleotide or composition of the present disclosure according to the methods and uses of the disclosure may result in a reduction of the severity, signs, symptoms, and/or markers of such diseases or disorders in a patient with tauopathy such as Alzheimer's disease and/or any tauopathy-related disorder. By "reduction" in this context is meant a statistically significant decrease in such level. The reduction can be, for example, at least about 5%, 10%, 15%, 20%, 25%, 30%, 35%, 40%, 45%, 50%, 55%, 60%, 65%, 70%, 75%, 80%, 85%, 90%, 95%, or about 100%, or values between two of these numbers.

The amount of an oligonucleotide or composition of the present disclosure may be determined by a medical professional. The daily dosage of the products may be varied over a wide range from 0.001 to 1,000 mg per adult human per day, or any range therein. For IT or ICV administration, the compositions are preferably provided in the form of suspensions containing, 0.01, 0.05, 0.1, 0.5, 1.0, 2.5, 5.0, 10.0, 15.0, 25.0, 50.0, 100, 150, 200, 250, and 500 milligrams of the active ingredient for the symptomatic adjustment of the dosage to the patient to be treated. An effective amount of the drug is ordinarily supplied at a dosage level of from about 0.01 mg/kg to about 100 mg/kg of body weight per day, or any range therein. Preferably, the range is from about 0.01 to about 50.0 mg/kg of body weight per day, or any range therein. More preferably, from about 0.01 to about 10.0 mg/kg of body weight per day, or any range therein. More preferably, from about 0.01 to about 1.0 mg/kg of body weight per day, or any range therein. The oligonucleotides may be administered on a regimen of 1 to 4 times per day. For example, the oligonucleotides of the present disclosure may be administered at one or more doses of from about 0.1 mg/kg to about 100 mg/kg. For example, the disclosed oligonucleotides may be administered at a dose of about 0.1, 0.2, 0.3, 0.4, 0.5, 0.6, 0.7, 0.8, 0.9, 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3, 3.1, 3.2, 3.3, 3.4, 3.5, 3.6, 3.7, 3.8, 3.9, 4, 4.1, 4.2, 4.3, 4.4, 4.5, 4.6, 4.7, 4.8, 4.9, 5, 5.1, 5.2, 5.3, 5.4, 5.5, 5.6, 5.7, 5.8, 5.9, 6, 6.1, 6.2, 6.3, 6.4, 6.5, 6.6, 6.7, 6.8, 6.9, 7, 7.1, 7.2, 7.3, 7.4, 7.5, 7.6, 7.7, 7.8, 7.9, 8, 8.1, 8.2, 8.3, 8.4, 8.5, 8.6, 8.7, 8.8, 8.9, 9, 9.1, 9.2, 9.3, 9.4, 9.5, 9.6, 9.7, 9.8, 9.9, 10, 10.5, 11, 11.5, 12, 12.5, 13, 13.5, 14, 14.5, 15, 15.5, 16, 16.5, 17, 17.5, 18, 18.5, 19, 19.5, 20, 20.5, 21, 21.5, 22, 22.5, 23, 23.5, 24, 24.5, 25, 25.5, 26, 26.5, 27, 27.5, 28, 28.5, 29, 29.5, 30, 31, 32, 33, 34, 34, 35, 36, 37, 38, 39, 40, 41, 42, 43, 44, 45, 46, 47, 48, 49, 50, 55, 60, 65, 70, 75, 80, 85, 90, 95 or about 100 mg/kg. Values and ranges intermediate to the recited values are also intended to be part of this disclosure. These values may apply to intrathecal or intracerebroventricular delivery. Other forms of delivery described herein may also be administered at these doses. The dosages may be varied depending upon the requirement of the patients, the severity of the condition being treated, and the oligonucleotides being employed. The use of either daily administration or post-periodic dosing may be employed.

The oligonucleotides of the present disclosure can be administered by intrathecal or intracerebroventricular infusion over a period of time, such as over a 5, 6, 7, 8, 9, 10, 11, 12, 13, 14, 15, 16, 17, 18, 19, 20, 21, 22, 23, 24, or about a 25 minute period. The administration may be repeated, for example, on a regular basis, such as weekly, biweekly (i.e., every two weeks) for one month, two months, three months, four months, or longer. After an initial treatment regimen, the treatments can be administered on a less frequent basis. For example, after administration weekly or biweekly for three months, administration can be repeated once per month, for six months or a year or longer.

Efficacy of treatment or prevention of disease can be assessed, for example by measuring disease progression, disease remission, symptom severity, cognitive measures, reduction in pain, quality of life, dose of a medication required to sustain a treatment effect, level of a disease marker or any other measurable parameter appropriate for a given disease being treated or targeted for prevention. It is well within the ability of one skilled in the art to monitor efficacy of treatment or prevention by measuring any one of such parameters, or any combination of parameters. For example, efficacy of treatment of a tauopathy such as AD may be assessed, for example, by periodic monitoring of expression of the MAPT gene and/or tau protein levels. Comparison of the later readings with the initial readings provides an indication of whether the treatment is effective.

4. Definitions

It is to be understood that the terminology used herein is for the purpose of describing particular embodiments only and is not intended to limit the scope of the present invention. The following definitions shall apply unless otherwise indicated.

As used herein, the terms "complementary" or "complementarity" as used herein with reference to polynucleotides (i.e., a sequence of nucleotides such as an oligonucleotide or a target nucleic acid) refer to the base-pairing rules. The complement of a nucleic acid sequence as used herein refers to an oligonucleotide which, when aligned with the nucleic acid sequence such that the 5' end of one sequence is paired with the 3' end of the other, is in "antiparallel association." For example, the sequence "5'-A-G-T-3'" is complementary to the sequence "3'-T-C-A-5'." Certain bases not commonly found in naturally occurring nucleic acids may be included in the nucleic acids described herein. These include, for example, inosine, 7-deazaguanine, Locked Nucleic Acids (LNA), and Peptide Nucleic Acids (PNA). Complementarity need not be perfect; stable duplexes may contain mismatched base pairs, degenerative, or unmatched bases. Those skilled in the art of nucleic acid technology can determine duplex stability empirically considering a number of variables including, for example, the length of the oligonucleotide, base composition, and sequence of the oligonucleotide, ionic strength, and incidence of mismatched base pairs. A complement sequence can also be an RNA sequence complementary to the DNA sequence or its complement and can also be a cDNA.

As used herein, the term "hybridize" as used herein refers to a process where two substantially complementary nucleic acid strands (at least about 65% complementary over a stretch of at least 14 to 25 nucleotides, at least about 75%, or at least about 90% complementary) anneal to each other under appropriately stringent conditions to form a duplex or heteroduplex through formation of hydrogen bonds between complementary base pairs. Hybridizations are typically, and preferably, conducted with probe-length nucleic acid molecules, preferably 15-100 nucleotides in length, more preferably 18-50 nucleotides in length. Nucleic acid hybridization techniques are well known in the art. See, e.g., Sambrook, et al., 1989, *Molecular Cloning: A Laboratory Manual*, Second Edition, Cold Spring Harbor Press, Plainview, N.Y. Hybridization and the strength of hybridization (i.e., the strength of the association between the nucleic acids) is influenced by such factors as the degree of complementarity between the nucleic acids, stringency of the conditions involved, and the thermal melting point ($T_m$) of the formed hybrid. Those skilled in the art understand how to estimate and adjust the stringency of hybridization conditions such that sequences having at least a desired level of complementarity will stably hybridize, while those having lower complementarity will not. For examples of hybridization conditions and parameters, see, e.g., Sambrook, et al., 1989, *Molecular Cloning: A Laboratory Manual*, Second Edition, Cold Spring Harbor Press, Plainview, N.Y.; Ausubel, F. M. et al. 1994, *Current Protocols in Molecular Biology*, John Wiley & Sons, Secaucus, N.J. In some embodiments, specific hybridization occurs under stringent hybridization conditions. An oligonucleotide or polynucleotide (e.g., a probe or a primer) that is specific for a target nucleic acid will "hybridize" to the target nucleic acid under suitable conditions.

As used herein, the term "stringent hybridization conditions" as used herein refers to hybridization conditions at least as stringent as the following: hybridization in 50% formamide, 5×SSC, 50 mM $NaH_2PO_4$, pH 6.8, 0.5% SDS, 0.1 mg/mL sonicated salmon sperm DNA, and 5×Denhart's solution at 42° C. overnight; washing with 2×SSC, 0.1% SDS at 45° C.; and washing with 0.2×SSC, 0.1% SDS at 45° C. In another example, stringent hybridization conditions should not allow for hybridization of two nucleic acids, which differ over a stretch of 20 contiguous nucleotides by more than two bases.

As used herein, the term "substantially complementary" as used herein means that two sequences hybridize under stringent hybridization conditions. The skilled artisan will understand that substantially complementary sequences need not hybridize along their entire length. In particular, substantially complementary sequences may comprise a contiguous sequence of bases that do not hybridize to a target sequence, positioned 3' or 5' to a contiguous sequence of bases that hybridize under stringent hybridization conditions to a target sequence.

As used herein, the term "pharmaceutically acceptable" refers to a material that is not biologically or otherwise undesirable, i.e., the material may be incorporated into a pharmaceutical composition administered to a patient without causing any undesirable biological effects or interacting in a deleterious manner with any of the other components of the composition in which it is contained. When the term "pharmaceutically acceptable" is used to refer to a pharmaceutical carrier or excipient, it is implied that the carrier or excipient has met the required standards of toxicological and manufacturing testing or that it is included on the Inactive Ingredient Guide prepared by the U.S. and Drug administration.

As used herein, the term "construct" or "constructs" of the oligonucleotides can refer to an oligonucleotide of the present disclosure and, e.g., (1) a conjugated moiety, such as those described herein (such as targeting moieties) or (2) domains of modified/unmodified nucleotides, such as in some chimeric oligonucleotides.

As used herein, the term "chimeric oligonucleotide" refers to an oligonucleotide having more than one domain, for example, as exemplified by Formulae (VI) and (VII). The chimeric oligonucleotide may include additional components, e.g., a ligand-targeting group or additional nucleotides, linkers, etc.

As used herein, the term "modified nucleoside" refers to a nucleoside having, independently, a modified sugar moiety and/or modified nucleobase. It is understood that nucleosides can be linked through intersubunit linkages, such as phosphodiester intersubunit linkages, thiophosphate intersubunit linkages, phosphoramidate intersubunit linkages, and thiophosphoramidate intersubunit linkages "Modified nucleotides" may refer to a nucleoside and intersubunit linkage together.

As used herein, the terms "unmodified" or "natural" nucleobases include the purine bases adenine (A) and guanine (G), and the pyrimidine bases thymine (T), cytosine (C) and uracil (U). "Modified nucleobases" include other synthetic and natural nucleobases such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl (—C≡C—$CH_3$) uracil and cytosine and other alkynyl derivatives of pyrimidine bases, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 2-F-adenine, 2-aminoadenine, 8-azaguanine and 8-azaadenine, 7-deazaguanine and 7-deazaadenine and 3-deazaguanine and 3-deazaadenine. Further modified nucleobases include tricyclic pyrimidines such as phenoxazine cytidine(1H-pyrimido[5,4-b][1,4]benzoxazin-2(3H)-one), phenothiazine cytidine (1H-pyrimido[5,4-b][1,4]benzothiazin-2(3H)-one), G-clamps such as a substituted phenoxazine cytidine (e.g. 9-(2-am-oelhoxy)-H-pyrimido[5,4-b][1,4]benzoxazin-2 (3H)-one), carbazole cytidine (2H-pyrimido[4,5-b]indol-2-one), pyridoindole cytidine (H-pyrido[3,2,5]pyrrolo[2,3-d] pyrimidin-2-one). Modified nucleobases may also include those in which the purine or pyrimidine base is replaced with other heterocycles, for example 7-deaza-adenine, 7-deazaguanosine, 2-aminopyridine, and 2-pyridone.

In some embodiments, the modified nucleobase is selected from the group consisting of 5-methylcytosine, 2,6-diaminopurine, 5-methyluracil, and a g-clamp. In some embodiments, the g-clamp is

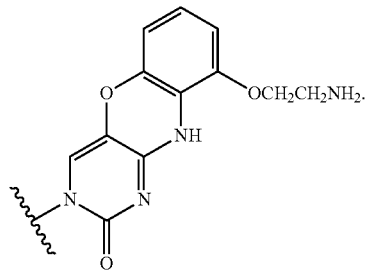

As used herein, the terms "ligand targeting group" or "targeting moiety" refers to a moiety that promotes delivery of the oligonucleotide to cells implicated in tauopathies enhancing cellular uptake or improving pharmacokinetics including bioavailability of the oligonucleotide to its target sequence. These groups include receptor targeting ligands that target the receptors on cell surfaces.

As used herein, the term "conformationally restricted nucleoside" refers to nucleosides having a bridged or bicyclic sugar structure wherein the conformation of the nucleoside may be fixed in a particular configuration. For example, conformationally restricted nucleosides include those with fixed C3'-endo sugar puckering. Exemplary embodiments include bridged nucleic acids (BNAs), e.g., 2', 4'-BNA nucleosides such as α-L-Methyleneoxy (4'-$CH_2$—O—2') LNA, β-D-Methyleneoxy (4'-$CH_2$—O-2') LNA, Ethyleneoxy (4'—$(CH_2)_2$—O—2') ENA, 2',4'-$BNA^{NC}$[NH], 2',4'-$BNA^{NC}$[NMe], 2',4'-$BNA^{NC}$[NBn], aminooxy (4'-$CH_2$—O—N(R)-2') BNA, and oxyamino (4'-$CH_2$—N(R)—O—2') BNA. Other exemplary BNA structures include but are not limited to, oligonucleotides having at least one bridge between the 4' and the 2' position of the sugar wherein each of the bridges independently comprises 1 or from 2 to 4 linked groups independently selected from $[C(R_1)(R_2)]_n$—, $C(R_1)=C(R_2)$—, $C(R_1)=N$—, $C(=NR_1)$—, $C(=O)$—, $C(=S)$, —O—, $Si(R_1)_2$—, —$S(=O)_x$— and $N(R_1)$—; wherein: x is 0, 1, or 2; n is 1, 2, 3, or 4; each $R_1$ and $R_2$ is, independently, H, a protecting group, hydroxyl, $C_1$-$C_{12}$ alkyl, substituted $C_1$-$C_{12}$ alkyl, $C_2$-$C_{12}$alkenyl, substituted $C_2$-$C_{12}$ alkenyl, $C_2$-$C_{12}$ alkynyl, substituted $C_2$-$C_{12}$ alkynyl, $C_5$-$C_{20}$ aryl, substituted $C_5$-$C_{20}$ aryl, a heterocycle radical, a substituted heterocycle radical, heteroaryl, substituted heteroaryl, $C_5$-$C_7$ alicyclic radical, substituted $C_5$-$C_7$ alicyclic radical, halogen, $OJ_1$, $NJ_1J_2$, $SJ_1$, $N_3$, $COOJ_1$, acyl ($C(=O)$—H), substituted acyl, CN, sulfonyl ($S(=O)_2$-$J_1$), or sulfoxyl ($S(=O)$-$J_1$); and each $J_1$ and $J_2$ is, independently, H, $C_1$-$C_{12}$ alkyl, substituted $C_1$-$C_{12}$ alkyl, $C_2$-$C_{12}$ alkenyl, substituted $C_2$-$C_{12}$alkenyl, $C_2$-$C_{12}$ alkynyl, substituted $C_2$-$C_{12}$ alkynyl, $C_5$-$C_{20}$ aryl, substituted $C_5$-$C_{20}$ aryl, acyl ($C(=O)$—H), substituted acyl, a heterocycle radical, a substituted heterocycle radical, $C_1$-$C_{12}$ aminoalkyl, substituted $C_1$-$C_{12}$ aminoalkyl or a protecting group. Certain BNAs have been prepared and disclosed in the patent literature as well as in scientific literature (see for example: issued U.S. Pat. Nos. 7,053,207; 6,268,490; 6,770,748; 6,794,499; 7,034,133; 6,525,191; 7,696,345; 7,569,575; 7,314,923; 7,217,805; and 7,084,125, hereby incorporated by reference herein in their entirety. "Conformationally restricted nucleotide" refers to conformationally restricted nucleosides linked through an intersubunit linkage.

In some embodiments, the conformationally restricted nucleoside is selected from optionally substituted LNA or optionally substituted ENA. The optionally substituted LNA or ENA may be substituted by an alkyl moiety, for example a methyl or ethyl on one of the —$CH_2$— moieties.

As used herein, the term "expression" refers to the biosynthesis of a gene product. The term encompasses the transcription of a gene into RNA. The term also encompasses transcription of RNA into one or more polypeptides, and further encompasses all naturally occurring post-transcriptional and post-translational modifications. The oligonucleotides of the present disclosure can be within the cytoplasm of a host cell, into the extracellular milieu such as the growth medium of a cell culture or anchored to the cell membrane.

As used herein, the term "inhibiting expression" refers to a reduction or blockade of the expression or activity and does not necessarily indicate a total elimination of expression or activity.

As used herein, the term "reducing protein levels" refers to reduction or blockade of transcription of mRNA to form a protein encoded by the mRNA and does not necessarily indicate a total elimination of transcription of mRNA or the protein.

As used herein, the term "subject" refers to mammals and includes humans and non-human mammals. In some embodiments, the subject is a human, such as an adult human.

As used herein, the term "tau" or "tau protein" refers to an abundant central and peripheral nervous system protein having multiple isoforms. In the human central nervous system (CNS), six major tau isoforms ranging in size from 352 to 441 amino acids in length exist due to alternative splicing (Hanger et al., *Trends Mol Med.* 15:112-9, 2009). The isoforms differ from each other by the regulated inclusion of 0-2 N-terminal inserts, and 3 or 4 tandemly arranged microtubule-binding repeats and are referred to as 0N3R (SEQ ID NO: 64), 1N3R (SEQ ID NO: 65), 2N3R (SEQ ID NO: 66), 0N4R (SEQ ID NO: 67), 1N4R (SEQ ID NO: 68) and 2N4R (SEQ ID NO: 69). As used herein, the term "control tau" refers to the tau isoform of SEQ ID NO: 69 that is devoid of phosphorylation and other post-translational modifications. As used herein, the term "tau" includes proteins comprising mutations, e.g., point mutations, fragments, insertions, deletions and splice variants of full length wild type tau. The term "tau" also encompasses post-translational modifications of the tau amino acid sequence. Post-translational modifications include, but are not limited to, phosphorylation. Tau binds microtubules and regulates transport of cargo through cells, a process that can be modulated by tau phosphorylation. In AD and related disorders, abnormal phosphorylation of tau is prevalent and thought to precede and/or trigger aggregation of tau into fibrils, termed paired helical filaments (PHF). The major constituent of PHF is hyper-phosphorylated tau. As used herein, the term "paired helical filament-tau" or "PHF-tau" refers to tau aggregates in paired helical filaments. Two major regions in PHF structure are evident in electron microscopy, the fuzzy coat and the core filament; the fuzzy coat being sensitive to proteolysis and located outside of the filaments, and the protease-resistant core of filaments forming the backbone of PHFs (Wischik et al. *Proc Natl Acad Sci USA*. 85:4884-8, 1988).

As used herein a "tauopathy" encompasses any neurodegenerative disease that involves the pathological aggregation of tau within the brain. In addition to familial and sporadic AD, other exemplary tauopathies are frontotemporal dementia with parkinsonism linked to chromosome 17 (FTDP-17), progressive supranuclear palsy, corticobasal degeneration, Pick's disease, progressive subcortical gliosis, tangle only dementia, diffuse neurofibrillary tangles with calcification, argyrophilic grain dementia, amyotrophic lateral sclerosis parkinsonism-dementia complex, Down syndrome, Gerstmann-Straussler-Scheinker disease, Hallervorden-Spatz disease, inclusion body myositis, Creutzfeld-Jakob disease, multiple system atrophy, Niemann-Pick disease type C, prion protein cerebral amyloid angiopathy, subacute sclerosing panencephalitis, myotonic dystrophy, non-Guamanian motor neuron disease with neurofibrillary tangles, postencephalitic parkinsonism, and chronic traumatic encephalopathy, such as dementia pugulistica (boxing disease) (Morris et al., *Neuron*, 70:410-26, 2011).

As used herein, the terms "treat," "treating," and "treatment" are all intended to refer to an amelioration or reversal of at least one measurable physical parameter related to a tauopathy which is not necessarily discernible in the subject, but can be discernible in the subject. The terms "treat," "treating," and "treatment," can also refer to causing regression, preventing the progression, or at least slowing down the progression of the disease, disorder, or condition. In a particular embodiment, "treat," "treating," and "treatment" refer to an alleviation, prevention of the development or onset, or reduction in the duration of one or more symptoms associated with the tauopathy. In a particular embodiment, "treat," "treating," and "treatment" refer to prevention of the recurrence of the disease, disorder, or condition. In a particular embodiment, "treat," "treating," and "treatment" refer to an increase in the survival of a subject having the disease, disorder, or condition. In a particular embodiment, "treat," "treating," and "treatment" refer to elimination of the disease, disorder, or condition in the subject.

As used herein, the term "therapeutically effective amount" refers to an amount of an active ingredient or component that elicits the desired biological or medicinal response in a subject. A therapeutically effective amount can be determined empirically and in a routine manner, in relation to the stated purpose. For example, in vitro assays can optionally be employed to help identify optimal dosage ranges. Selection of a particular effective dose can be determined (e.g., via clinical trials) by those skilled in the art based upon the consideration of several factors, including the disease to be treated or prevented, the symptoms involved, the patient's body mass, the patient's immune status and other factors known by the skilled artisan. The precise dose to be employed in the formulation will also depend on the route of administration, and the severity of disease, and should be decided according to the judgment of the practitioner and each patient's circumstances. Effective doses can be extrapolated from dose-response curves derived from in vitro or animal model test systems.

As used herein, the term, "pharmaceutically acceptable salt" means physiologically and pharmaceutically acceptable salts of the compounds of the present disclosure, i.e., salts that retain the desired biological activity of the parent oligonucleotide/compound and do not impart undesired toxicological effects thereto.

The following abbreviations are used in this disclosure. 2'-H (deoxyribose) nucleosides are referred to by an uppercase letter corresponding to the nucleobase, e.g., A, C, G, and T. 2'-OH (ribose) nucleosides are referred to by a lowercase r and an uppercase letter corresponding to the nucleobase, e.g., rA, rC, rG, and rU. 2'-O-Me nucleosides are referred to by a lowercase m and an uppercase letter corresponding to the nucleobase, e.g., mA, mC, mG and mU. 2'-MOE nucleosides are referred to by a lowercase "moe" and an uppercase letter corresponding to the nucleobase, e.g., moeA, moeC, moeG and moeU. 2'-ribo-F nucleosides are referred to by a lowercase "f" and an uppercase letter corresponding to the nucleobase, e.g., fA, fC, fG and fU. 2'-arabino-F nucleosides are referred to by a lowercase "af" and an uppercase letter corresponding to the nucleobase, e.g., afA, afC, afG and afU. mA* is 3'-amino-2'-OMe-2,6-Diaminopurine. A* is 3'-amino-2'-deoxy-2,6-Diaminopurine. fA* is 3'-amino-2'-F-2,6-Diaminopurine. LNA nucleosides are referred to by an "L" and an uppercase letter corresponding to the nucleobase, e.g., LA, LC, LG, LT.

For the backbone or intersubunit linkages of the nucleotides, phosphodiester intersubunit linkages are referred to as "PO" or are generally not included in sequence details; thiophosphate intersubunit linkages are abbreviated as lowercase "ps"; phosphoramidate intersubunit linkages are abbreviated as lowercase "np"; and thiophosphoramidate intersubunit linkages are abbreviated as lowercase "nps."

N3'→P5' refers to modified nucleotides having intersubunit linkages where the 3' moiety contains N (e.g., NH) and is linked through a P. For example, the following structure has a N3'→P5' linkage:

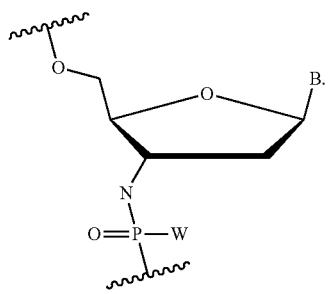

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely", "only" and the like in connection with the recitation of claim elements or use of a "negative" limitation.

The term "about" will be understood by persons of ordinary skill in the art and will vary to some extent depending upon the context in which it is used. If there are uses of the term which are not clear to persons of ordinary skill in the art given the context in which it is used, "about" will mean up to plus or minus 10% of the particular term. Certain ranges are presented herein with numerical values being preceded by the term "about". The term "about" is used herein to provide literal support for the exact number that it precedes, as well as a number that is near to or approximately the number that the term precedes. In determining whether a number is near to or approximately a specifically recited number, the near or approximating unrecited number may be a number, which, in the context in which it is presented, provides the substantial equivalent of the specifically recited number.

It is also to be appreciated that the various modes of treatment or prevention of the diseases or conditions described herein are intended to mean "substantial," which includes total but also less than total treatment or prevention, and wherein some biologically or medically relevant result is achieved. The treatment may be a continuous prolonged treatment for a chronic disease or a single, or few time administrations for the treatment of an acute condition.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention.

This disclosure is not limited to particular embodiments described, as such may vary. It is also to be understood that the terminology used herein is for the purpose of describing particular embodiments only, and is not intended to be limiting, since the scope of the present invention will be limited only by the appended claims.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order that is logically possible.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual publication dates that may need to be independently confirmed.

5. Examples

The following examples illustrate certain embodiments of the present disclosure to aid the skilled person in practicing the disclosure. Accordingly, the examples are in no way considered to limit the scope of the disclosure.

Methods of Making

All the monomers were dried in vacuum desiccator with desiccants (KOH and $P_2O_5$, RT 24 h). Synthesis solid supports (CPG) attached to the first 5' residue were obtained from commercially available sources. All other synthesis reagents and solvents were obtained from commercially available sources and used as such. The chemicals and solvents for post synthesis workflow were purchased from commercially available sources and used without any purification or treatment. Solvent (Acetonitrile) and solutions (amidite and activator) were stored over molecular sieves during synthesis.

The antisense oligonucleotides were synthesized on an ABI-394 synthesizer using the standard 93-step cycle written by the manufacturer. The solid support was controlled pore glass and the monomers contained standard protecting groups. Each oligonucleotide was individually synthesized using commercially available 5'-O-(4,4'-dimethoxytrityl)-3'-O-(2-cyanoethyl-N,N-diisopropyl) DNA and or 2'-O-Me phosphoramidite monomers of 6-N-benzoyladenosine ($A^{Bz}$), 4-N-acetylcytidine ($C^{Ac}$), 2-N-isobutyrylguanosine ($G^{iBu}$), and Thymidine (T), according to standard solid phase oligonucleotide synthesis protocols. The phosphoramidites were purchased from commercially available sources. The 2'-O-Me-2,6,diaminopurine phosphoramidite was purchased from commercially available sources. The DDTT ((dimethylamino-methylidene) amino)-3H-1,2,4-dithiazaoline-3-thione was used as the sulfur-transfer agent for the synthesis of oligoribonucleotide phosphorothioates. Modified oligonucleotides were obtained using an extended coupling of 0.1M solution of phosphoramidite in $CH_3CN$ in the presence of 5-(ethylthio)-1H-tetrazole activator to a solid bound oligonucleotide followed by standard capping, oxidation and deprotection. The stepwise coupling efficiency of all modified phosphoramidites was more than 98%. Oligonucleotide-bearing solid supports were heated with aqueous ammonia/ethanol (3:1) solution at 55° C. for 8 h to deprotect the base labile protecting groups.

Tocopherol conjugated oligonucleotides may be obtained by starting solid phase synthesis on tocopherol support attach on TEG linker and final coupling of the phosphoramidite to the support-bound oligonucleotide. The tocopherol conjugated sequences may be purified by high-performance liquid chromatography (HPLC) on an in-house packed RPC-Source15 reverse-phase column. The buffers may be 20 mM NaOAc in 10% $CH_3CN$ (buffer A) and 20 mM NaOAc in 70% $CH_3CN$ (buffer B). Analytical HPLC and ES LC-MS establishes the integrity of the oligonucleotides.

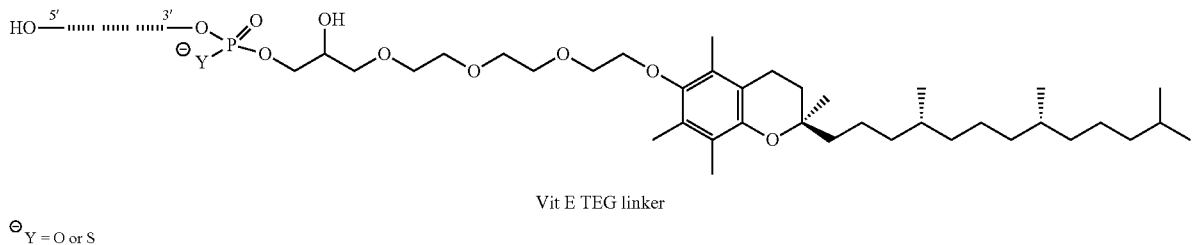

Vit E TEG linker $^{\ominus}Y$ = O or S

Synthesis of Phosphoramidate (NP) and Thiophosphoramidate (NPS) Modified Oligonucleotides The NP and NPS modified oligonucleotides were synthesized on an ABI-394 synthesizer using the 93-step cycle written with modifications to deblock, coupling and wait steps. The solid support was 3'-NHTr-5'-LCAA-CPG. Each oligonucleotide was individually synthesized using 3'-NH-Tr-5'-O-(2-cyanoethyl-N,N-diisopropyl) DNA phosphoramidite monomers of 6-N-benzoyladenosine ($A^{Bz}$), 4-N-Benzylcytidine ($C^{Bz}$), 2-N-isobutyrylguanosine ($G^{iBu}$), and Thymidine (T), according to standard solid phase phosphoramidite chemistry protocols by using the procedure described in *Nucleic Acids Research*, 1995, Vol. 23, No. 14 2661-2668.

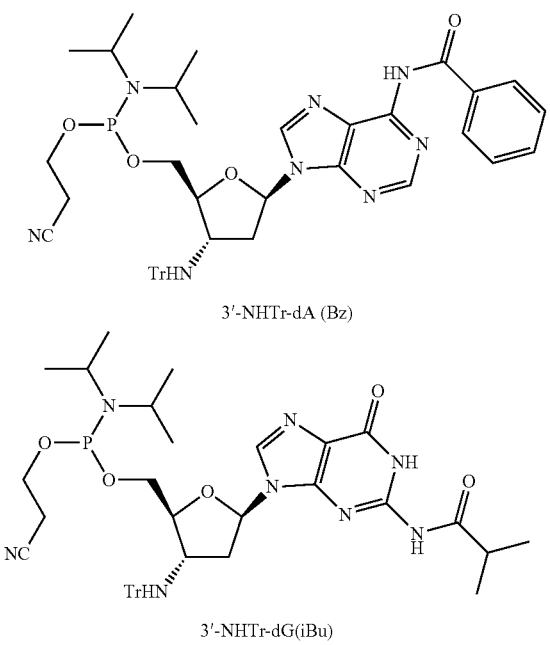

3'-NHTr-dA (Bz)

3'-NHTr-dG(iBu)

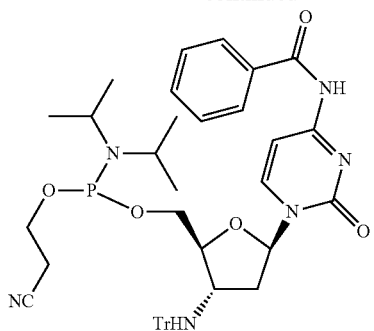

3'-NHTr-dC(Bz)

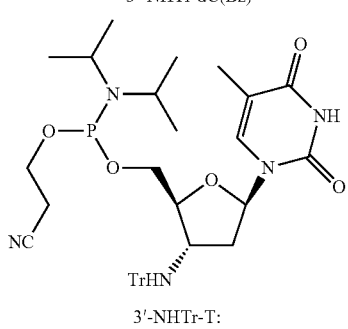

3'-NHTr-T:

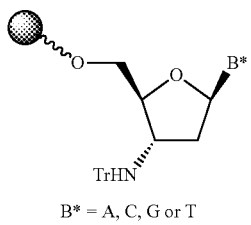

B* = A, C, G or T

3'-NHTr-DNA Building Blocks for Oligomer Synthesis

The 2'-F 3'-NH-MMTr-5'-O-(2-cyanoethyl-N,N-diisopropyl) Uridine (U) and 4-N-benzoylcytidine ($C^{Bz}$) phosphoramidite monomers) were synthesized by using the procedure described in *Nucleic Acids Research*, 1996, Vol. 24, No. 15, 2966-2973

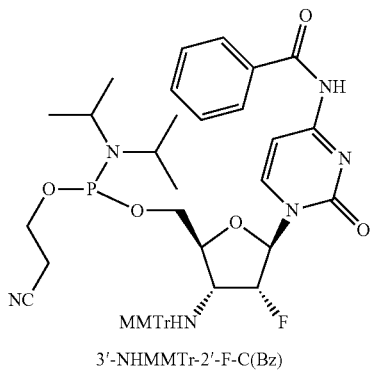

3'-NHMMTr-2'-F-C(Bz)

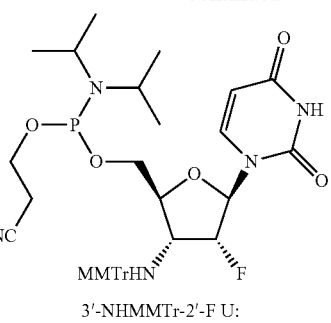

3'-NHMMTr-2'-F U:

2'-F 3'-NH-MMTr-5'-O-(2-cyanoethyl-N,N-diisopropyl)$_6$-N-benzoyladenosine ($A^{Bz}$), 2-N-isobutyrylguanosine ($G^{iBu}$), were synthesized as the procedure described below

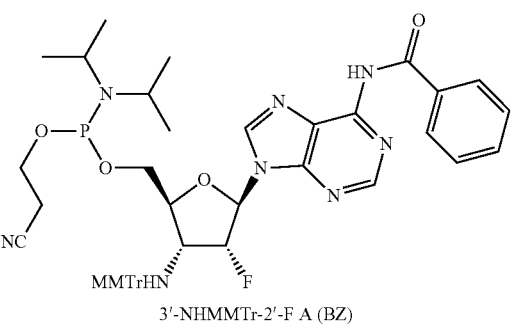

3'-NHMMTr-2'-F A (BZ)

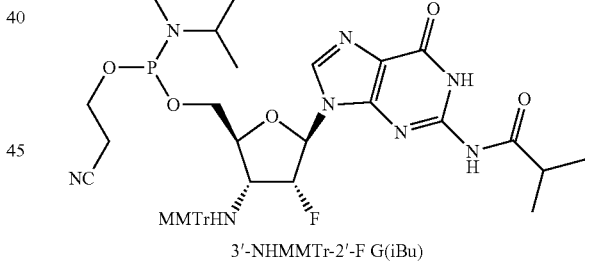

3'-NHMMTr-2'-F G(iBu)

**

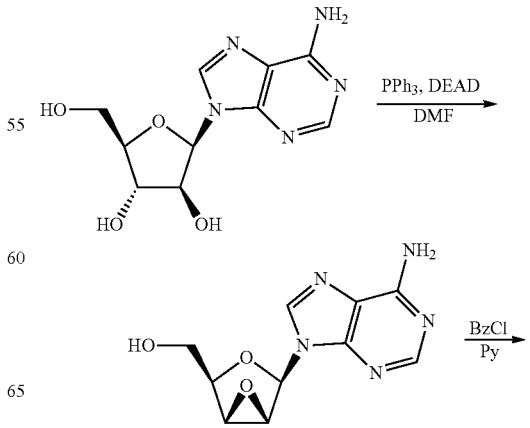

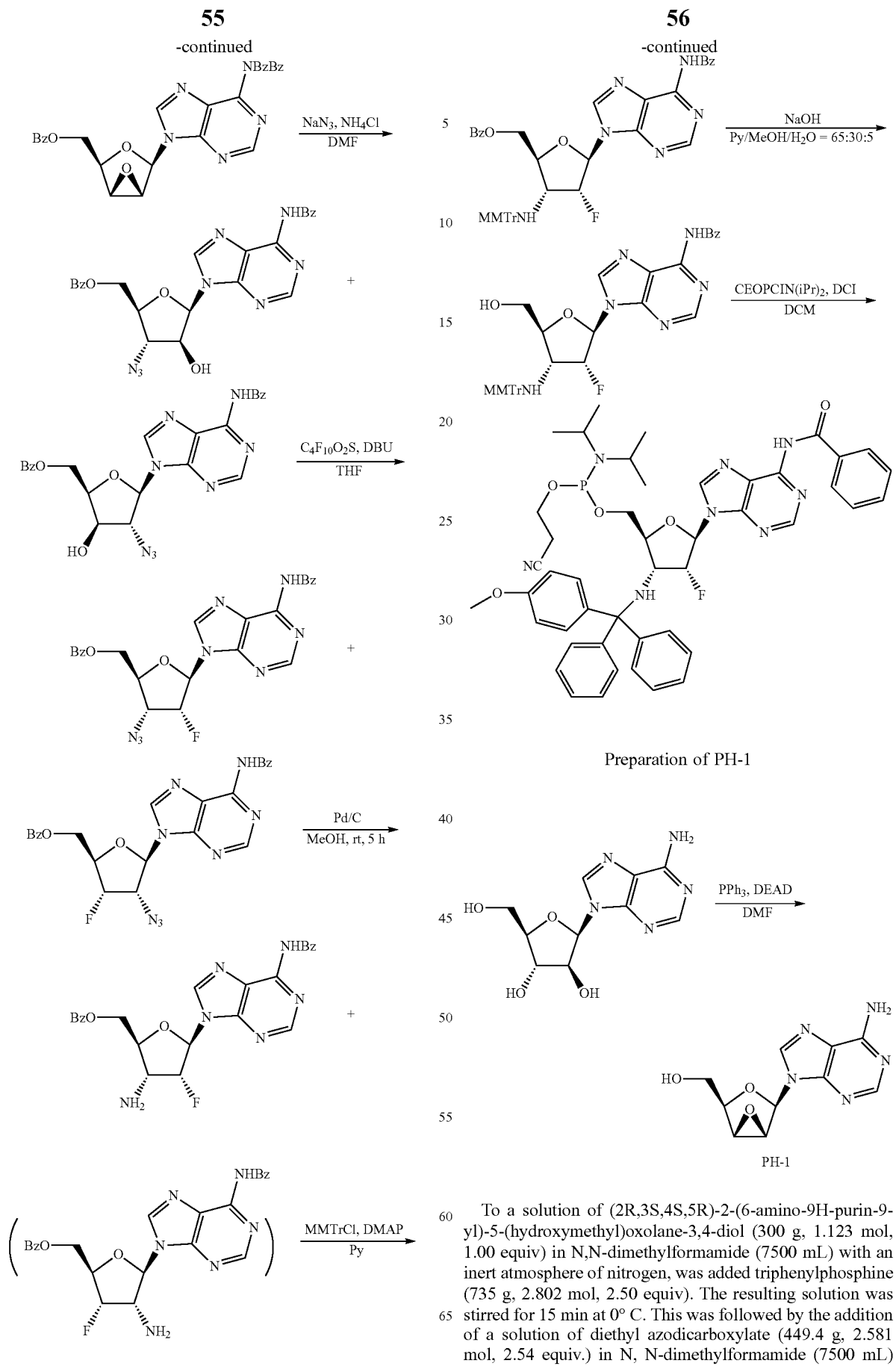

Preparation of PH-1

To a solution of (2R,3S,4S,5R)-2-(6-amino-9H-purin-9-yl)-5-(hydroxymethyl)oxolane-3,4-diol (300 g, 1.123 mol, 1.00 equiv) in N,N-dimethylformamide (7500 mL) with an inert atmosphere of nitrogen, was added triphenylphosphine (735 g, 2.802 mol, 2.50 equiv). The resulting solution was stirred for 15 min at 0° C. This was followed by the addition of a solution of diethyl azodicarboxylate (449.4 g, 2.581 mol, 2.54 equiv.) in N, N-dimethylformamide (7500 mL)

dropwise with stirring at 0° C. in 60 min. The resulting solution was stirring, for 2 h at 25° C. The resulting mixture was concentrated under reduced pressure. The product was precipitated by the addition of ether. The solids were collected by filtration. The crude product was purified by re-crystallization from methanol. The solid was dried in an oven under reduced pressure. This resulted in 186 g (66%) of PH-1 as a white solid. 1H-NMR (DMSO-$d_6$, 400 MHz): 8.34-8.07 (m, 2H), 7.44-7.26 (m, 2H), 6.30-6.21 (m, 1H), 5.07-4.95 (m, 1H), 4.33-4.20 (m, 1H), 4.15-4.03 (m, 2H), 3.71-3.50 (m, 2H).

Preparation of PH-2

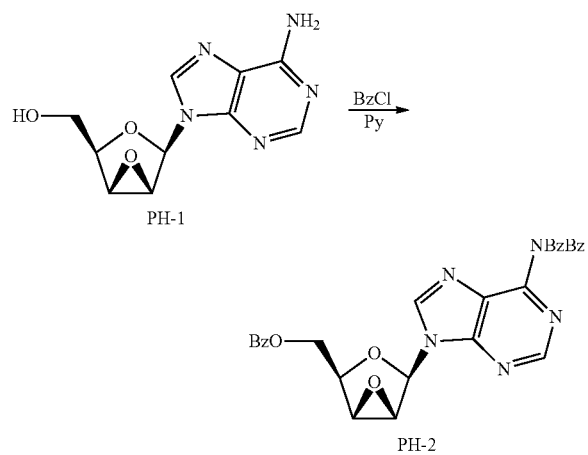

To a solution of PH-1 (100 g, 401.2 mmol, 1.00 equiv.) in pyridine (1000 mL) with an inert atmosphere of nitrogen, was added benzoyl chloride (175 g, 1.245 mol, 3.10 equiv.) dropwise with stirring at 0° C. in 30 min. The resulting solution was stirred for 3 h at 25° C. The resulting solution was diluted with 400 mL of ethyl acetate. The resulting mixture was washed with 3×300 mL of water and 2×300 mL of saturated sodium bicarbonate solution respectively. The resulting mixture was washed with 1×300 mL of saturated sodium chloride solution. The mixture was dried over anhydrous sodium sulfate, filtered, and concentrated under reduced pressure. The residue was applied onto a silica gel column with ethyl acetate/petroleum ether (2/1). This resulted in 157 g (70%) of PH-2 as a white solid.

Preparation of PH-3

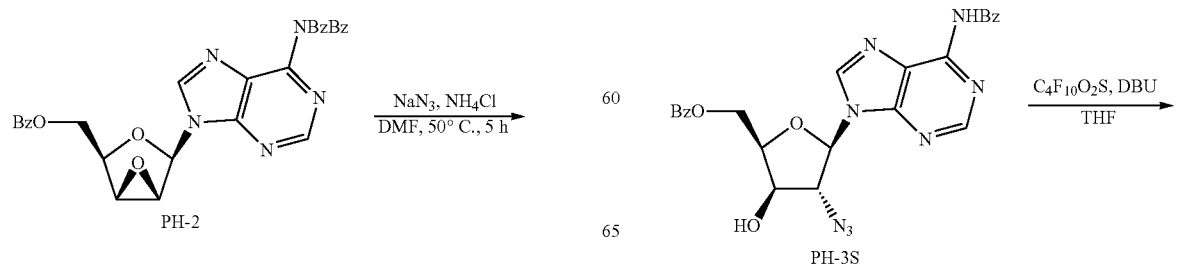

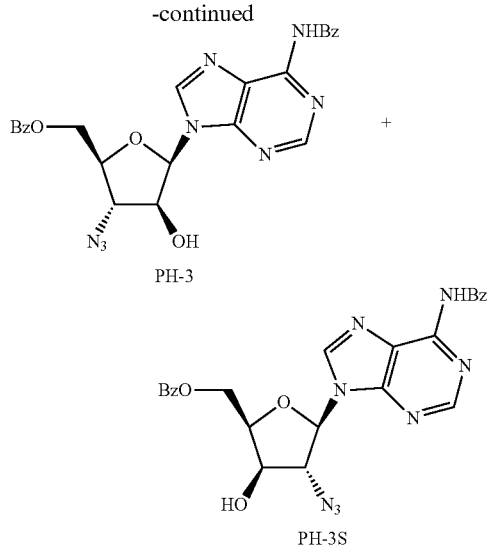

To a solution of PH-2 (30 g, 53.42 mmol, 1.00 equiv) in N,N-dimethylformamide (300 mL) with an inert atmosphere of nitrogen, was added ammonium chloride (5.7 g, 106.56 mmol, 2.00 equiv) and sodium azide (34.8 g, 535.30 mmol, 10.00 equiv) in order. The resulting solution was stirred for 5 h at 50° C. The resulting solution was diluted with 2000 mL of dichloromethane. The resulting mixture was washed with 3×2000 mL of water, 1×2000 mL of saturated sodium bicarbonate solution and 1×2000 mL of saturated sodium chloride solution respectively. The mixture was dried over anhydrous sodium sulfate, filtered, and concentrated under reduced pressure. This resulted in 24 g (90%) of PH-3 and PH-3S (5:1) as a white solid.

Preparation of PH-4

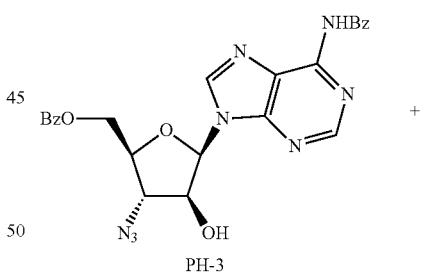

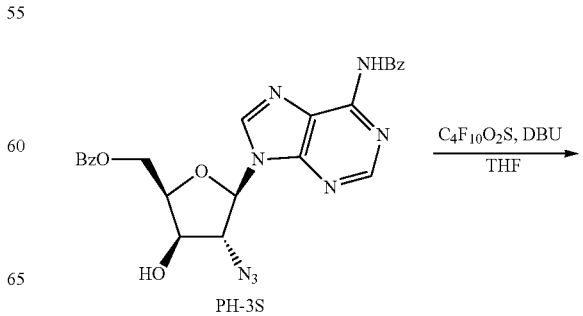

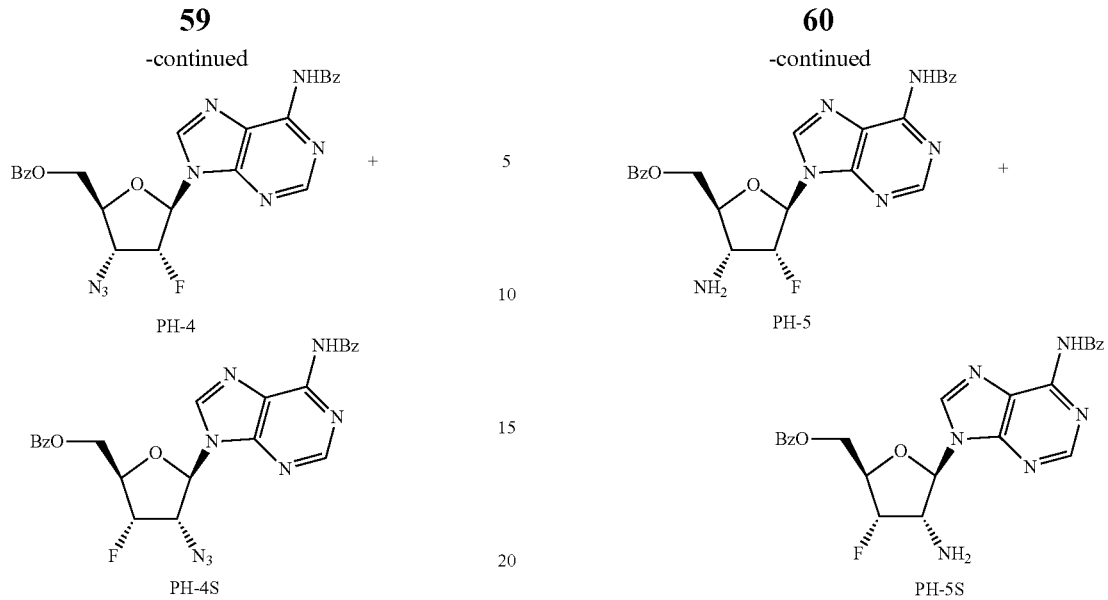

To a solution of PH-3 and PH-3S (5:1) (10 g, 19.98 mmol, 1.00 equiv) in tetrahydrofuran (100 mL) with an inert atmosphere of nitrogen, was added 1, 8-Diazabicyclo [5.4.0] undec-7-ene (10.69 g, 70.22 mmol, 3.50 equiv). This was followed by the addition of perfluorobutylsulfonyl fluoride (12.69 g, 2.10 equiv) dropwise with stirring at 0° C. in 10 min. The resulting solution was stirred for 1.5 h at 0° C. The resulting solution was diluted with 200 mL of dichloromethane. The resulting mixture was washed with 3×200 mL of water, 1×200 mL of saturated sodium bicarbonate solution and 1×200 mL of saturated sodium chloride solution respectively. The mixture was dried over anhydrous sodium sulfate, filtered, and concentrated under reduced pressure. The crude product was re-crystallized from ethyl acetate/petroleum ether in the ratio of 1:1. This resulted in 6 g (60%) of PH-4 and PH-4S (5:1) as a white solid. MS m/z [M+H]+ (ESI): 503.

Preparation of PH-5

To a solution of PH-4 and PH-4S (5:1) (10 g, 19.90 mmol, 1.00 equiv) in tetrahydrofuran (150 mL), was added 10% palladium carbon (3.0 g). The flask was evacuated and flushed three times with nitrogen, followed by flushing with hydrogen. The resulting solution was stirred for 1 h at room temperature. The solids were filtered out. The resulting mixture was concentrated under reduced pressure. The crude product (10 g) was purified by Flash-Prep-HPLC with the following conditions (IntelFlash-1): Column, C18; mobile phase, waters and acetonitrile (30% acetonitrile up to 50% in 30 min); Detector, UV 254 nm. This resulted in 7 g (74%) of PH-5 as a white solid and 1.0 g of PH-5S as a white solid. MS m/z [M+H]+(ESI): 477.

Preparation of PH-6

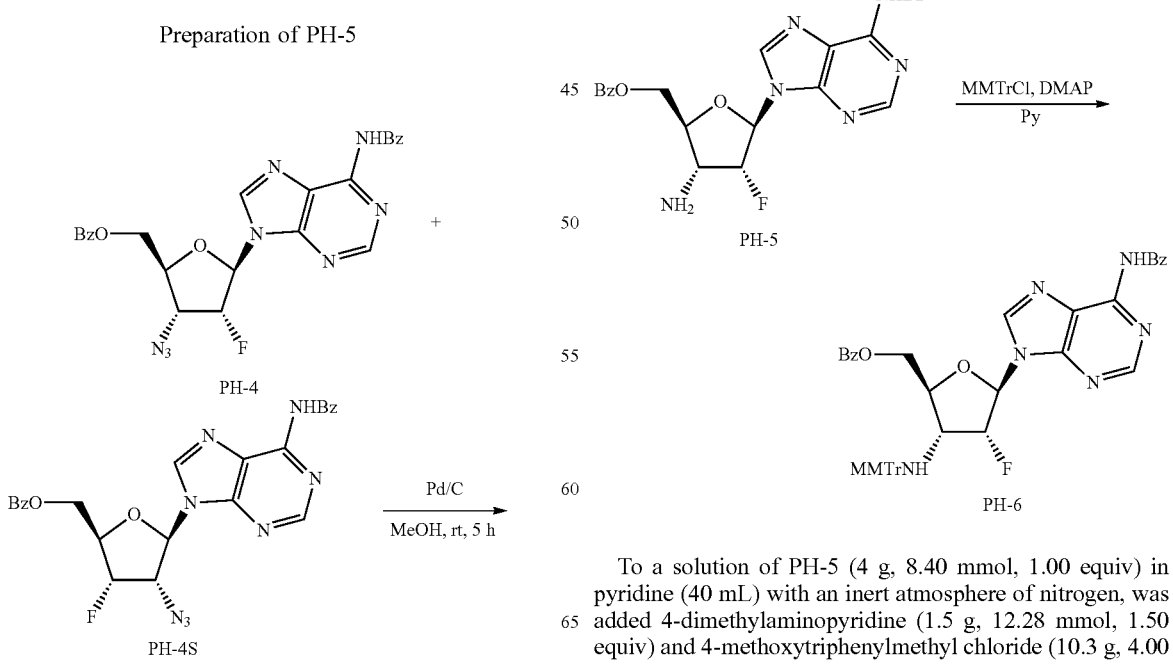

To a solution of PH-5 (4 g, 8.40 mmol, 1.00 equiv) in pyridine (40 mL) with an inert atmosphere of nitrogen, was added 4-dimethylaminopyridine (1.5 g, 12.28 mmol, 1.50 equiv) and 4-methoxytriphenylmethyl chloride (10.3 g, 4.00 equiv) in order. The resulting solution was stirred for 16 h at 25° C. The resulting solution was diluted with 300 mL of dichloromethane. The resulting mixture was washed with 1×300 mL of water and 3×300 mL of saturated sodium bicarbonate solution. The resulting mixture was washed with 1×300 mL of saturated sodium chloride solution respectively. The mixture was dried over anhydrous sodium sulfate, filtered, and concentrated under reduced pressure. The residue was applied onto a silica gel column with dichloromethane/methanol (100/1). This resulted in 5.7 g (91%) of PH-6 as a white solid.

Preparation of PH-7

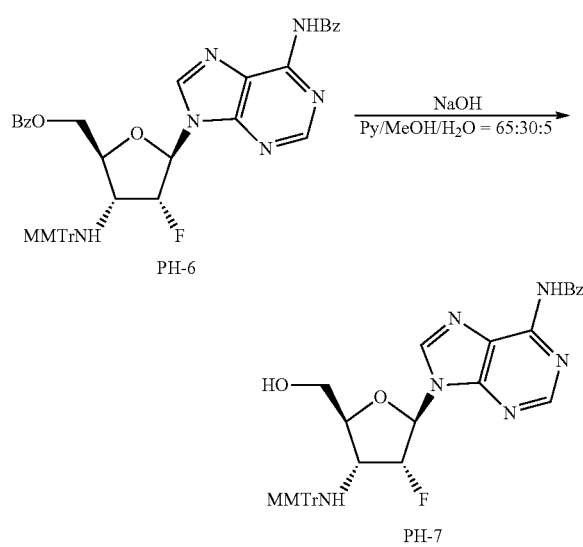

To a solution of PH-6 (5 g, 6.68 mmol, 1.00 equiv) in pyridine/methanol/water (32.2/14.7/2.4 mL), was added sodium hydroxide (2 mol/L) (7.2 mL, 1.10 equiv) dropwise with stirring at 0° C. in 5 min. The resulting solution was stirred for 20 min at 0° C. The reaction was then quenched by the addition of 200 mL of ice water. The resulting solution was extracted with 400 mL of dichloromethane and the organic layers combined. The resulting mixture was washed with 1×300 mL of water and 1×300 mL of saturated sodium chloride solution. The mixture was dried over anhydrous sodium sulfate, filtered, and concentrated under reduced pressure. The residue was applied onto a silica gel column with methanol/dichloromethane (1:100). This resulted in 4.3 g (100%) of PH-7 as a white solid. MS m/z [M+H]+(ESI): 645.

Preparation of PH-8

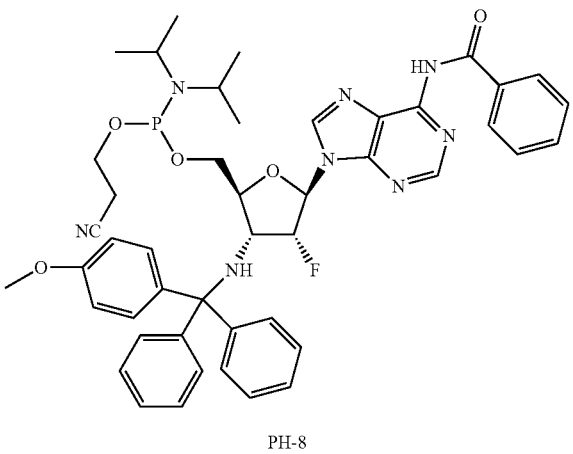

To a solution of PH-7 (19.4 g, 35.89 mmol, 1.00 equiv) in dichloromethane (200 mL) with an inert atmosphere of nitrogen, was added 3-([bis [bis (propan-2-yl) amino] phosphanyl] oxy) propanenitrile (11.79 g, 39.12 mmol, 1.30 equiv). This was followed by the addition of 4, 5-Dicyanoimidazole (4.26 g, 1.20 equiv) at 0° C. The resulting solution was stirred for 30 min at room temperature. The resulting solution was diluted with 1000 mL of dichloromethane. The resulting mixture was washed with 3×800 mL of saturated sodium bicarbonate solution and 1×800 mL of sodium chloride solution respectively. The mixture was dried over anhydrous sodium sulfate, filtered, and concentrated under reduced pressure. The crude product was purified by Flash-Prep-HPLC with the following conditions: Column, C18; mobile phase, waters and acetonitrile (40% acetonitrile up to 80% in 6 min); Detector, UV 254 nm. This resulted in 15.2 g (50%) of PH-8 as a white solid. MS m/z [M+H]+(ESI): 845.

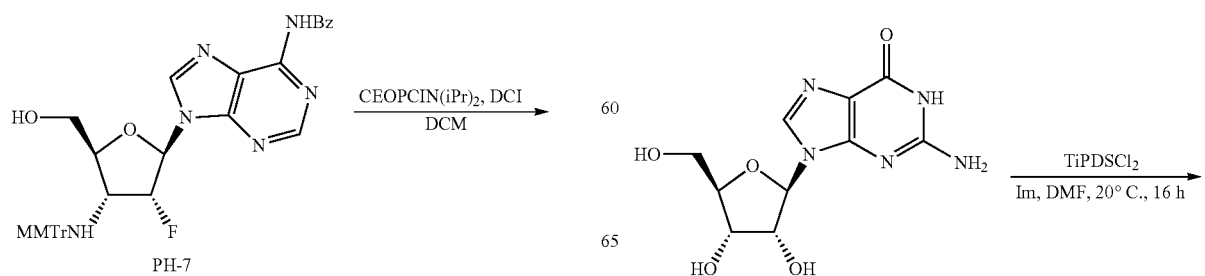

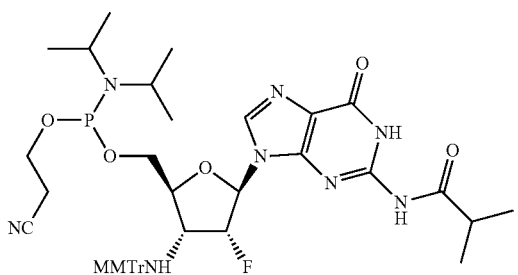

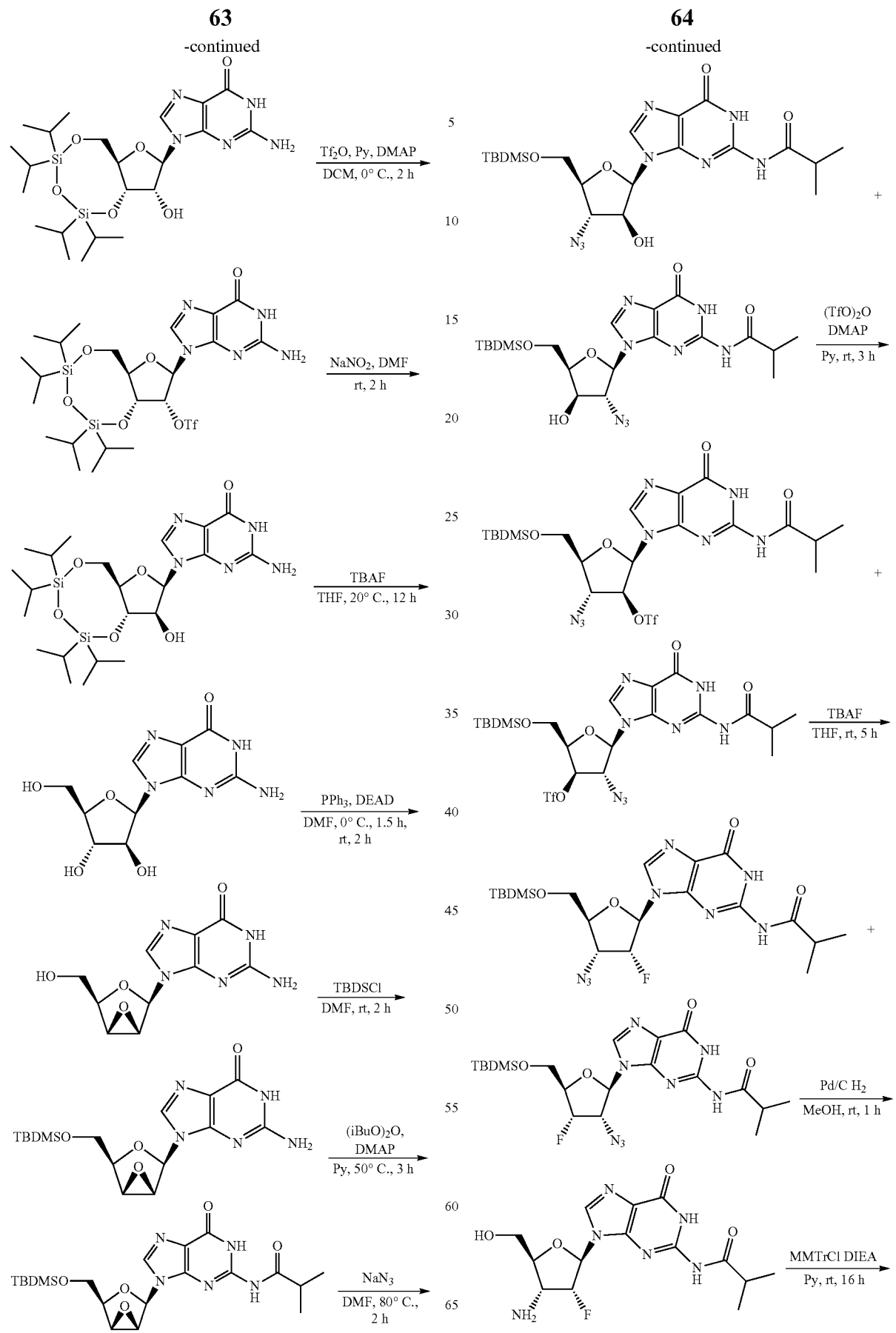

Preparation of PH-11

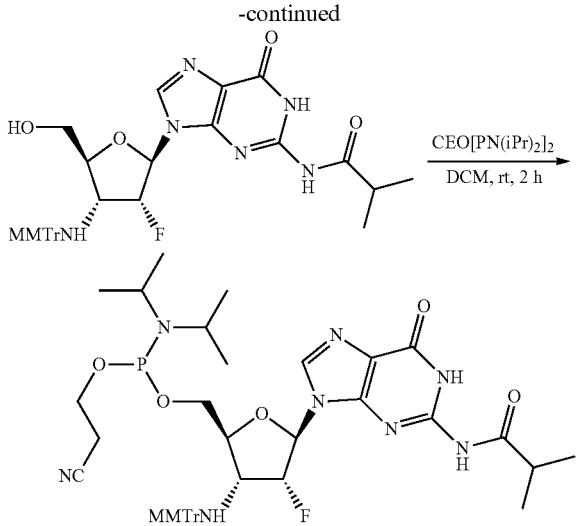

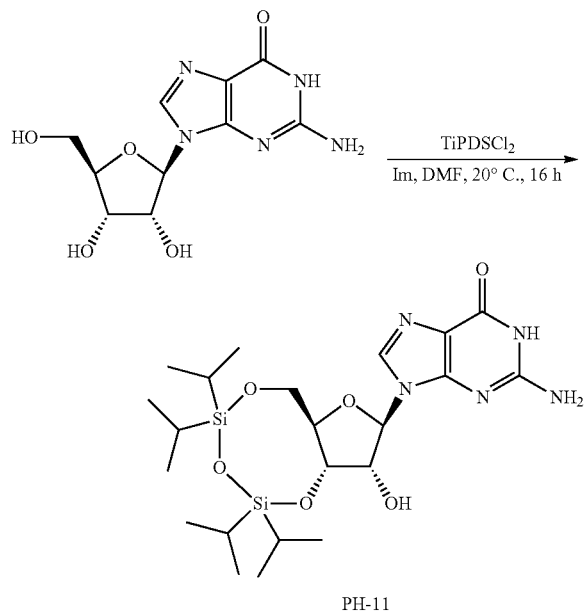

To a solution of 2-amino-9-[(2R,3R,4S,5R)-3,4-dihydroxy-5-(hydroxymethyl)oxolan-2-yl]-6,9-dihydro-1H-purin-6-one (700 g, 2.47 mol, 1.00 equiv) in N,N-dimethylformamide (7 L) with an inert atmosphere of nitrogen, was added imidazole (504 g, 7.41 mol, 3.00 equiv). This was followed by the addition of 1, 3-Dichloro-1, 1, 3, 3-tetraisopropyldisiloxane (770 g, 2.44 mol, 1.00 equiv) dropwise with stirring at 20° C. The resulting solution was stirred for 16 h at 20° C. The reaction solution was then poured into 70 L of water/ice. The solids were collected by filtration. This resulted in 1200 g (92%) of PH-11 as a white solid. MS m/z [M+H]+(ESI): 526.

Preparation of PH-12

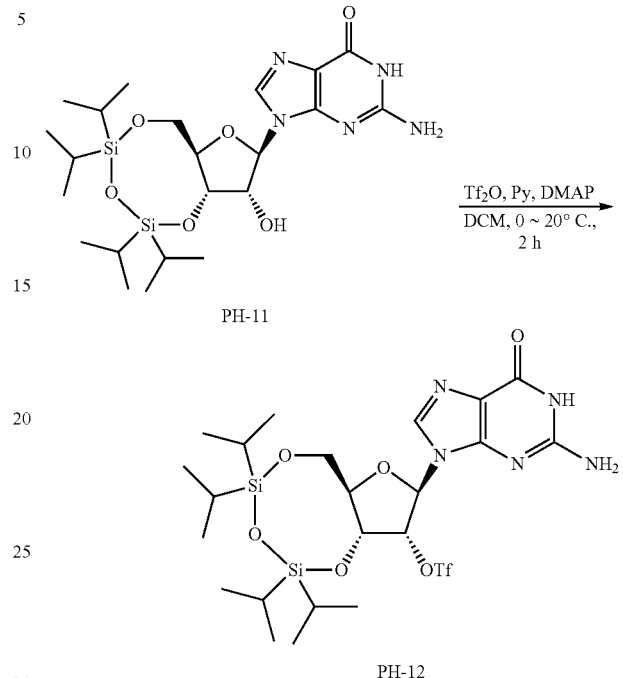

To a solution of PH-11 (530 g, 1.0 mol, 1.00 equiv) in dichloromethane (5000 mL) with an inert atmosphere of nitrogen, was added pyridine (725 g, 9.17 mol, 9.00 equiv) and 4-dimethylaminopyridine (147 g, 1.20 mol, 1.20 equiv) in order. This was followed by the addition of trifluoromethanesulfonic anhydride (426 g, 1.51 mol, 1.20 equiv) dropwise with stirring at 0° C. The resulting solution was stirred for 15 min at 0° C. Then the resulting solution was allowed to react with stirring, for an additional 2 h at 20° C. The resulting solution was diluted with 5000 mL of dichloromethane. The resulting solution was washed with 2×3000 mL of saturated sodium bicarbonate and 1×3000 mL of saturated sodium chloride respectively. The solution was dried over anhydrous sodium sulfate, filtered, and concentrated under reduced pressure. This resulted in 600 g (90%) of PH-12 as a brown solid.

The product was used in the next step directly without further purification.

Preparation of PH-13

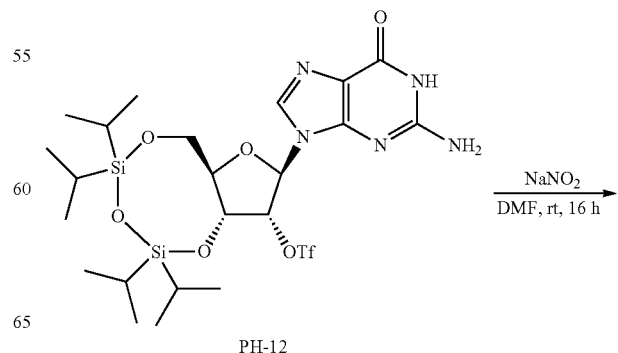

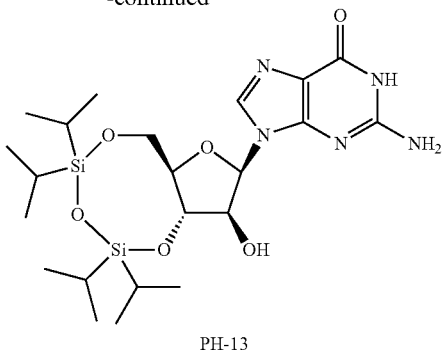

PH-13

To a solution of PH-12 (200 g, 304.04 mmol, 1.00 equiv) in N,N-dimethylformamide (1000 mL) with an inert atmosphere of argon, was added sodium nitrite (115 g, 1.67 mol, 5.00 equiv). The resulting mixture was stirred for 16 h at 25° C. The resulting solution was poured into 5000 ml water/ice. The solids were collected by filtration. The crude product was re-crystallized from dichloromethane/acetonitrile in the ratio of 1/4 (50 ml/g). This resulted in 78 g (49% over last two steps) of PH-13 as a solid. MS m/z [M+H]+(ESI): 526.

Preparation of PH-14

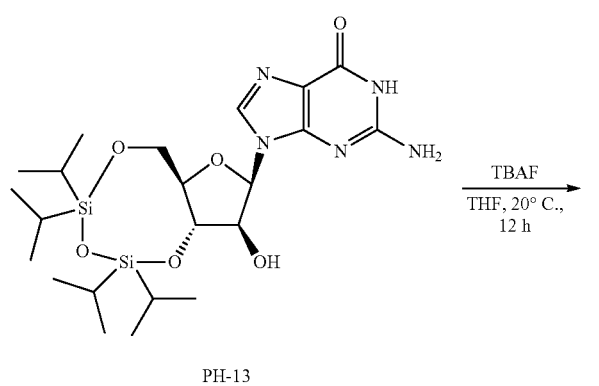

To a solution of PH-13 (50 g, 95.10 mmol, 1.00 equiv) in tetrahydrofuran (500 mL) with an inert atmosphere of nitrogen, was added tetrabutylammonium fluoride (95 mL, 1.00 equiv, 1N in tetrahydrofuran). The resulting mixture was stirred for 12 h at 20° C. The resulting mixture was concentrated under reduced pressure. The crude was re-crystallized from methanol/ethyl acetate in the ratio of 1/5 (20 ml/g) three times. The solids were collected by filtration, and then purified by Flash with the following conditions: Column, C18 silica gel; mobile phase, waters and acetonitrile (2% acetonitrile up to 10% in 10 min); Detector, UV 254 nm. This resulted in 16 g (59%) of PH-14 as a brown solid. 1H-NMR (DMSO-d₆, 400 MHz): 10.44 (s, 1H), 6.49 (s, 2H), 6.02 (s, 1H), 5.55-5.65 (m, 2H), 5.10 (s, 1H), 4.08 (m, 2H), 3.76 (m, 1H), 3.64 (m, 1H).

Preparation of PH-15

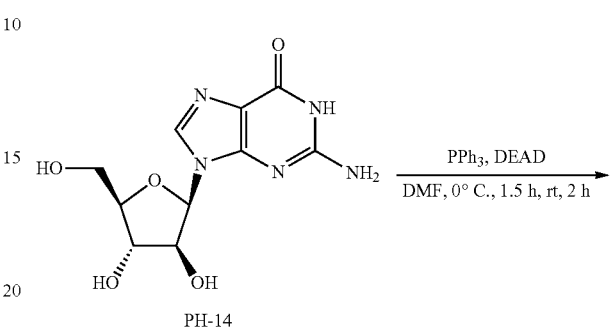

To solution of PH-14 (220 g, 776.72 mmol, 1.00 equiv) in N,N-dimethylformamide (2000 mL) with an inert atmosphere of argon, was added triphenylphosphine (509 g, 1.94 mol, 2.50 equiv). The resulting solution was stirred for 1.5 h at 0° C. To this was added diethyl azodicarboxylate (338 g, 1.94 mol, 2.50 equiv) dropwise with stirring at 0° C. The resulting solution was stirred for 2 h at room temperature. The resulting mixture was poured into 20 L cold ethyl ether. The solids were collected by filtration, then re-crystallized from methanol/ethyl acetate in the ratio of 1/10 (10 ml/g). This resulted in 100 g (49%) of PH-15 as a brown solid. MS m/z [M+H]+(ESI): 266.

Preparation of PH-16

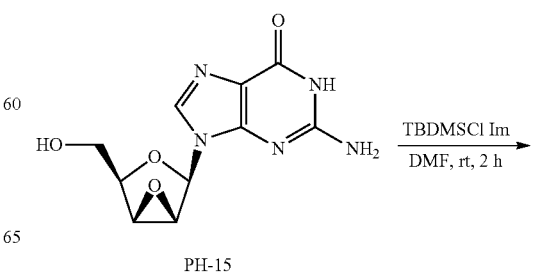

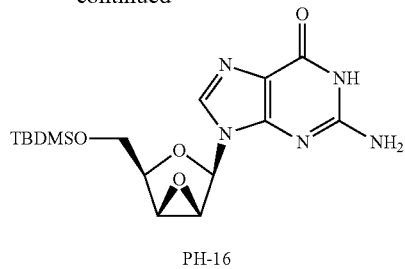

PH-16

To a solution of PH-15 (100 g, 377.0 mmol, 1.00 equiv) in N,N-dimethylformamide (1000 mL) with an inert atmosphere of nitrogen, was added imidazole (77 g, 1.131 mol, 3.00 equiv). This was followed by the addition of tert-butyldimethylsilyl chloride (142 g, 942 mmol, 1.50 equiv.) dropwise with stirring at 0° C. The resulting solution was stirred for 2 h at room temperature. The reaction was then quenched by the addition of methanol. The resulting mixture was concentrated under reduced pressure. The residue was applied onto a silica gel column with dichloromethane/methanol (100:1~15:1). This resulted in 80 g (85%) of PH-16 as a solid. MS m/z [M+H]+(ESI): 380.

Preparation of PH-17

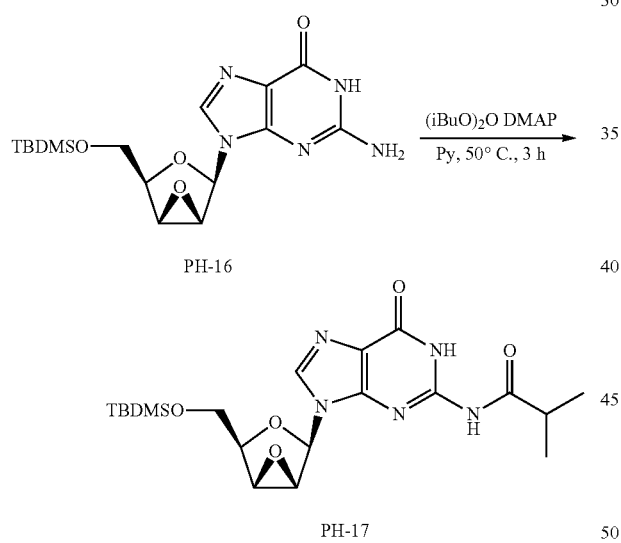

To a solution of PH-16 (73 g, 192.37 mmol, 1.00 equiv) in pyridine (730 mL) with an inert atmosphere of nitrogen, was added 4-dimethylaminopyridine (23.5 g, 192.35 mmol, 0.50 equiv). This was followed by the addition of isobutyric anhydride (213 g, 1.35 mol, 5.00 equiv) dropwise with stirring. The resulting solution was stirred for 3 h at 50° C. The reaction was then quenched by the addition of ice water. The resulting solution was extracted with 3×2000 mL of dichloromethane and the organic layers combined. The resulting mixture was washed with 3×2000 mL of saturated sodium bicarbonate, 3×2000 mL of water and 3×2000 mL of saturated sodium chloride respectively. The organic layers were dried over anhydrous sodium sulfate, filtered, and concentrated under reduced pressure. The residue was applied onto a silica gel column with dichloromethane/ methanol (100:1~20:1). This resulted in 52 g (60%) of PH-17 as a yellow solid. MS m/z [M+H]+(ESI): 450.

Preparation of PH-18

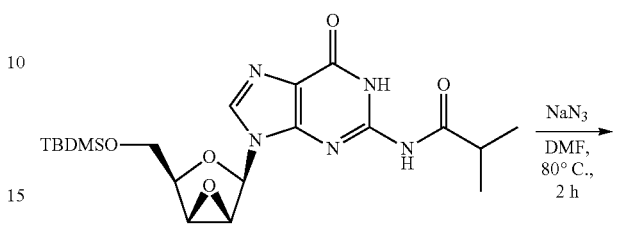

PH-17

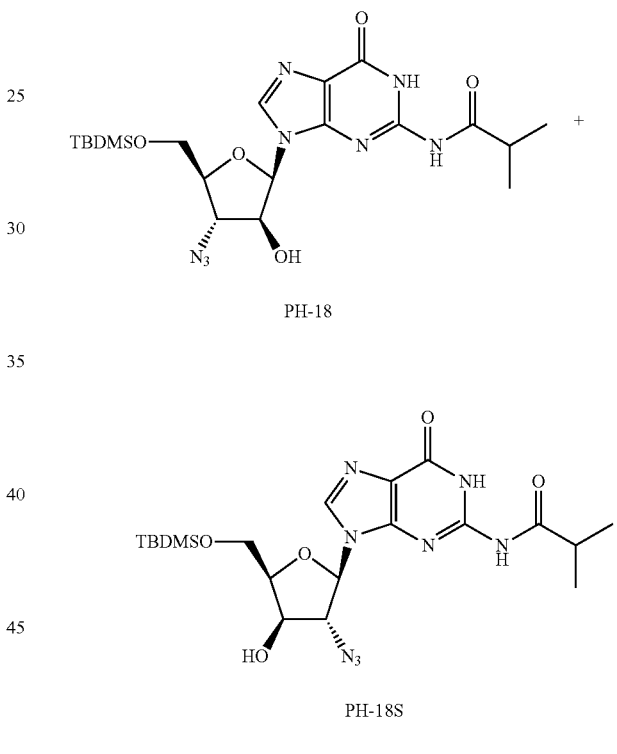

To a solution of PH-17 (20 g, 44.4 mmol, 1.00 equiv) in N, N-dimethylformamide (100 mL) with an inert atmosphere of nitrogen was added sodium azide (18 g, 267 mmol, 6.00 equiv). The resulting solution was stirred for 2 h at 80° C. The resulting mixture was diluted with 1000 mL of dichloromethane. The resulting solution was washed with 3×1000 mL of saturated sodium bicarbonate, 3×1000 mL of water and 3×1000 mL of saturated sodium chloride respectively. The solution was dried over anhydrous sodium sulfate and concentrated under reduced pressure. The residue was applied onto a silica gel column with dichloromethane/ methanol (100/1~40/1). This resulted in 11 g (50%) of PH-18/PH-18S (5.2:1) as a yellow solid. MS m/z [M+H]+ (ESI): 493

Preparation of PH-19

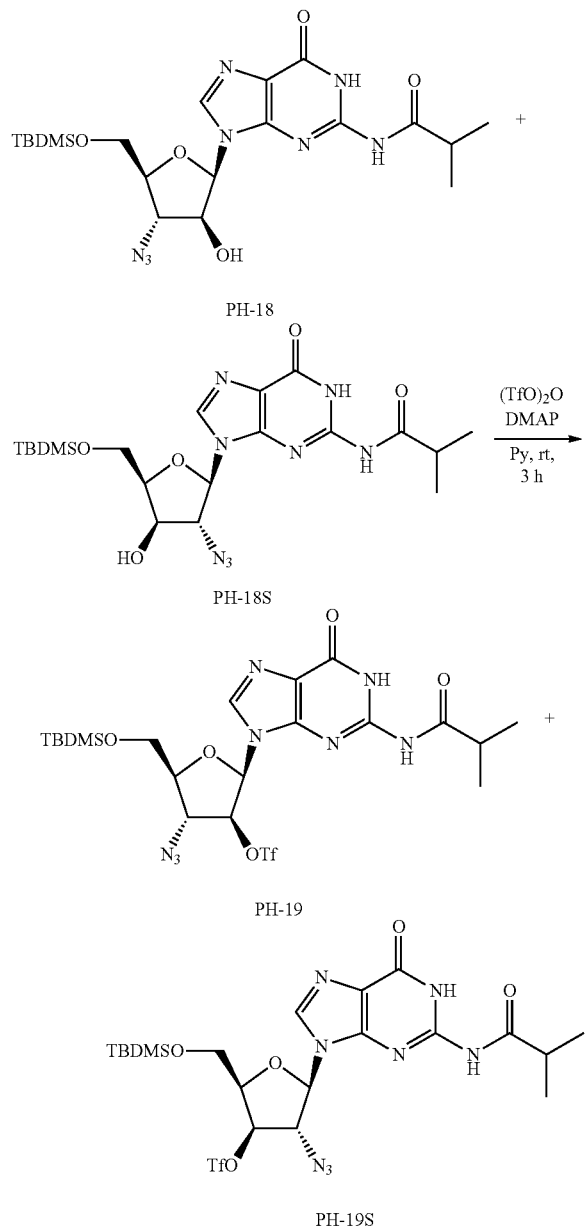

PH-18

PH-18S

PH-19

PH-19S

To a solution of PH-18/PH-18S (5.2:1) (16 g, 37.87 mmol, 1.00 equiv) in dichloromethane (160 mL), was added pyridine (23 g, 290.77 mmol, 9.00 equiv) and dimethylaminopyridine (4.35 g, 35.66 mmol, 1.20 equiv). This was followed by the addition of 1, 3-bis (trifluoromethylsulfonyl) trioxidane (11.9 g, 37.88 mmol, 1.20 equiv) dropwise with stirring at 0° C. The resulting solution was stirred for 2 h at 20° C. The reaction was quenched by the addition of water/ice. The resulting mixture was extracted with 2×1000 mL of dichloromethane and the organic layers combined. The resulting solution was washed with 1×1000 mL of saturated sodium chloride. The resulting solution was concentrated under reduced pressure. This resulted in 16 g (68%) of PH-19/PH-19S as a brown solid. The product was used in the next step directly without further purification.

Preparation of PH-20

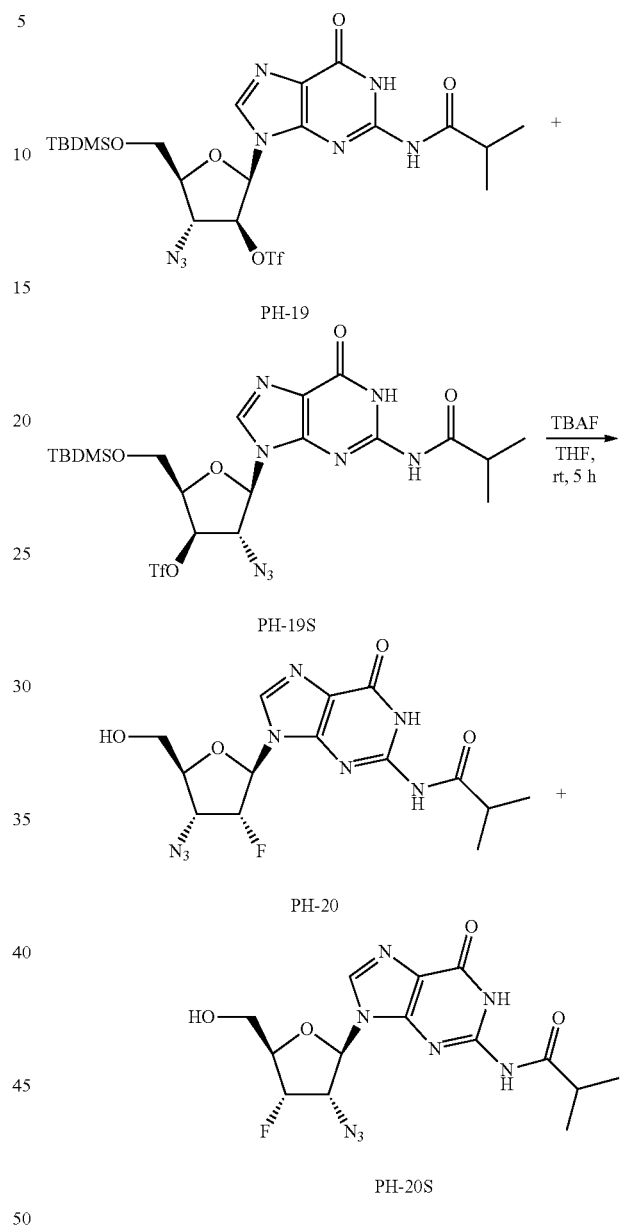

PH-19

PH-19S

PH-20

PH-20S

To a solution of PH-19/PH-19S (16 g, 25.61 mmol, 1.00 equiv) in tetrahydrofuran (160 mL) with an inert atmosphere of argon, was added tetrabutylammonium fluoride (100 mL, 5.00 equiv) dropwise with stirring at 0° C. The resulting solution was stirred for 5 h at room temperature. The resulting solution was diluted with 1000 mL of dichloromethane. The resulting solution was washed with 1×500 mL of water and 1×500 mL of saturated sodium chloride respectively. The resulting solution was concentrated under reduced pressure. The residue was applied onto a silica gel column with dichloromethane/methanol (100/1~20/1). This resulted in 8 g (85%) of PH-20/PH-20S (7:1) a yellow solid. MS m/z [M+H]+(ESI): 381.

Preparation of PH-21

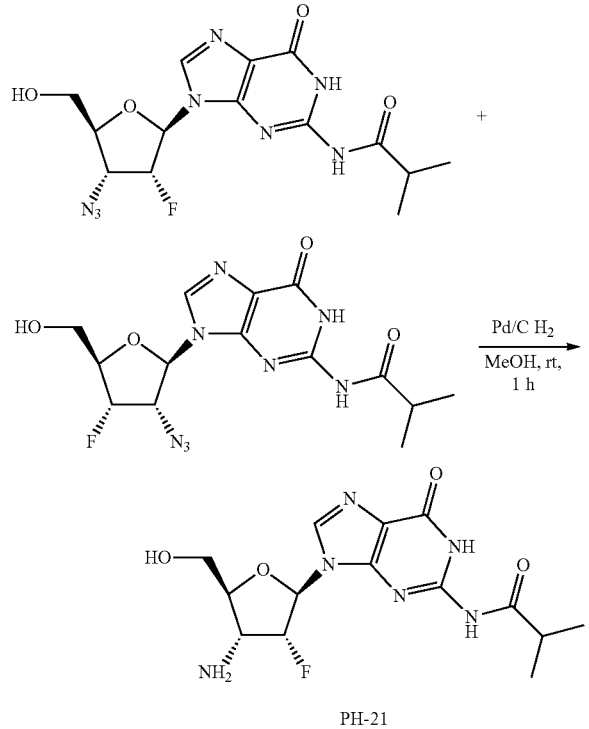

PH-21

To a solution of PH-20/PH-20S (3.4 g, 8.94 mmol, 1.00 equiv) in methanol (50 mL) was added 10% palladium carbon (1.7 g). The flask was evacuated and flushed three times with nitrogen, followed by flushing with hydrogen. The resulting solution was stirred for 1 h at room temperature. The resulting solution was diluted with 100 mL of methanol. The solids were filtered out. The resulting solution was concentrated under reduced pressure. The crude product was purified by Flash-Prep-HPLC with the following conditions: Column, C18 silica gel; mobile phase, waters and acetonitrile (5% acetonitrile up to 50% in 35 min); Detector, UV 254 nm. This resulted in 1.7 g (54%) of PH-21 as a white solid. 1H-NMR (DMSO-$d_6$, 400 MHz): 12.13 (s, 1H), 11.91 (s, 1H), 8.91 (s, 2H), 8.23 (s, 2H), 7.25 (m, 1H), 5.78 (m, 1H), 4.62-3.72 (m, 4H), 2.92 (m, 1H), 1.13 (s, 6H).

Preparation of PH-22

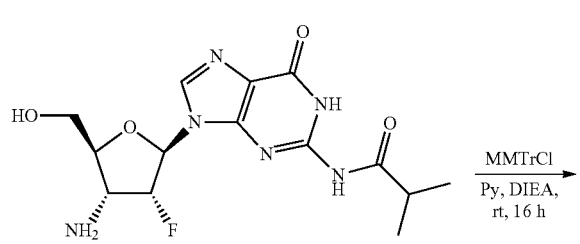

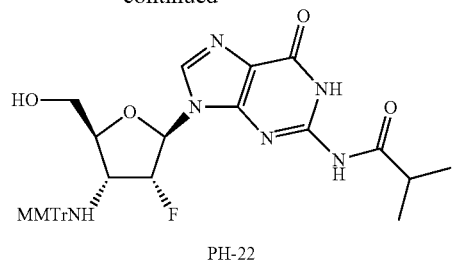

PH-22

To a solution of PH-21 (6.0 g, 16.95 mmol, 1.00 equiv) in pyridine/N,N-diisopropylethylamine (100/20 mL) with an inert atmosphere of argon, was added 1-(chlorodiphenylmethyl)-4-methoxybenzene (6.24 g, 20.34 mmol, 1.20 equiv). The resulting solution was stirred for 16 h at room temperature. The resulting solution was diluted with 1000 ml of dichloromethane. The resulting solution was washed with 1×250 mL of saturated sodium bicarbonate, 1×250 ml of water and 1×250 mL of saturated sodium chloride respectively. The residue was applied onto a silica gel column with dichloromethane/methanol (100/1-50/1). This resulted in 13 g (74%) of PH-22 as a white solid. 1H-NMR (DMSO-$d_6$, 400 MHz): 12.15 (s, 1H), 11.70 (s, 1H), 8.14 (s, 1H), 7.49 (m, 4H), 7.24 (m, 6H), 7.15 (m, 2H), 6.72 (m, 2H), 5.82 (m, 1H), 5.30 (m, 1H), 4.04 (m, 3H), 3.62 (s, 3H), 3.45 (m, 1H), 2.83-2.62 (m, 3H), 1.10 (m, 6H).

Preparation of PH-23

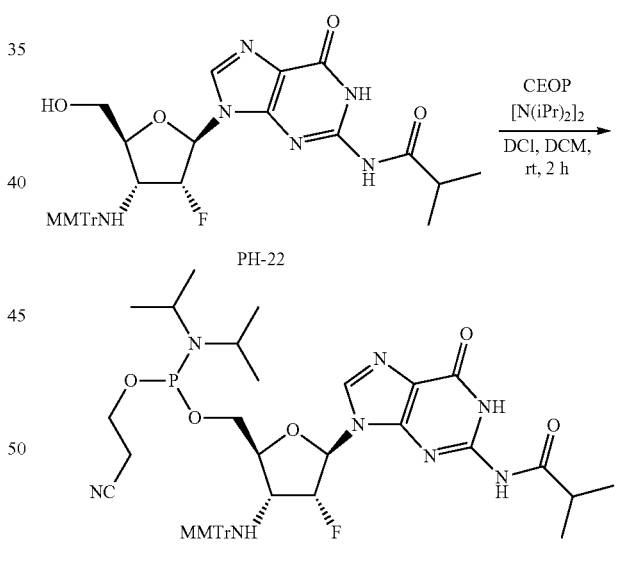

PH-23

To a solution of PH-22 (7.8 g, 12.45 mmol, 1.00 equiv.) in dichloromethane (80 mL) with an inert atmosphere of argon, was added 3-(bis[bis(propan-2-yl)amino]phosphanyloxy)propanenitrile (7.5 g, 24.92 mmol, 2.00 equiv.) and 4,5-dicyanoimidazole (2.2 g, 18.63 mmol, 1.50 equiv.) in order. The resulting solution was stirred for 2 h at room temperature. The resulting mixture was diluted with 1000 mL of dichloromethane. The resulting solution was washed with 3×250 mL of saturated sodium bicarbonate, 3×250 mL of water and 3×250 mL of saturated sodium chloride respectively. The resulting solution was concentrated under reduced pressure. The crude product was purified by Flash-Prep-HPLC with the following conditions: Column, C18 silica gel; mobile phase, waters and acetonitrile (40% acetonitrile up to 95% in 35 min); Detector, UV 254 nm. This resulted in 8.06 g (78%) of PH-23 as a white solid. MS m/z [M+H]+(ESI): 827.

2'-F-3'-NHTr Building Blocks for Oligomer Synthesis

The 2'-O-Me 3'-NH-MMTr-5'-O-(2-cyanoethyl-N,N-diisopropyl) phosphoramidite monomers of 6-N-benzoyladenosine ($A^{Bz}$), 4-N-Benzylcytidine ($C^{Bz}$), 2-N-isobutyrylguanosine ($G^{iBu}$), and Uridine (U) as shown below were synthesized using the procedure described in WO 200118015 A1

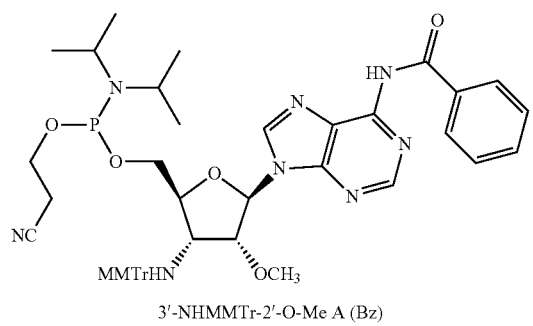

3'-NHMMTr-2'-O-Me A (Bz)

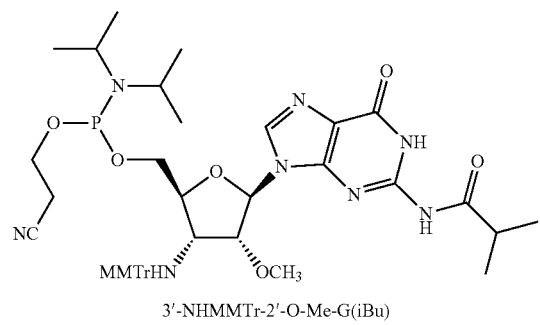

3'-NHMMTr-2'-O-Me-G(iBu)

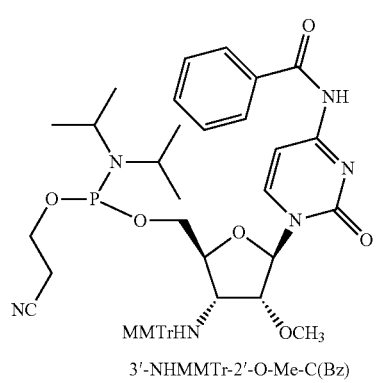

3'-NHMMTr-2'-O-Me-C(Bz)

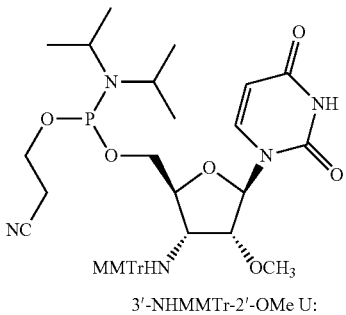

3'-NHMMTr-2'-OMe U:

2'-O-Me-3'-NHTr Building Blocks for Oligomer Synthesis

Exemplary phosphoroamidates include:

| Raw material description |
|---|
| 3'-NHTr-dA(Bz) |
| 3'-NHTr-dC(Bz) |
| 3'-NHTr-dG(iBu) |
| 3'-NHTr-T: |
| 3'-NHMMTr-2'-F-A(NH-Bz) |
| 3'-NHMMTr-2'-F-C(NH-Bz) |
| 3'-NHMMTr-2'-F-G(NH-iBu) |
| 3'-NHMMTr-2'-F-U: |
| 3'-NHMMTr-2'-OMe-A(NH-Bz) |
| 3'-NHMMTr-2'-OMe-C(NH-Bz) |
| 3'-NHMMTr-2'-OMe-G(NH-iBu) |
| 3'-NHMMTr-2'-OMe U: |
| 3'-NHTr (dA, dC, dG and dT)-CPG 500 Å: |
| Loading: 64-83 µmol/g |

The reverse phosphoramidite 3'-O-DMT-deoxy Adenosine (NH-Bz), 5'-O-(2-cyanoethyl-N,N-diisopropyl phosphoramidite, 3'-O-DMT-deoxy Guanosine (NH-ibu), 5'-O-(2-cyanoethyl-N,N-diisopropyl phosphoramidite, 3'-O-DMT-deoxy Cytosine (NH-Bz), 5'-O-(2-cyanoethyl-N,N-diisopropyl phosphoramidite, 3'-O-DMT-deoxy Thymidine (NH-Bz), 5'-O-(2-cyanoethyl-N,N-diisopropyl phosphoramidite and reverse solid supports were purchased from commercially-available sources (Chemgenes).

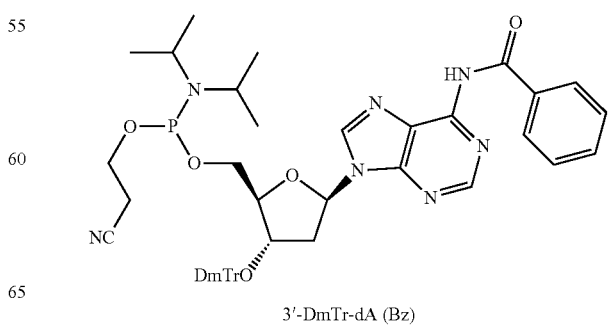

3'-DmTr-dA (Bz)

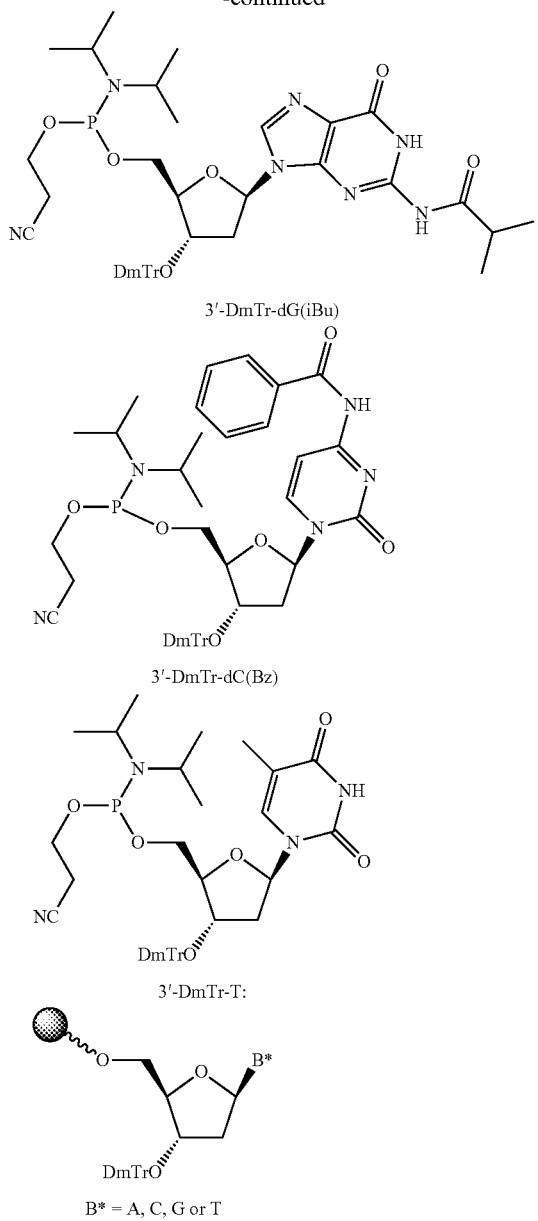

3'-DmTr-dG(iBu)

3'-DmTr-dC(Bz)

3'-DmTr-T:

B* = A, C, G or T

Reverse DNA Building Blocks for Oligomer Synthesis

Exemplary reverse phosphoroamidites used for this disclosure include:

| Raw material description |
| --- |
| 3'-O-DMTr-2'-OMe-A(NH-Bz) |
| 3'-O-DMTr-2'-OMe-C(NH-Bz) |
| 3'-O-DMTr-2'-OMe-G(NH-iBu) |
| 3'-O-DMTr-2'-OMe-U: |
| 3'-ODMTr (dA, dC, dG and dT)-CPG 500 Å: Loading: 64-83 µmol/g |

For making the oligomers with the following modifications: 2'-F—NPS—PS-2'-F—NPS; 2'-F—NP—PS-2'-F—NP; 2'-OMe-NP—PS-2'-OMe-NP; 2'-OMe-NPS-DNA-PS-2'-OMe-NPS, the synthesis was carried out on a 1 µM scale in a 5' to 3' direction with the 5'-phosphoramidite monomers diluted to a concentration of 0.1 M in anhydrous CH$_3$CN in the presence of 5-(benzylthio)-1H-tetrazole activator (coupling time 2.0-4.0 min) to a solid bound oligonucleotide followed by standard capping, oxidation and deprotection afforded modified oligonucleotides. The stepwise coupling efficiency of all modified phosphoramidites was more than 98%. The DDTT (dimethylamino-methylidene) amino)-3H-1, 2, 4-dithiazaoline-3-thione was used as the sulfur-transfer agent for the synthesis of oligoribonucleotide phosphorothioates. Oligonucleotide-bearing solid supports were heated at room temperature with aqueous ammonia/Methylamine (1:1) solution for 3 h in shaker to cleavage from support and deprotect the base labile protecting groups.

Examples 1-4

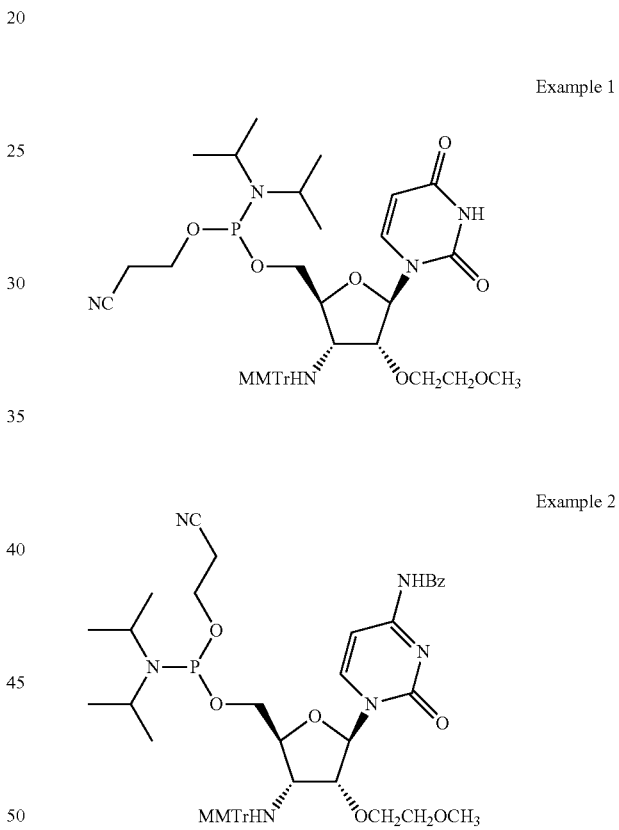

Example 1

Example 2

Example 3

Example 4

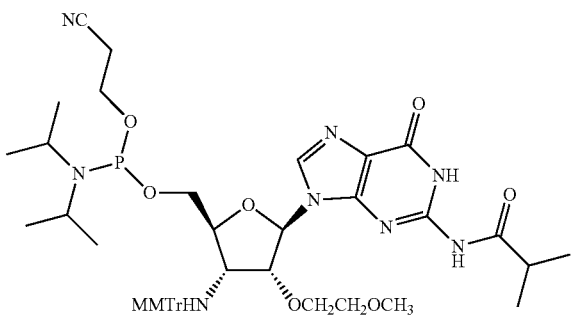

The appropriately protected 2'-O-methoxy ethyl-3'-aminonucleoside-5'-phosphoramidite building blocks (examples 1-4 were prepared after chemical transformations shown in Schemes 1-4.

First for synthesis of uracil based 3'-NH-MMTr-2'-O-methoxyethyl phosphoramidites example 5, key 3'-azido-2'-methoxyethyl intermediate 3 was obtained in low yields via an-hydro intermediate 2 as shown in scheme 1.

Due to low yielding alkylation, 3-1 was reacted with BOMCl/DBU to give N-3 protected intermediate 3-4, which was alkylated by using 2-bromoethyl methyl ether/Ag$_2$O/NaI/DMF to give 2'-O-methoxyethyl derivative 3-5 as shown below in scheme 1. Deprotection of N-3-BOM group using hydrogenation condition (Pd/C/H$_2$) resulted in 10-20% desired 3'-amino intermediate 3-6a along with significant over reduced side product 3-6b.

Scheme 1

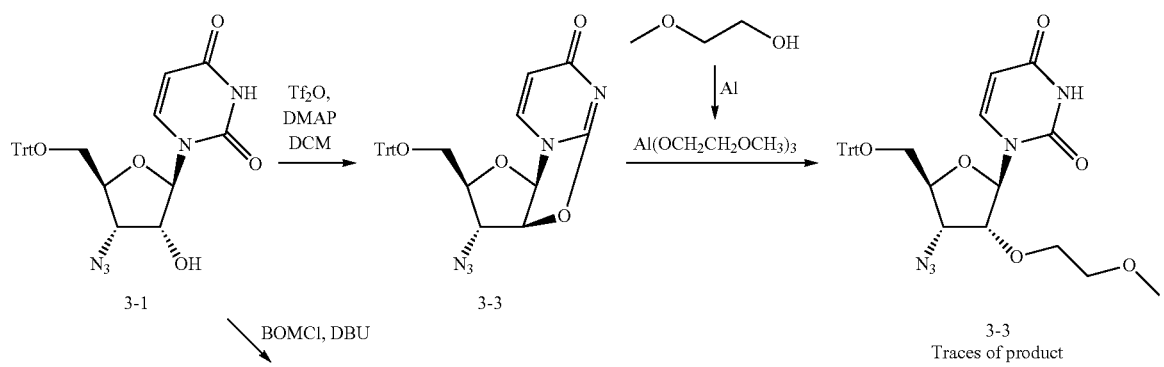

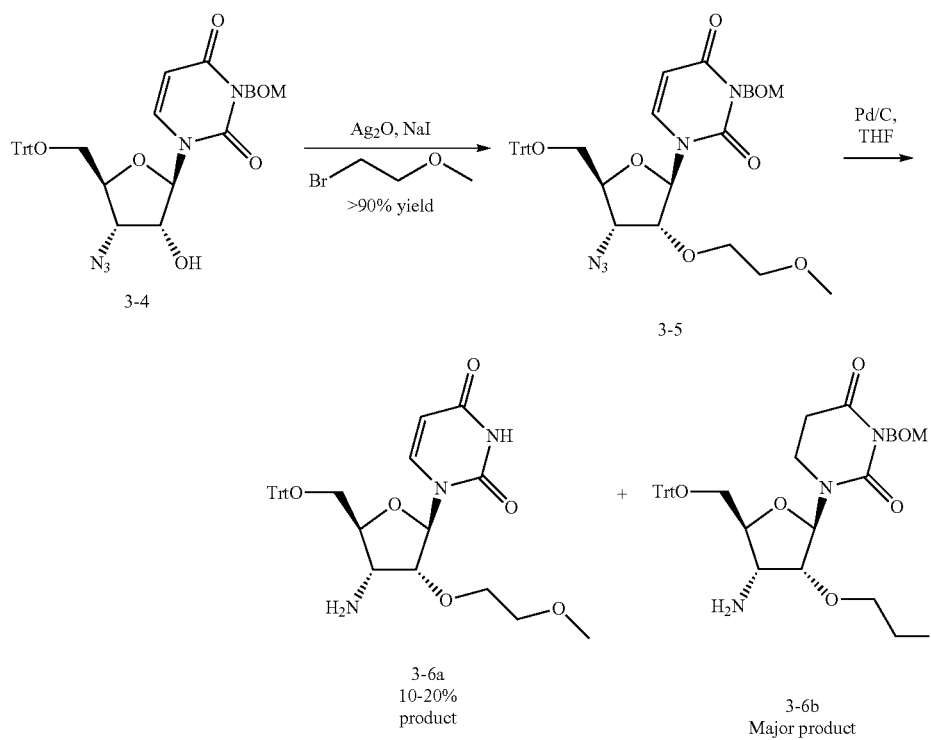

2'-O-alkylation in high yield is obtained as shown below in scheme 2. For this purpose, 3-1 was treated with PMBCl/DBU/DMF to give N-3 protected intermediate 4-2, which was subjected for 2'-O alkylation using 2-bromoethyl methyl ether/Ag$_2$O/NaI/DMF to give 2'-O-methoxyethyl derivative 4-3. Then, 5'-de-tritylation of 4-3 and re-protection of 5'-hydroxyl group using benzoyl chloride afforded 4-5.

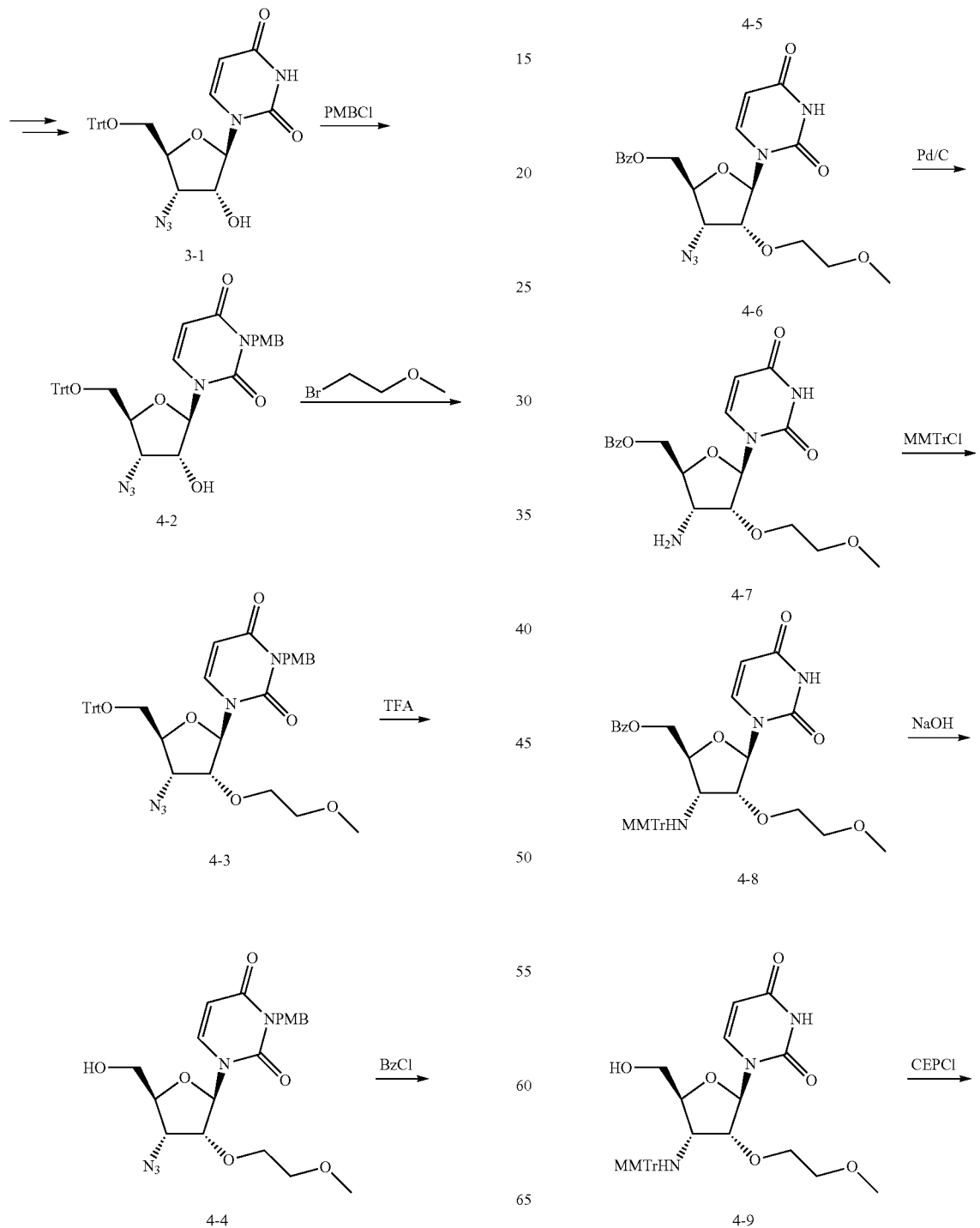

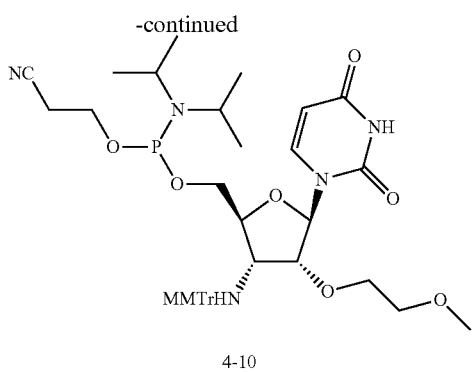

4-10

De-protection of PMB group of intermediate 4-5 in mild conditions gives 4-6. 3'-Azido group of intermediate 4-6 was reduced to an amine, which was then immediately protected, such as reaction with 4-monomethoxytritylchloride, to give 4-8. The 5'-benzyl ester was then cleaved using an alkaline solution, followed by phosphitylation using known protocols to give the desired 2'-O-methoxyethoxy uridine phosphoramidite monomer 4-10.

Preparation of (4-2): To a solution of 3-1 (45.30 g, 88.56 mmol) in DMF (120.00 mL) was added PMBCl (20.80 g, 132.84 mmol) and DBU (44.61 g, 177.12 mmol), the mixture was stirred at r.t. for 2 h. Water was added, extracted with EA. The organic layer was concentrated and purified by column to give 4-2 (52.00 g, 82.32 mmol) as a white solid. ESI-LCMS: m/z 632.3 [M+H]$^+$.

Preparation of (4-3): To a solution of 4-2 (50.00 g, 79.15 mmol) in DMF (120.00 mL) was added 2-Bromoethyl methyl ether (16.50 g, 118.73 mmol) and Ag$_2$O (18.34 g, 79.15 mmol, 2.57 mL), then NaI (5.93 g, 39.58 mmol) was added. The reaction mixture was stirred at r.t. for 12 h. LC-MS showed work well. Filtered and added water and EA, the organic layer was concentrated and purified by column to give 4-3 (52.00 g, 75.39 mmol) as a colorless oil. ESI-LCMS: m/z 690.4 [M+H]$^+$.

Preparation of (4-4): To a solution of 4-3 (52.00 g, 75.39 mmol) in DCM (200.00 mL) was added TFA (150.00 mL). The mixture was stirred at r.t. for 1 h. The reaction mixture was slowly added to cold NH$_4$OH, extracted with DCM. The organic layer was concentrated and purified to give 4-4 (31.00 g, 69.28 mmol) as a colorless oil. ESI-LCMS: m/z 448.2 [M+H]$^+$. $^1$H-NMR (DMSO-d$_6$, 400 MHz): δ ppm 8.02 (d, J=8.12 Hz, 1H), 7.26-7.23 (m, 2H), 6.87-6.84 (m, 2H), 5.87-5.81 (m, 2H), 5.38 (t, J=5.0 Hz, 1H), 4.96-4.85 (m, 2H), 4.36-4.34 (m, 1H), 4.17-4.14 (m, 1H), 4.00-3.97 (m, 1H), 3.83-3.77 (m, 1H), 3.75-3.72 (m, 1H), 3.71 (s, 3H), 3.70-3.68 (m, 1H), 3.61-3.56 (m, 1H), 3.45-3.43 (m, 2H), 3.18 (s, 3H).

Preparation of (4-5): To a solution of 4-4 (31.00 g, 69.28 mmol) in Pyridine (200.00 mL) was added BzCl (13.14 g, 93.87 mmol), the reaction mixture was stirred at r.t. for 15 min and concentrated and purified by column to give 4-5 (35.10 g, 63.8 mmol) as a white solid. ESI-LCMS: m/z 552.2 [M+H]$^+$.

Preparation of (4-6): To a solution of 4-5 (35.10 g, 63.8 mmol) in acetonitrile (300.00 mL) and water (100.00 mL) was added Ceric ammonium nitrate (105 g, 191.40 mmol), the reaction mixture was stirred at r.t. for 12 h and concentrated and extracted with EA. The organic layer was concentrated and purified by column to give 4-6 (27.5 g, 63.75 mmol) as a yellow solid. ESI-LCMS: m/z 432.2 [M+H]$^+$.

Preparation of (4-7): To a solution of 4-6 (27.50 g, 63.75 mmol) in THF (500.00 mL) was added Pd/C (3.00 g), the reaction mixture was stirred at r.t. for 12 h and filtered and concentrated to give 4-7 (25.00 g, 61.67 mmol) as a yellow solid. ESI-LCMS: m/z 406.2 [M+H]$^+$.

Preparation of (4-8): To a solution of 4-7 (25.00 g, 61.67 mmol) in DCM (300.00 mL) was added MMTrCl (28.49 g, 92.51 mmol) and Collidine (14.95 g, 123.34 mmol), then AgNO$_3$ (15.7 g, 92.5 mmol) was added. The reaction mixture was stirred at r.t. for 1 h., and filtered and the organic layer was washed water, dried over Na$_2$SO$_4$ and purified by silica gel column to give 4-8 (33.00 g, 48.69 mmol) as a yellow solid.

Preparation of (4-9): To a solution of 4-8 (14.50 g, 21.39 mmol) was added 1 N NaOH in methanol (200 mL) in water (20 mL), the reaction mixture was stirred at r.t. for 1 h. and concentrated and extracted with DCM, the organic layer was concentrated and purified by silica gel column to give 4-9 (11.50 g, 20.05 mmol) as a white solid. $^1$H-NMR (DMSO-d$_6$, 400 MHz): δ ppm 11.26 (s, 1H), 7.95 (d, J=8.4 Hz, 1H), 7.47-7.44 (m, 4H), 7.34-7.17 (m, 8H), 6.82 (d, J=8.8 Hz, 2H), 5.50-5.48 (m, 2H), 5.13 (t, J=3.6 Hz, 1H), 4.05-3.98 (m, 3H), 3.78 (s, 3H), 3.52-3.49 (m, 1H), 3.34-3.32 (m, 2H), 3.14 (s, 3H), 3.08-3.04 (m, 1H), 2.89-2.86 (m, 1H), 2.70 (d, J=10.0 Hz, 1H), 1.51 (d, J=4.4 Hz, 1H).

Preparation of (4-10): To a solution of 4-9 (11.50 g, 20.05 mmol) in DCM (100.00 mL) was added DMAP (489.85 mg, 4.01 mmol) and DIPEA (10.36 g, 80.19 mmol, 14.01 mL). Then CEPCl (5.70 g, 24.06 mmol) was added to the solution. The mixture was stirred at r.t. for 30 min. The reaction was quenched with saturated NaHCO$_3$. The organic layer was washed with brine, dried over Na$_2$SO$_4$, concentrated to give the crude product. The crude product was purified by Flash-Prep-HPLC. The product was dissolved in anhydrous toluene and concentrated for three times. Then the product was dissolved anhydrous acetonitrile and concentrated for three times. This resulted in 13 g to give 4-10 as a white solid. MS m/z [M−H]$^-$ (ESI): 772.3; $^1$H-NMR (CDCl$_3$, 400 MHz): 9.01 (s, 1H), 8.07-7.61 (m, 1H), 7.53-7.41 (m, 6H), 7.29-7.15 (m, 5H), 6.79-6.76 (m, 2H), 5.63-5.57 (m, 2H), 4.27-4.15 (m, 2H), 4.06-3.95 (m, 1H), 3.85-3.77 (m, 1H), 3.75 (s, 3H), 3.69-3.35 (m, 7H), 3.23 (d, J=4 Hz, 1H), 2.26-2.91 (m, 3H), 2.59 (t, J=6.4 Hz, 1H), 1.75-1.39 (m, 1H), 1.21-1.11 (m, 12H). $^{31}$PNMR (162 MHz, CDCl$_3$): 149.10, 148.26.

Example 5

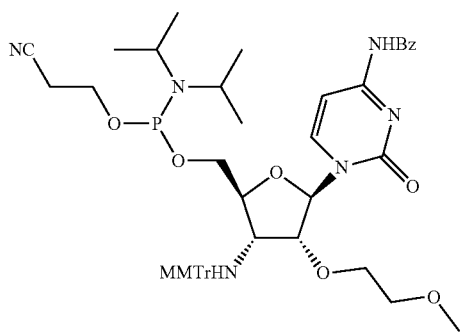

5-4

The 2'-O-methoxyethoxy-NH-benzoyl-cytosine phosphoramidite compound 5-4 was obtained by conversion of uridine intermediate 4-8 into 3'-amino cytidine analogue 5-1 followed by phosphitylation using known protocols to give the desired 2'-O-methoxyethoxy cytidine phosphoramidite monomer 5-4 as shown below in scheme 3.

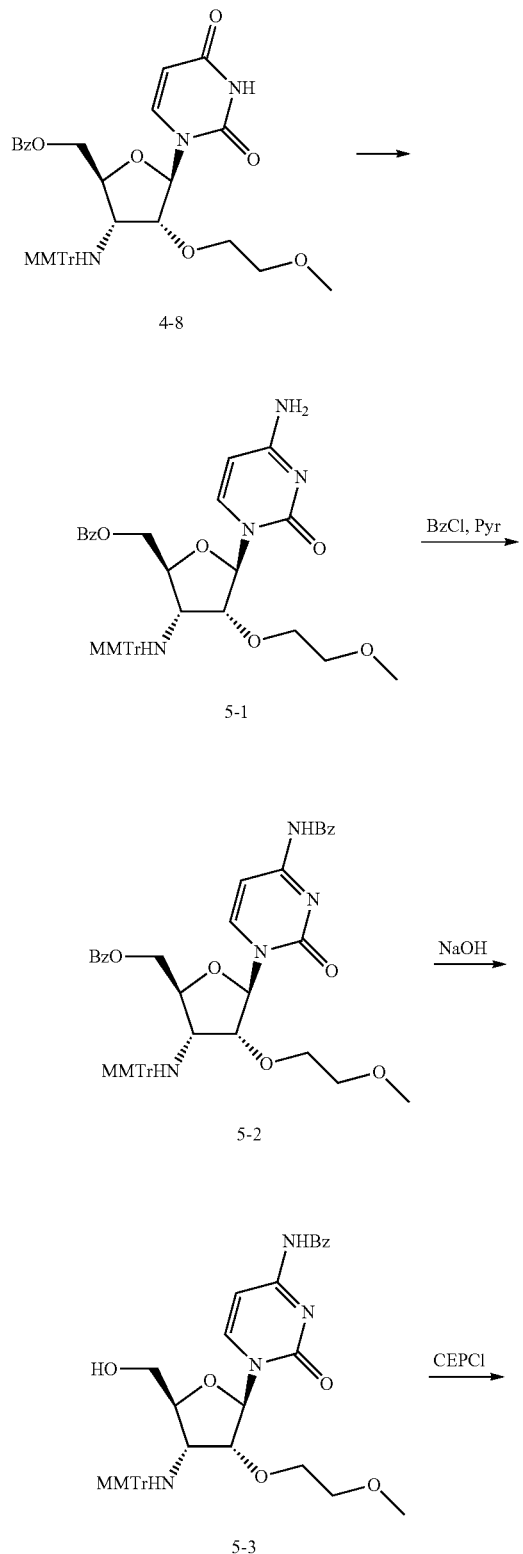

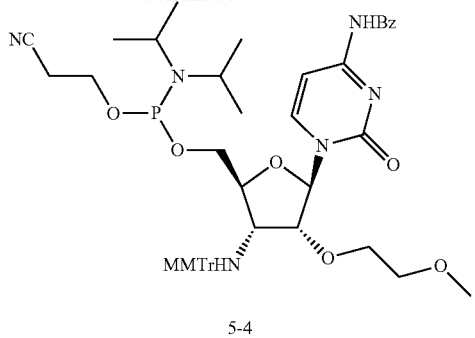

Preparation of (5-1): To a solution of 4-8 (18.50 g, 27.30 mmol) in acetonitrile (250.00 mL) was added TPSCl (16.49 g, 54.60 mmol) and DMAP (6.67 g, 54.60 mmol), then TEA (5.52 g, 54.60 mmol, 7.56 mL) was added to the solution. The reaction mixture was stirred at r.t. for 5 h under N2. $NH_4OH$ (50.00 mL) was added to the reaction mixture. The mixture was stirred at r.t. for 12 h. The solution was concentrated and extracted with EA. The organic layer was washed by brine and dried over $Na_2SO_4$. The organic layer was concentrated and purified by silica gel column to give 5-1 (16.00 g, 23.64 mmol) as a yellow solid.

Preparation of (5-2): To a solution of 5-1 (16.00 g, 23.64 mmol) in Pyridine (100.00 mL) was added BzCl (4.96 g, 35.46 mmol) at 0° C. The mixture was stirred at r.t. for 1 h. The solution was concentrated and purified by silica gel column to give 5-2 (17.40 g, 22.28 mmol) as a white solid.

Preparation of (5-3): Compound 5-2 (17.40 g, 22.28 mmol) was added to 180 mL of 1 N NaOH solution in Pyridine/MeOH/$H_2O$ (65/30/5) at 0° C. The suspension was stirred at 0° C. for 15 min. The reaction mixture was quenched by addition of sat. $NH_4Cl$ solution. The solution was extracted with EA and the combined organic layers were washed with sat. $NaHCO_3$ solution, brine, dried over $Na_2SO_4$, filtered, and concentrated. The residue was purified by column to give 5-3 (12.50 g, 18.47 mmol) as white solid. 1H-NMR (DMSO-$d_6$, 400 MHz): δ ppm 12.25 (s, 1H), 8.53 (d, J=7.6 Hz, 1H), 8.01 (d, J=5.2 Hz, 2H), 7.64-7.60 (m, 1H), 7.52-7.42 (m, 6H), 7.31 (d, J=8.8 Hz, 2H), 7.26-7.14 (m, 7H), 6.79 (d, J=8.8 Hz, 2H), 5.55 (s, 1H), 5.23 (t, J=3.6 Hz, 1H), 4.09-3.97 (m, 3H), 3.73 (s, 3H), 3.70-3.66 (m, 1H), 3.38-3.34 (m, 2H), 3.17 (s, 3H), 3.11-3.05 (m, 1H), 2.96-2.91 (m, 1H), 2.68 (d, J=10.8 Hz, 1H), 1.49 (d, J=4 Hz, 1H).

Preparation of (5-4): To a solution of 5-3 (12.50 g, 18.47 mmol) in DCM (100.00 mL) was added DMAP (451.30 mg, 3.69 mmol) and DIPEA (9.55 g, 73.88 mmol, 12.90 mL), then CEPCl (5.25 g, 22.16 mmol) was added. The mixture was stirred at r.t. for 30 min. The reaction was quenched with saturated $NaHCO_3$. The organic layer was washed with brine, dried over $Na_2SO_4$, concentrated to give the crude product. The crude was by Flash-Prep-HPLC. The product was dissolved in anhydrous toluene and concentrated for three times. Then the product was dissolved anhydrous acetonitrile and concentrated for three times. This resulted in 13 g to give 5-4 as a white solid. MS m/z [M-H]⁻ (ESI): 875.4. ¹H-NMR (400 MHz, $CDCl_3$): δ ppm 8.64-8.20 (m, 2H), 7.90-7.88 (m, 2H), 7.62-7.58 (m, 1H), 7.53-7.39 (m, 8H), 7.25-7.15 (m, 6H), 6.78-6.74 (m, 2H), 5.69 (d, J=1.72 Hz, 1H), 4.37-4.21 (m, 2H), 4.10-4.03 (m, 1H), 3.90-3.79 (m, 2H), 3.75 (d, J=1.64 Hz, 3H), 3.68-3.52 (m, 3H), 3.46-3.42 (m, 2H), 3.26 (d, J=1.2 Hz, 3H), 3.17-2.97 (m, 2H), 2.94-2.87 (m, 1H), 2.67-2.48 (m, 2H), 1.79-1.51 (m, 1H), 1.26-1.18 (m, 12H). $^{31}$PNMR (162 MHz, CDCl$_3$): 148.93, 148.03

Example 6

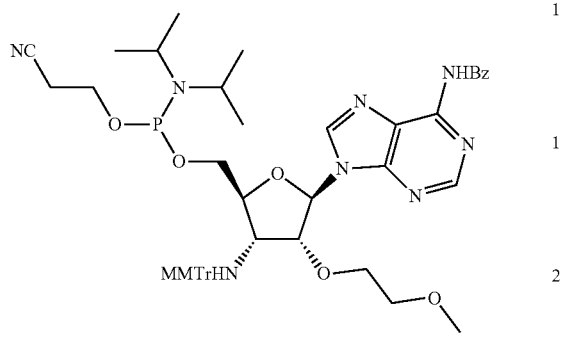

6-10

The synthesis of the 2'-O-methoxyethyl adenosine analogue 6-10 was achieved as shown below in scheme 6. The intermediate 6-2 under basic condition (NH$_3$/MeOH) resulted in diol 6-3, which then upon protection of 5'-hydroxy group using TBDPSCl to give 6-4 Intermediate 6-4. Then, 2'-O alkylation of 6-4 using 2-bromoethyl methyl ether/NaH/DMF to give 2'-O-methoxyethyl derivative 6-5 without the protection of C-6-exocyclic amine of 6-4. In an inventive way selective alkylation of 2'-OH group of intermediate 6-4 was achieved.

Scheme 4

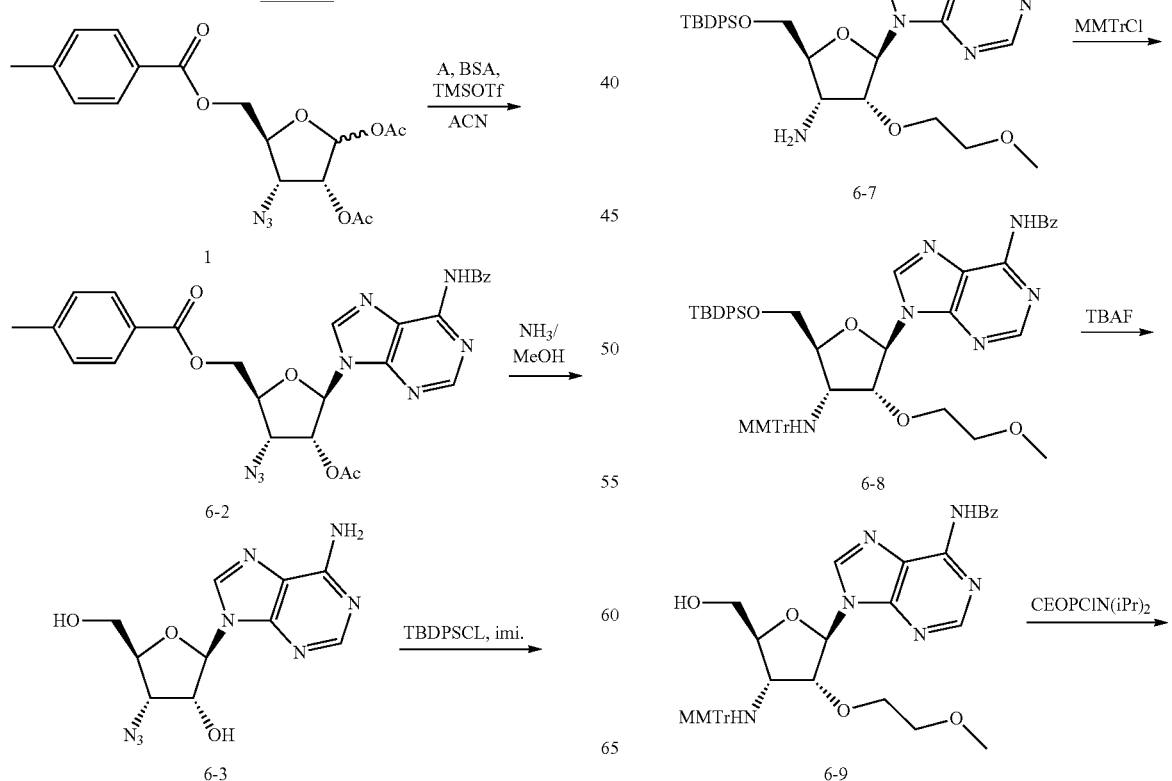

-continued

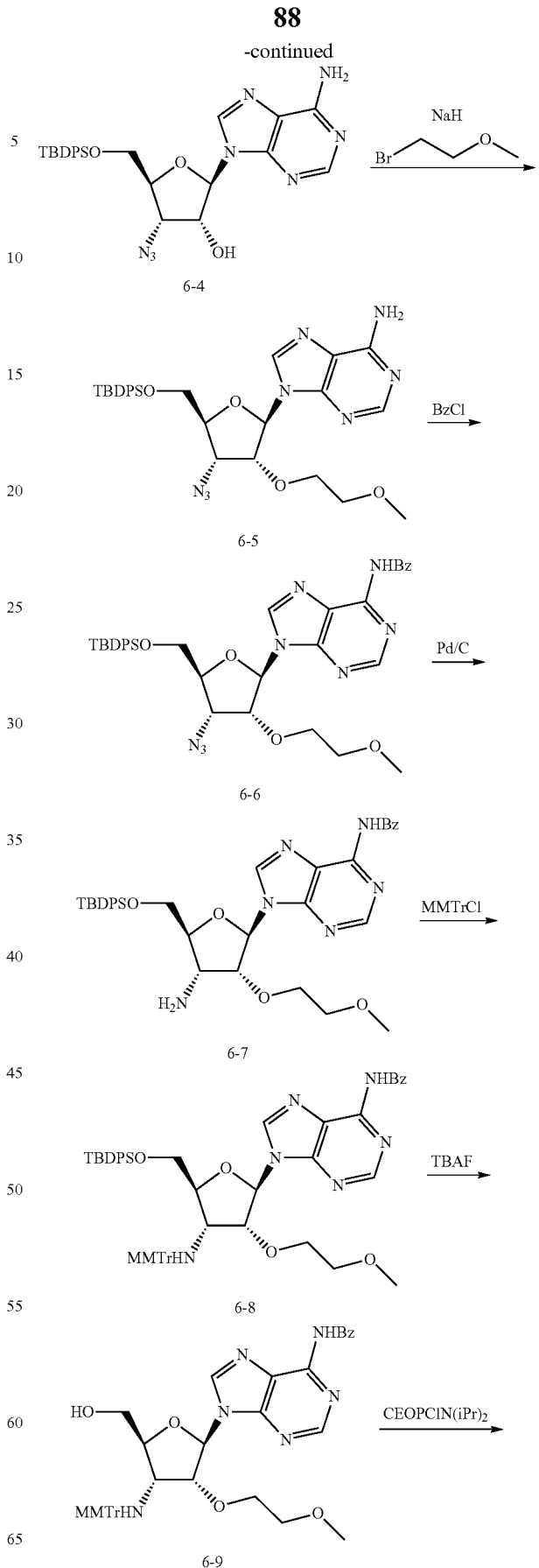

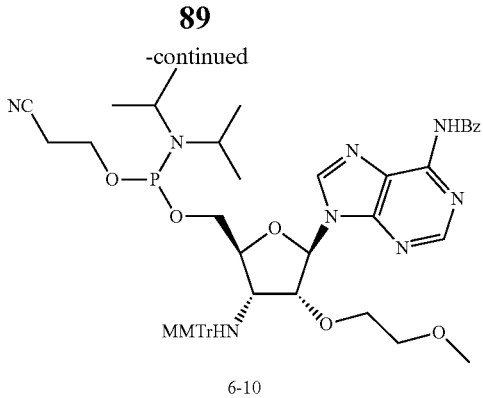

6-10

3'-Azido group of intermediate 6-5 was reduced to the amine 6-7, which was then immediately protected, such as reaction with 4-monomethoxytritylchloride, to give the precursor 6-8 after de-protection of 5'-OTBDPS group using TBAF/THF. The phosphitylation of 6-9 using known protocols is performed to give the desired 2'-O-methoxyethoxy adenine-NH-benzoyl phosphoramidite monomer 6-10.

Preparation of (6-2): To a solution of compound 1 (79.50 g, 210.68 mmol) in dry ACN (1.20 L) was added N-(5H-Purin-6-yl)benzamide (100.80 g, 421.36 mmol) and BSA (180.07 g, 884.86 mmol). The resulting suspension was stirred at 50° C. until clear. Then the mixture was cooled at −20° C. and TMSOTf (93.54 g, 421.36 mmol) was added by syringe. Then the mixture was stirred at 70° C. for 72 h under $N_2$ and quenched with sat $NaHCO_3$ and extracted with DCM. The organic layer was dried over $Na_2SO_4$, then solvent was evaporated, and the residue was purified on silica gel to afford compound 6-2 (107.50 g, 192.26 mmol, 91.26% yield) as a yellow solid. $^1$H-NMR (400 MHz, DMSO): δ=11.28 (s, 1H), 8.64 (d, J=6.4 Hz, 2H), 8.05 (d, J 8.0 Hz, 2H), 7.84 (d, J 8.0 Hz, 2H), 7.66 (t, J 7.6 Hz, 1H), 7.56 (t, J 8.0 Hz, 2H), 7.33 (d, J 8.0 Hz, 2H), 6.37 (d, J 3.6 Hz, 1H), 6.17 (dd, J 6.0 Hz, 1H), 5.09 (t, J 6.8 Hz, 1H), 4.69-4.56 (m, 2H), 4.40-4.38 (m, 1H), 2.39 (s, 3H), 2.17 (s, 3H). ESI-LCMS: m/z 557.2 [M+H]$^+$.

Preparation of (6-3): To a solution of compound 6-2 (107.50 g, 192.26 mmol) dissolved in 33 wt. % methylamine in ethanol (600.00 mL), then the mixture were stirred at 20° C. for 16 h, then solvent was evaporated, washed with 50% EtOAc in petroleum ether (1.5 L), filtered to afford compound 6-3 (52.50 g, 179.64 mmol, 93.44% yield) as a slightly yellow solid. ESI-LCMS: m/z 293.1 [M+H]$^+$.

Preparation of (6-4): A solution of compound 6-3 (52.50 g, 179.64 mmol), imidazole (18.32 g, 269.46 mmol) and TBDPS-Cl (54.34 g, 197.60 mmol) in pyridine (500.00 mL) was stirred at 20° C. for 2 h, LC-MS showed 6-3 was consumed. Then quenched with MeOH (30 mL), concentrated to give the crude product which was purified on silica gel with to afford compound 6-4 (72.60 g, 136.81 mmol, 76.16% yield) as a white solid. $^1$H-NMR (400 MHz, DMSO): δ=8.29 (s, 1H), 8.10 (s, 1H), 7.63-7.59 (m, 4H), 7.48-7.33 (m, 8H), 6.36 (d, J 5.6 Hz, 1H), 5.97 (d, J 4.4 Hz, 1H), 5.10-5.06 (m, 1H), 4.47 (t, J 5.6 Hz, 1H), 4.14-4.11 (m, 1H), 3.94 (dd, J 11.2 Hz, 1H), 3.83 (dd, J 11.6 Hz, 1H), 0.99 (s, 9H). ESI-LCMS: m/z 531.3 [M+H]$^+$.

Preparation of (6-5): A solution of 6-4 (35.00 g, 65.96 mmol) and 1-Bromo-2-methoxyethane (18.33 g, 131.91 mmol) in dry DMF (400.00 mL), was added NaI (19.77 g, 131.91 mmol) and $Ag_2O$ (15.29 g, 65.96 mmol), the mixture was stirred at room temperature for 5 h. Then the reaction was poured into ice water, extracted with EA, washed with brine and dried over anhydrous $Na_2SO_4$. The solvent was evaporated, and the residue was purified on silica gel to give 6-5 (23.70 g, 40.26 mmol, 61.04% yield) as a white solid and by-product of TBDPS lost 5.20 g, 9.81 mmol, 14.87% yield) as a white solid. $^1$H-NMR (400 MHz, DMSO): δ=8.31 (s, 1H), 8.11 (s, 1H), 7.63-7.60 (m, 4H), 7.47-7.44 (m, 2H), 7.40-7.36 (m, 6H), 6.10 (d, J 4.4 Hz, 1H), 5.02 (t, J 4.8 Hz, 1H), 4.69 (t, J 5.6 Hz, 1H), 4.18-4.14 (m, 1H), 3.95 (dd, J 11.6 Hz, 1H), 3.84 (dd, J 11.6 Hz, 1H), 3.78-3.75 (m, 2H), 3.45 (t, J 4.8 Hz, 1H), 3.16 (s, 3H), 0.99 (s, 9H). ESI-LCMS: m/z 589.5 [M+H]$^+$.

Preparation of (6-6): To a solution of 6-5 (31.23 g, 53.04 mmol) in pyridine (300.00 mL) at 0° C., was added BzCl (11.22 g, 79.56 mmol) dropwise. The mixture was stirred at r.t. for 2 h. Then the solution was cooled to 0° C., and ammonium hydroxide (20 mL, 30%) was added and the mixture was allowed to warm to r.t., then the solvent was evaporated, 300 mL $H_2O$ and 600 mL EA were added into separate the solution, the aqueous was extracted by EA, combined the organic and washed with brine, dried over anhydrous $Na_2SO_4$, the solvent was removed and the residue was purified on silica gel to give 6-6 (28.70 g, 41.42 mmol, 78.09% yield) as a white solid. ESI-LCMS: m/z 693.4 [M+H]$^+$.

Preparation of (6-7): A solution of 6-6 (28.70 g, 41.42 mmol) in EA (150.00 mL) was added Pd/C (3.00 g) and MeOH (150.00 mL) under $H_2$. The mixture was stirred at r.t. for 5 h. Then the reaction was filtered and the filtrate concentrated to give 6-7 (25.49 g, 38.22 mmol, 92.27% yield) as a gray solid. ESI-LCMS: m/z 667.3 [M+H]$^+$.

Preparation of (6-8): To a solution of 6-7 (25.49 g, 38.22 mmol) and $AgNO_3$ (12.98 g, 76.44 mmol) in DCM (300.00 mL) was added collidine (13.89 g, 114.66 mmol) and MMTrCl (19.43 g, 57.33 mmol), the mixture was stirred at r.t. for 2 h. Then the reaction was poured into ice water, the organic layer extracted with DCM, washed with brine and dried over anhydrous $Na_2SO_4$, the solvent was removed and the residue was purified on silica gel to give 6-8 (32.79 g, 34.92 mmol, 91.36% yield) as a gray solid.

Preparation of (6-9): A solution of 6-8 (32.79 g, 34.92 mmol) in THF (300.00 mL) was added TBAF (1M, 35.00 mL), the mixture was stirred at room temperature for 15 h. Then the solvent was removed and the residue was purified on silica gel with EA to give 6-9 (22.22 g, 31.71 mmol, 90.82% yield) as a white solid. $^1$H-NMR (400 MHz, $CDCl_3$): δ=8.68 (s, 1H), 8.32 (s, 1H), 8.04 (d, J=7.2 Hz, 2H), 7.61-7.57 (m, 1H), 7.53-7.48 (m, 6H), 7.40 (d, J=8.8 Hz, 2H), 7.21-7.12 (m, 6H), 6.73 (d, J=8.8 Hz, 2H), 6.09 (d, J=2.4 Hz, 2H), 4.08-4.02 (m, 2H), 3.93-3.87 (m, 1H), 3.72 (s, 3H), 3.58-3.53 (m, 1H), 3.43-3.39 (m, 3H), 3.24-3.19 (m, 4H), 2.19 (br, 1H).

Preparation of (6-10): To a solution of 6-9 (14.00 g, 19.98 mmol), DMAP (488.19 mg, 4.00 mmol) and DIPEA (6.46 g, 49.95 mmol, 8.73 mL) in dry DCM (100.00 mL) was added CEPCl (5.68 g, 23.98 mmol) dropwise under Ar. The mixture was stirred at room temperature for 1 h. Then the reaction was wished with 10% $NaHCO_3$ (aq) and brine, dried over $Na_2SO_4$, the solvent was removed and the residue was purified by c.c. with the PE/EA mixture, then concentrated to give the crude product. The crude product (10 g, dissolved in 10 mL of ACN) was purified by Flash-Prep-HPLC to obtain 6-10 (12.60 g, 13.98 mmol, 69.99% yield) as a white solid. Then the product was dissolved in dry toluene (15 mL) and concentrated three times, and with dry ACN three times. $^1$H-NMR (400 MHz, $CDCl_3$): δ=9.12 (d, J=46.8 Hz, 1H), 6=8.71 (d, J=11.6 Hz, 1H), 8.50 (s, 0.6H), 8.22 (s, 0.4H), 8.04 (t, J=7.2 Hz, 2H), 7.63-7.59 (m, 1H), 7.55-7.46 (m, 6H), 7.40-7.37 (m, 2H), 7.19-7.06 (m, 6H), 6.69 (dd, J=8.8 Hz, 2H), 6.03 (d, J=3.2 Hz, 1H), 4.36-4.24 (m, 2H), 3.92-3.78 (m, 2H), 3.71 (d, J=11.6 Hz, 3H), 3.67-3.33 (m, 7H), 3.29 (d, J=11.2 Hz, 3H), 3.17-3.10 (m, 1H), 2.88 (dd, J=27.2 Hz, 1H), 2.65-2.50 (m, 2H), 2.38 (d, J=4.4 Hz, 0.4H), 1.80 (d, J=4.0 Hz, 0.6H), 1.23-1.15 (m, 12H). $^{31}$PNMR (400 MHz, CDCl$_3$): 148.86, 148.22. ESI-LCMS: m/z 901.3 [M+H]$^+$.

Example 7

The appropriately protected 2'-O-ethyl-3'-amino-5'-phosphoramidite (example 9, 10, 11, 12), were prepared after chemical transformations shown in Scheme 5.

First for the synthesis of thymine based 3'-NH-MMtr-2'-O-ethyl phosphoramidites example 9, intermediate 2 was protected such as ethyl propynoate in the presence of dimethylaminopyridine (Scheme 8) to give base N-3 protected intermediate 8-4 to facilitate the 2'-O-alkylation in higher yield. Further deacetylation of 8-4 to give C-2'-hydroxy intermediate 8-5.

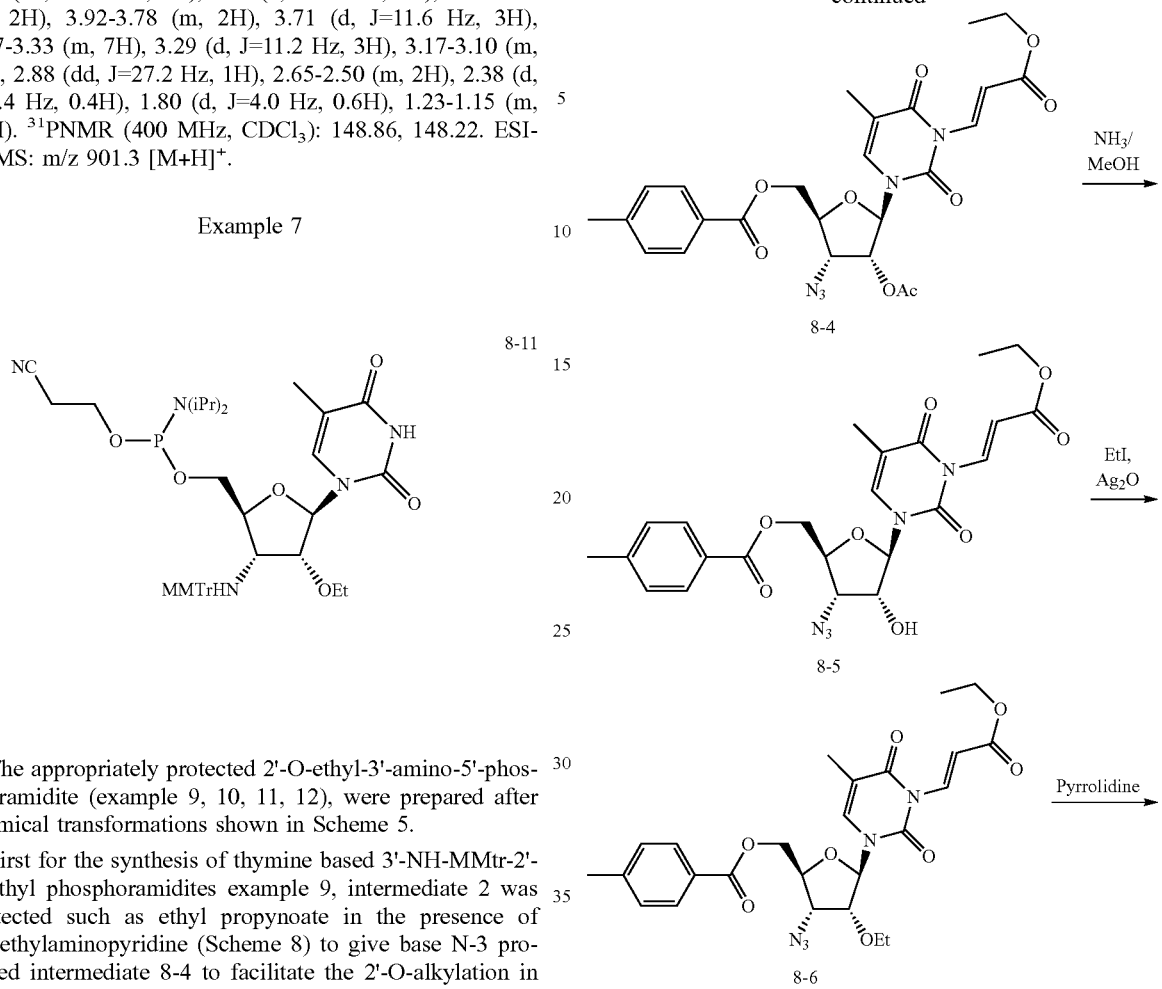

Scheme 5

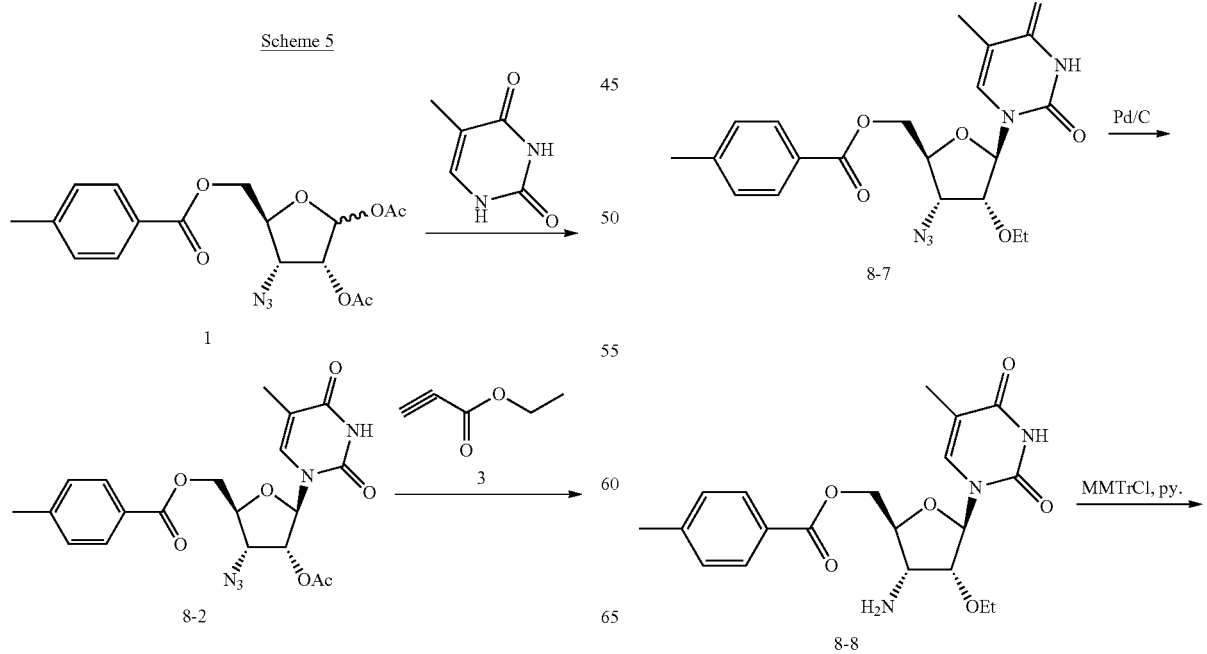

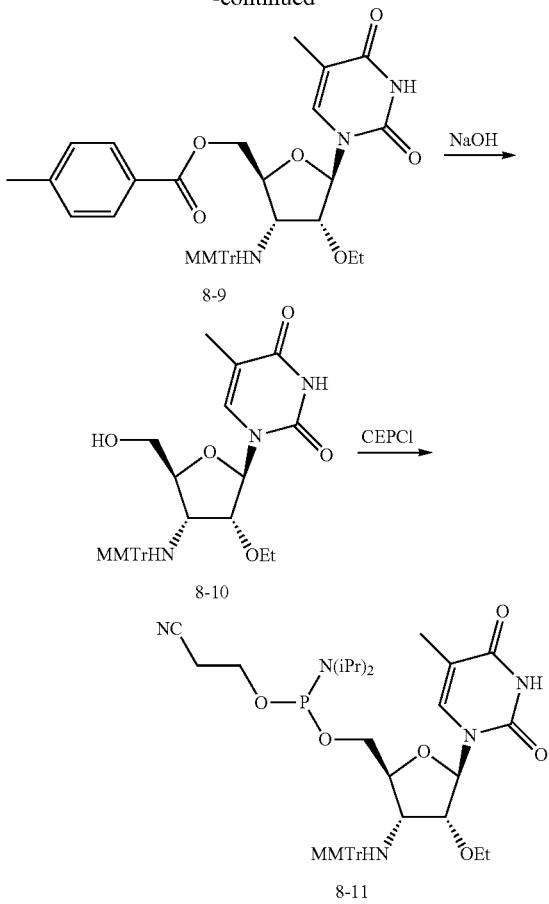

Further alkylation using iodoethane afforded 2'O-ethyl nucleoside 8-6. Intermediate 8-6 was converted to thymine base 2'-O-ethyl-3'-amino-5'-phosphoramidite 8-11 by following the similar chemistry for compound 4-10 shown in previous Scheme 4.

Preparation of (8-4): To a solution of 8-2 (22.0 g, 49.62 mmol) in MeCN (400 mL) was added DMAP (1.2 g, 9.92 mmol). Then 3 (5.8 g, 419.5 mmol) was added, the mixture was stirred at r.t. for 2 h under N2, TLC showed 8-2 was consumed. Concentrated and purified by a silica gel column by (PE:EA=6:1) to afford 8-4 (22.0 g, 40.63 mmol, 81.9% yield) as a yellow oil. ESI-LCMS: m/z 564 [M+Na]$^+$.

Preparation of (8-5): To a solution of 8-4 (28.0 g, 51.71 mmol) in MeOH (400 mL) was added con. NH$_4$OH aqueous solution (28 mL) at 0° C. The reaction mixture was stirred at 0° C. for 1.5 h, TLC showed 8-4 was consumed. Concentrated and purified by a silica gel column by (PE:EA=10:1-2:1) to afford 8-5 (21.0 g, 42.04 mmol, 81.3% yield) as a yellow oil. ESI-LCMS: m/z 522 [M+Na]$^+$.

Preparation of (8-6): To a solution of 8-5 (20.0 g, 40.04 mmol) in iodoethane (100 mL) was added Ag$_2$O (18.6 g, 80.08 mmol). The reaction mixture was stirred at 50° C. for 5 h, after LC-MS show totally consumed of 8-5 filtered with diatomite and concentrated to afford 8-6 (16.0, 30.33 mmol, 75.7% yield) as a yellow oil which was used directly in next step. ESI-LCMS: m/z 528 [M+H]$^+$.

Preparation of (8-7): To a solution of 8-6 (16.0 g, 30.33 mmol) in MeCN (400 mL) was added pyrrolidine (8.63 g, 121.32 mol, 12 mL), the reaction mixture was stirred at r.t. overnight, TLC showed 8-6 was totally consumed. Concentrated and purified by a silica gel column by (DCM:MeOH=100:1~50:1) to afford 7 (12.0 g, 27.94 mmol, 92.1% yield) as a yellow oil. ESI-LCMS: m/z 430 [M+H]$^+$.

Preparation of (8-8): To a solution of 8-7 (12.0 g, 27.94 mmol) in THF (200 mL) was added Pd/C (1.2 g), the mixture was stirred at r.t. under H$_2$ overnight. LC-MS showed 7 was totally consumed. Filtered and washed with DCM (100 mL*3), then concentrated to afford 8-8 (11.0 g, 27.27 mmol, 97.6% yield) as a gray solid which was used directly in next step. ESI-LCMS: m/z 404 [M+H]$^+$.

Preparation of (8-9): To a solution of 8-8 (10.0 g, 24.79 mmol) in DCM (80 mL) was added MMTrCl (11.4 g, 37.18 mmol), 2,4,6-collidine (2.0 g, 16.61 mmol, 6.5 mL) and AgNO$_3$ (6.3 g, 37.18 mmol), the mixture was stirred at r.t. for 1.5 h. TLC showed 8-8 was totally consumed. Filtered and the organic layer was washed with water and dried over Na$_2$SO$_4$, then concentrated and purified by a silica gel column by (PE:EA=5:1-1:1) to afford 8-9 (16.0 g, 23.68 mmol, 95.5% yield) as a light-yellow solid.

Preparation of (8-10): 8-9 (4.0 g, 5.92 mmol) was added to the solution of 1.0 N NaOH solution (20 mL, MeOH/H$_2$O=9:1). The reaction mixture was stirred at 40° C. for 2 h, TLC showed 8-9 was consumed, concentrated and extracted with DCM (20 mL*2), the organic layer was dried over Na$_2$SO$_4$ and concentrated, the residue was purified by a silica gel column by (DCM:MeOH=200:1-50:1) to afford 8-10 (3.0 g, 53.8 mmol, 90.9 yield) as a white solid.

Preparation of (8-11): To a solution of 8-10 (2.36 g, 4.23 mmol) in DCM (2.0 mL) was added DMAP (103 mg, 0.8 mmol) and DIPEA (2.2 g, 16.92 mmol, 2.96 mL). Then CEPCl (1.0 g, 4.23 mmol) was added. The reaction mixture was stirred at r.t. for 1 h. TLC showed 8-10 was consumed, washed with saturated NaHCO$_3$ (5 mL), separated the organic layer and washed the water layer with DCM (10 mL*2). The combined organic layer was washed with brine, dried over Na$_2$SO$_4$, concentrated, and purified by Flash-Prep-HPLC to afford 8-11 (2.45 g, 3.23 mmol, 76.36% yield) as a white solid. $^1$H NMR (400 MHz, CDCl$_3$) δ 8.62 (s, 1H), 7.74 (dd, J=1.4 Hz, 0.5H), 7.60-7.50 (m, 4H), 7.51-7.41 (m, 2H), 7.34-7.16 (m, 7H), 7.12 (d, J=1.4 Hz, 0.5H), 6.88-6.76 (m, 2H), 5.66 (s, 1H), 4.37-4.23 (m, 1H), 4.16-4.05 (m, 1H), 4.05-3.94 (m, 0.5H), 3.88-3.74 (m, 4.5H), 3.72-3.35 (m, 3H), 3.22 (td, J=10.3, 4.7 Hz, 0.5H), 3.03-2.89 (m, 1.5H), 2.80-2.69 (m, 1H), 2.61 (t, J=6.5 Hz, 1H), 2.37 (td, J=6.6, 1.3 Hz, 1H), 1.97 (d, J=3.5 Hz, 0.5H), 1.91 (dd, J=11.4, 1.2 Hz, 3H), 1.52 (d, J=4.7 Hz, 0.5H), 1.29-1.17 (m, 12H), 1.08 (td, J=7.0, 4.9 Hz, 3H). $^{31}$P NMR (162 MHz, CDCl$_3$) δ 149.31, 147.14. ESI-LCMS: m/z 576 [M+H]$^+$.

Quantitation of Crude Oligomer or Raw Analysis

Samples were dissolved in deionized water (1.0 mL) and quantitated as follows: Blanking was first performed with water alone (1.0 mL)$_{20}$ul of sample and 980 µL of water were mixed well in a microfuge tube, transferred to cuvette and absorbance reading obtained at 260 nm. The crude material is dried down and stored at –20° C.

Crude HPLC/LC-MS Analysis

The 0.1 OD of the crude samples were submitted for crude MS analysis. After Confirming the crude LC-MS data then purification step was performed.

HPLC Purification

The Phosphoramidate (NP) and Thiophosphoramidate (NPS) modified oligonucleotides with and without conjugates were purified by anion-exchange HPLC. The buffers were 20 mM sodium phosphate in 10% CH$_3$CN, pH 8.5

(buffer A) and 20 mM sodium phosphate in 10% $CH_3CN$, 1.8 M NaBr, pH 8.5 (buffer B). Fractions containing full-length oligonucleotides were pooled, desalted, and lyophilized.

Desalting of Purified Oligomer

The purified dry oligomer was then desalted using Sephadex G-25 M (Amersham Biosciences). The cartridge was conditioned with 10 mL of deionized water thrice. The purified oligomer dissolved thoroughly in 2.5 mL RNAse free water was then applied to the cartridge with very slow drop-wise elution. The salt free oligomer was eluted with 3.5 ml deionized water directly into a screw cap vial.

In Vitro Assay

Antisense oligonucleotides (ASOs) targeting exon 5 of human MAPT were synthesized. An ASO with phosphorothioate linkage chemistry and 2'-methoxyethyl (2'MOE) protecting groups in 5 nucleotide-long wings on either end of the molecule was synthesized, and an ASO with the same sequence targeting exon 5 of MAPT using the P5'-N3' phosphoramidate linkage ASO chemistry (rather than the phosphorothioate chemistry) was also synthesized. MAPT mRNA levels were evaluated in human neurons differentiated from human induced pluripotent stem cells (iPSCs) following treatment with either the phosphorothioate (OPS) or the phosphoramidate (NPS) chemistry but with the same 2'MOE protecting groups in the wings to determine if and to what extent these ASOs effectively reduced tau mRNA and protein levels, as well their effect on tau pathology in a transgenic mouse model of AD (DeVos et al., Sci Transl Med, 2017).

iPSC Generation and Differentiation into Cortical Neurons.

The parental iPSC line (Sigma catalog #iPSC0028) was generated by reprogramming epithelial cells from a 24-years old female donor with the four Yamanaka factors (Oct3/4, Sox2, Klf4 and c-Myc) using retroviral vectors. Human iPSCs were cultured feeder-free and fed daily with fresh mTeSR medium (Stem Cell Technologies). Cells were passaged with EDTA (Gibco) at confluency, and differentiation into neural progenitor cells (NPCs) and cortical neurons was performed using classic dual SMAD inhibition protocol. This protocol mostly generates glutamatergic layer V cortical neurons expressing TBR1 (approx. 20%) and CTIP2 (approx. 80%). Briefly, iPSCs were dissociated into single cell suspension and neuronal induction was triggered by following treatment with SB431542 and Dorsomorphin (neural induction media, see Table 1) for a period of 12 days.

TABLE 1

N2B27 media (composition)

| Component (final concentration) | Vendor | Cat No |
|---|---|---|
| Neurobasal ® Medium | Gibco | 21103-049 |
| DMEM/F-12, GlutaMAX supplement | Gibco | 31331-028 |
| B-27 Supplement, serum free (1%) | Gibco | 17504-044 |
| N-2 (0.5%) | Gibco | 17502-048 |
| MEM Non-Essential Amino Acids Solution (0.5%) | Gibco | 11140-035 |
| Sodium Pyruvate (0.5 mM) | Gibco | 11360-070 |
| GlutaMAX ™ Supplement (0.5%) | Gibco | 35050-038 |
| Penicillin-Streptomycin (10 U/mL) | Gibco | 15140-122 |
| 2-Mercaptoethanol (25 µM) | Gibco | 31350-010 |
| Insulin solution human (2.4 ug/mL) | Sigma | 19278 |

After induction, neuronal progenitor cells (NPCs) were treated with dispase and subplated for amplification three more times (at days 17, 20 and 25 approximately). Between day 25 and 30, NPC frozen stocks were prepared in neuronal progenitor freezing media (see Table 2) and kept in liquid nitrogen for subsequent experiments. NPCs were thawed in NPC reconstitution media (see Table 3) and kept during three days in culture before final subplating for ASO treatment.

TABLE 2

Neural induction media (composition)

| Component (final concentration) | Vendor | Cat No |
|---|---|---|
| N2B27 media | | |
| Dorsomorphin (1 µM) | Tocris | 3093 |
| SB431542 (10 µM) | Sigma | S4317 |

TABLE 3

Neuronal reconstitution media (composition)

| Component (final concentration) | Vendor | Cat No |
|---|---|---|
| N2B27 media | | |
| Rock inhibitor Y-27632 (10 µM) | Sigma | Y0503 |
| FGF-Basic (AA 10-155) Recombinant Human Protein (20 ng/mL) | Gibco | PHG0024 |

NPCs were plated on N2B27 media (see table 3) at a density of 15,000 cells per well in poly-ormithine/laminin (Sigma) coated 96-well plates.

To block cell proliferation cells received two treatments with 10 µM N—[N-(3,5-difluorophenacetyl)-L-alanyl]-S-phenylglycine t-butyl ester (DAPT, Sigma) on days 7 and 11 post-subplating. 14 days post thawing, N2B27 the media was replaced by final differentiation media (see table 4) that was changed 2-3 times per week (50%) until day 15 or 25, when ASO treatments were performed.

TABLE 4

Final neuronal differentiation media (composition)

| Component (final concentration) | Vendor | Cat No |
|---|---|---|
| N2B27 media | | |
| Recombinant Hu/Mo/Rat/Can/Equi BDNF Protein (20 ng/mL) | R & D Systems | 248-BD |
| Recombinant Human GDNF Protein (10 ng/mL) | R & D Systems | 212-GD |
| N6,2'-O-Dibutyryladenosine 3',5'-cyclic monophosphate sodium salt (500 µM) | Sigma | D0627 |
| L-Ascorbic acid (200 µM) | Sigma | A5960 |
| DAPT (10 µM) | Sigma | D5942 |

Antisense Oligonucleotide (ASO) Treatment to Target MAPT mRNA.

ASOs were synthesized as full phosphorothioate (OPS) as known in the art. The synthesis of thiophosphoramidate (NPS) ASOs were made according to the present disclosure. NPS ASOs contained nucleosides linked by NPS in the 5 nucleotides on either end of the ASO and a central 10 nucleotides-long gap with OPS-linked nucleotides. For both OPS and NPS ASOs, the 5 nucleotides-long wings on either side of the ASO contained 2' methoxyethyl (MOE) protecting groups. ASOs were reconstituted in phosphate-buffered saline (PBS) (Sigma) and their final concentrations were determined by the Beer-Lambert law by measuring their absorbance at 260 nm. A 20 nucleotide-long MAPT ASO with the following sequence: GCTTTTACTGAC-CATGCGAG (SEQ ID NO: 1) was modified having 2' MOE substitutions and phosphorothioate (OPS) linkages (OPS Modified Control SEQ ID NO: 1) and was modified having 2' MOE substitutions and thiophosphoramidate (NPS) linkages (NPS Modified SEQ ID NO: 1). A non-targeting scrambled ASO with the following sequence was used as negative control: CCTTCCCTGAAGGTTCCTCC (Non-MAPT Control; SEQ ID NO: 49). Human iPSC-derived cortical neurons were treated by free delivery of the ASOs at the indicated doses and for the indicated time periods.

TABLE 5

| Sequence | Sequences |
| --- | --- |
| OPS Modified Control SEQ ID NO: 1 | 5'-moeGps(5m)moeCps(5m)moeUps(5m)moe Ups(5m)moeUpsTpsAps(5m)CpsTpsGpsAps (5m)Cps(5m)CpsApsTpsmoeGps(5m)moeCps moeGpsmoeApsmoeG-3' |
| NPS Modified SEQ ID NO: 1 | 5'-moeGnpsmoeCnpsmoeUnpsmoeUnpsmoe UnpsTpsAps(5m)CpsTpsGpsAps(5m)Cps (5m)CpsApsTpsmoeGnpsmoeCnpsmoeGnps moeAnpsmoeGn-3' |

RNA Isolation and Real-Time Quantitative PCR.

RNA was isolated using the RNeasy96® kit (Qiagen) according to manufacturer's instructions. Briefly, we lysed cells by adding 150 µL RLT buffer and shaking on an orbital shaker for 30 min followed by the addition of an equal volume of 70% (v/v) ethanol. The mixture was subsequently transferred to columns and the RNA was bound to the filter by centrifugation at 5,600×g for 4 min at RT using a Sigma 4-18K centrifuge. Serial wash steps with RW1 buffer (700 µl, 4 min), RPE buffer (700 µl, 4 min) and a second RPE buffer step (700 µl, 10 min) were all done at 5,600×g at RT. The RNA was eluted using 60 µl nuclease-free water by centrifugation at 5,600×g at RT for 4 min. The RNA concentration was determined by spectroscopy using the Nanodrop® ND-8000 (ThermoFisher). Equal amounts of RNA were reverse transcribed using the high-capacity cDNA reverse transcription kit (ThermoFisher) in a 20 µl final reaction volume according to manufacturer's instructions. After a 10 min incubation at 25° C., reverse transcription occurred during 2 hours at 37° C., followed by enzyme inactivation at 85° C. for 5 min. To quantify total MAPT mRNA levels, cDNA was diluted 1:10, mixed with 2× Power SYBR™ Green Plus master mix (ThermoFisher) and DNA primers to a final reaction volume of 10 µl. The following primers were used to detect total MAPT mRNA at a final concentration of 500 nM (table 6).

TABLE 6

| Assay_id | forward | reverse |
| --- | --- | --- |
| MAPT_B01 | CCTCCAAGTGTGGCTCA TTA (SEQ ID NO: 50) | CAATCTTCGACTGGACTCTG (SEQ ID NO: 58) |
| MAPT_B02 | CAGTGGTCCGTACTCCA (SEQ ID NO: 51) | TGGACTTGACATTCTTCAGG (SEQ ID NO: 59) |
| MAPT_B04 | ATTGAAACCCACAAGCT GAC (SEQ ID NO: 52) | GAGGAGACATTGCTGAGATG (SEQ ID NO: 60) |
| MAPT_B06 | TCAGGTGAACTTTGAAC CAG (SEQ ID NO: 53) | CTTCCATCACTTCGAACTCC (SEQ ID NO: 61) |

TABLE 6-continued

| Assay_id | forward | reverse |
| --- | --- | --- |
| MAPT_JPNV-1 | CCAAGTGTGGCTCATTA GGCA (SEQ ID NO: 54) | CCAATCTTCGACTGGACTCT GT (SEQ ID NO: 62) |
| MAPT_JPNV-2 | GAGTCCAGTCGAAGATT GGGT (SEQ ID NO: 55) | GGCGAGTCTACCATGTCGAT G (SEQ ID NO: 63) |
| 3R MAPT | AGGCGGGAAGGTGCAAA TA (SEQ ID NO: 56) | GCCACCTCCTGGTTTATGAT G (SEQ ID NO: 64) |
| 4R MAPT | CGGGAAGGTGCAGATAA TTAA (SEQ ID NO: 57) | TATTTGCACACTGCCGCCT (SEQ ID NO: 65) |

Assays amplifying 8 different housekeeping genes using DNA primers (see Table 8) were also run. All the DNA primers were purchased from Integrated DNA Technologies. The RT-qPCR reactions were run on a HT7900 thermal cycler (Applied Biosystems) using standard cycling parameters. The specificity of the DNA primers was confirmed using a melting curve analysis. GeNorm analysis was used to determine the most stable housekeeping genes using qfBase+ (Biogazelle). All the data are normalized to the geometric mean of the most stable housekeeping genes and calibrated to a control condition.

AiphaLISA® Immunoassay.

Cells were lysed during 30-60 min in 96-well culture plates at room temperature (RT) in an orbital shaker using 40 µL per well of RIPA buffer (Sigma) containing phosphatase inhibitors (PhosSTOP™, Roche) and protease inhibitors (cOmplete™, Roche). The combination of HT7 (ThermoFisher) and hTAU10 antibodies (Janssen) was used for total tau quantification using AiphaLISA® technology (PerkinElmer). Measurements were performed in triplicates using 5 µl of 1:3 diluted lysate each time. Each sample was transferred to a 384-well assay plate for AlphaLISA® reaction in which 5 µl of cell extracts were incubated for 2 hours at RT with a mixture of biotinylated antibody and acceptor beads (see Table 7).

TABLE 7

Concentration of antibodies and beads used on AlphaLISA ® assay (final concentrations)

| Component | Final concentration |
| --- | --- |
| Biotinylated Ab (HT7) | 1.2 nM |
| Acceptor beads (hTAU10) | 10 µg/ml |
| Donor beads | 30 µg/ml |

Subsequently, donor beads were added to the wells and incubated at RT for 30 min before reading at 615 nm (upon illumination at 680 nm) on the EnVision plate reader (Perkin Elmer).

Total Protein Quantification.

Total protein quantification was performed using Bicinchoninic Acid Kit (Sigma). In order to evaluate the superiority of the NPS chemistry over the OPS chemistry, human iPSC-derived cortical neurons were treated with various concentrations of the MAPT ASOs. MAPT ASOs were added directly into the culture medium on day 25 after initiation of the differentiation process to final concentrations ranging from 1.25 µM to 10.0 µM. Equimolar concentrations of anon-targeting control ASO with the same chemistry was used as negative control. After 5 days, relative total MAPT mRNA levels was determined by RT-qPCR (Table 8).

TABLE 8

DNA primers for housekeeping genes

| Housekeeping gene name | Forward/ reverse primer | Primer sequence (5' to 3') |
|---|---|---|
| GAPDH | Forward | AAGGTGAAGGTCGGAGTCAAC (SEQ ID NO: 66) |
|  | Reverse | GGGGTCATTGATGGCAACAATA (SEQ ID NO: 67) |
| RNF20 | Forward | TTATCCCGGAAGCTAAACAGTGG (SEQ ID NO: 68) |
|  | Reverse | GTAGCCTCATATTCTCCTGTGC (SEQ ID NO: 69) |
| VIPAR | Forward | GGGAGACCCAAAGGGGAGTAT (SEQ ID NO: 70) |
|  | Reverse | GGAGCGGAATCTCTCTAGTGAG (SEQ ID NO: 71) |
| SCLY | Forward | ACTATAATGCAACGACTCCCCT (SEQ ID NO: 72) |
|  | Reverse | CTTCCTGCTGAATACGGGCTG (SEQ ID NO: 73) |
| PRDM4 | Forward | CACCTCCACAGTACATCCACC (SEQ ID NO: 74) |
|  | Reverse | TGATAGGGATCTAGTGCTGAAGG (SEQ ID NO: 75) |
| ENOX2 | Forward | TCATTGTGGAAGTTTTCGAGCA (SEQ ID NO: 76) |
|  | Reverse | TGCGGTAACCAGACAGATACA (SEQ ID NO: 77) |
| UBE4A | Forward | TAGCCGCTCATTCCGATCAC (SEQ ID NO: 78) |
|  | Reverse | GGGATGCCATTCCCGCTTT (SEQ ID NO: 79) |
| ERCC6 | Forward | TCACGTCATGTACGACATCCC (SEQ ID NO: 80) |
|  | Reverse | GTGGCAGCTTGAGGGCTAAG (SEQ ID NO: 81) |

Both negative control ASOs did not affect total MAPT mRNA levels (Table 9).

TABLE 9

Relative total MAPT mRNA levels following ASO treatment.

| SEQ ID NO: | ASO Modification | ASO concentration (µM) | Relative MAPT mRNA levels (mean ± SD) (% versus 0 µM) |
|---|---|---|---|
| OPS Modified Control SEQ ID NO: 1 | OPS 2'MOE MAPT | 0.00 | 124.0 ± 40.7 |
|  |  | 1.25 | 130.7 ± 21.4 |
|  |  | 2.5 | 131.0 ± 14.6 |
|  |  | 5.0 | 72.9 ± 8.0 |
|  |  | 10.0 | 42.3 ± 2.7 |

TABLE 9-continued

Relative total MAPT mRNA levels following ASO treatment.

| SEQ ID NO: | ASO Modification | ASO concentration (µM) | Relative MAPT mRNA levels (mean ± SD) (% versus 0 µM) |
|---|---|---|---|
| NPS Modified SEQ ID NO: 1 | NPS 2'MOE MAPT | 0.00 | 97.5 ± 7.2 |
|  |  | 1.25 | 55.0 ± 3.3 |
|  |  | 2.5 | 48.6 ± 7.0 |
|  |  | 5.0 | 40.5 ± 7.8 |
|  |  | 10.0 | 22.5 ± 2.5 |
| OPS Modified Non-MAPT Control | OPS 2'MOE non-MAPT control | 0.00 | 103.6 ± 14.2 |
|  |  | 1.25 | 94.2 ± 7.2 |
|  |  | 2.5 | 94.4 ± 9.2 |
|  |  | 5.0 | 93.5 ± 11.4 |
|  |  | 10.0 | 83.6 ± 11.0 |
| NPS Modified Non-MAPT Control | NPS 2'MOE non-MAPT control | 0.00 | 97.3 ± 4.0 |
|  |  | 1.25 | 82.4 ± 13.7 |
|  |  | 2.5 | 87.6 ± 18.9 |
|  |  | 5.0 | 105.6 ± 10.9 |
|  |  | 10.0 | 113.6 ± 13.2 |

NPS ASOs reduced total MAPT mRNA levels by 2× the amount of OPS ASOs as depicted in table 8.

In order to assess whether NPS MAPT ASOs was also more effective in reducing tau protein levels compared to OPS MAPT ASOs, human iPSC-derived cortical neurons were treated starting on day 15 after initiation of differentiation and ASOs were added every 5 days for a total period of 15 days. This treatment paradigm was necessary as the half-life of tau protein is thought to be very long given its function in stabilizing microtubules, particularly in neurons with their long axons. Following this prolonged ASO treatment period, the cells were lysed and tau protein levels were evaluated using bead-based immunoassays (Table 10).

TABLE 10

Relative total tau protein levels determined by AlphaLISA ® following ASO treatment.

| SEQ ID NO: | ASO Modification | ASO concentration (µM) | Relative Tau protein levels (mean ± SD) (% versus 0 µM) |
|---|---|---|---|
| OPS Modified Control SEQ ID NO: 1 | OPS 2'MOE MAPT | 0.00 | 100.0 ± 19.9 |
|  |  | 1.25 | 73.1 ± 16.6 |
|  |  | 2.5 | 77.9 ± 8.7 |
|  |  | 5.0 | 50.2 ± 10.1 |
|  |  | 10.0 | 39.9 ± 4.8 |
| NPS Modified SEQ ID NO: 1 | NPS 2'MOE MAPT | 0.00 | 100.0 ± 16.9 |
|  |  | 1.25 | 40.9 ± 12.7 |
|  |  | 2.5 | 31.7 ± 6.3 |
|  |  | 5.0 | 17.6 ± 3.2 |
|  |  | 10.0 | 19.6 ± 1.6 |
| OPS Modified Non-MAPT Control | OPS 2'MOE non-MAPT control | 0.00 | 100.0 ± 16.4 |
|  |  | 1.25 | 81.7 ± 13.4 |
|  |  | 2.5 | 94.9 ± 16.3 |
|  |  | 5.0 | 74.5 ± 8.5 |
|  |  | 10.0 | 90.4 ± 17.4 |
| NPS Modified Non-MAPT Control | NPS 2'MOE non-MAPT control | 0.00 | 100.0 ± 11.3 |
|  |  | 1.25 | 104.9 ± 40.9 |
|  |  | 2.5 | 86.3 ± 32.8 |
|  |  | 5.0 | 55.7 ± 28.5 |
|  |  | 10.0 | 106.2 ± 19.9 |

The negative control ASOs did not affect tau protein levels. However, MAPT NPS ASOs dose-dependently reduced tau protein levels 2× more than MAPT OPS ASOs as depicted in table 9.

From these examples, MAPT ASOs with NPS chemistry were determined to be surprisingly superior in reducing total MAPT mRNA and tau protein levels in human iPSC-derived neurons compared to an ASO with the same sequence but with OPS chemistry.

IEX HPLC and Electrospray LC/MS Analysis

Stability Testing of Complexed Oligonucleotides

Approximately 0.10 OD of oligomer is dissolved in water and then pipetted in special vials for IEX-HPLC and LC/MS analysis. Analytical HPLC and ES LC-MS established the integrity of the oligonucleotides.

In embodiments, the disclosed oligonucleotides display an increased affinity for a target nucleic acid sequence compared to an unmodified oligonucleotide of the same sequence. For example, in some sequences the disclosed oligonucleotides have a nucleobase sequence that is complementary and hybridizes to a target nucleic acid sequence at a higher affinity than an unmodified oligonucleotide of the same sequence. In embodiments, the disclosed oligonucleotide complexed/hybridized with a complementary target nucleic acid sequence has a melting temperature $T_m$ of >37° C. The duplex/complex may be formed under physiological conditions or nearly physiological conditions such as in phosphate-buffered saline (PBS). In embodiments, the $T_m$ of the duplex/complex is >50° C. In embodiments, the $T_m$ of the duplex/complex is 50-100° C. In embodiments, the $T_m$ of the disclosed oligonucleotide duplexed with a target nucleic acid sequence under physiological conditions or nearly physiological conditions is >50° C.

The duplex stability of disclosed oligonucleotides binding with target RNA sequence were evaluated using the thermal dissociation data of duplexes. The thermal dissociation studies were performed by measuring the temperature dependent UV absorbance at 260 nm of duplexes using Shimadzu UV2600 Spectrometer connected to a Shimadzu Temperature Controller and Julabo F12-ED constant temperature bath. The disclosed oligonucleotide and target nucleic acid sequence were mixed in an equimolar ratio to give a final duplex concentration of 2 μM. All samples were prepared in 1×PBS buffer condition (137 mM NaCl, 2.7 mM KCl, 10 mM $Na_2HPO_4$, 1.8 mM $KH_2PO_4$, pH 7.2). The UV-Vis absorbance at 260 nm was recorded and corrected using the absorbance at 380 nm (UV cell path length=1 cm). The data were recorded at a rate of 1° C./min, in 1° C. intervals, for both the heating (20-95° C.) and cooling (95-20° C.) runs. The $T_m$ values were determined by taking the first derivative of the heating sigmoidal profiles, using LabSolutions $T_m$ Analysis Software. Final $T_m$ is an average of three independent trials, and errors represent the standard deviation. As set forth in Table 11, NPS modified SEQ ID NO: 1 has a $T_m$ of ~+0.8° C. per 3'-NH.

TABLE 11

| SEQ ID NO: | ASO Modification | $T_m$ with RNA (° C) |
|---|---|---|
| OPS Modified Control SEQ ID NO: 1 | OPS 2'MOE MAPT | 62.4 (±0.6) |
| NPS Modified SEQ ID NO: 1 | NPS 2'MOE MAPT | 68.8 ((±0.5) |

Validation of TAU GAPmers

To evaluate the efficacy of the TAU GAPmers, a human neuronal cell line (KELLY cells) were treated with various concentrations ranging from 80 nM up to 20 μM. Two versions of the lead GAPmers: 2'-O-methyl (2'OMe) and 2'-O-methoxyethyl (2'MOE) were evaluated. These GAPmers are in a 5-10-5 form, meaning that the first and last 5 nucleotides include NPS and 2' chemistries, and the middle 10 nucleotides are the "gap" having OPS chemistry. Three days after treatment initiation, total RNA was collected and evaluated for total Tau mRNA levels by RT-qPCR using 6 different assays (see Table 6). The expression of 3R and 4R Tau mRNA was evaluated in the treated cells by RT-qPCR (see Table 6).

TABLE 12

| GAPmer | Bond chemistry 2'-O chemistry | ASO sequence | ASO target site |
|---|---|---|---|
| A | NPS-<u>OPS</u>-NPS 2'MOE | GCUUUTTTGTCATCGCUUCC (SEQ ID NO: 82) | Exon 5 |
| B | NPS-<u>OPS</u>-NPS 2'OMe | | |
| C | NPS-<u>OPS</u>-NPS 2'MOE | UUGAUAUUATCCTTTGAGCC (SEQ ID NO: 83) | Exon 10 |
| D | NPS-<u>OPS</u>-NPS 2'OMe | | |
| E | NPS-<u>OPS</u>-NPS 2'MOE | GGUGAUAUUGTCCAGGGACC (SEQ ID NO: 84) | Exon 12 |
| F | NPS-<u>OPS</u>-NPS 2'OMe | | |

All GAPmers showed a dose-dependent reduction of total 3R and 4R Tau mRNA in a dose-dependent manner. GAPmers C and D that target exon 10 of Tau mRNA were more effective in reducing 4R Tau mRNA levels compared to the other GAPmers.

To confirm that these GAPmers also reduce Tau mRNA levels in human neurons, the same experiment was performed in human iPSC-derived neurons and treated these cells for 72 hours with the same GAPmers. Very similar results were obtained for each of the GAPmers in iPSC-derived neurons compared to KELLY cell.

GAPmer Biodistribution

Additional ASO GAPmers were synthesized with unmodified chemistry as well as with the NPS chemistry. The IDs, chemistry, sequences and target site of these ASOs are listed in Table 13. These GAPmers are in a 5-10-5 form, meaning that the first and last 5 nucleotides include the indicated bond and 2' chemistries, and the middle 10 nucleotides are the "gap" having OPS chemistry. In order to evaluate if the NPS TAU GAPmer had a different/superior biodistribution profile, GAPmer E was radiolabeled it with Iodine-125. A similar approach was followed to radioactively label the GAPmer G with Iodine-125.

TABLE 13

| GAPmer | Bond chemistry 2'-O chemistry | ASO sequence | ASO target site |
|---|---|---|---|
| G | OPS/OPO-<u>OPS</u>-OPS/OPO 2'MOE | CCGTTTTCTTACCACCCT (SEQ ID NO: 85) | Intron 9 |
| H | NPS/NPO-<u>OPS</u>-NPS/NPO 2'MOE | CCGUUTTCTTACCACCCU (SEQ ID NO: 86) | |

TABLE 13-continued

| GAPmer | Bond chemistry 2'-O chemistry | ASO sequence | ASO target site |
|---|---|---|---|
| I | NPS-OPS-NPS 2'MOE | CCGUUTTCTTACCACCCU (SEQ ID NO: 87) | |

The radiolabeled compounds were into rats via an intrathecal bolus injection and imaged the animals in 4× during the first hour after the injection, followed by image acquisitions at 6 hours and 24 hours, as well as 7 days and 14 days post injection using single positron emission computed tomography (SPECT/CT). The results of this biodistribution study indicated that the comparative GAPmer G travels faster to the brain but quickly clears out of the brain to reach steady state levels by 6-24 hours post injection (Tables 14-15). GAPmer E appears to travel slower to the brain but reaches higher steady state levels in the brain compared to the comparative GAPmer G (Tables 14-15). In addition, GAPmer E appears to be retained for a longer period in different CNS regions (including deeper brain regions and the spinal cord) compared to the comparative GAPmer G (Tables 14-15). In conclusion, this study indicates that GAPmer E targeting TAU has longer retention times in the rodent CNS compared to the comparative GAPmer G.

TABLE 14

| Time (h) | | 0 | 0.25 | 0.5 | 0.75 | 6 | 24 | 168 | 336 |
|---|---|---|---|---|---|---|---|---|---|
| | | | | | GAPmer E | | | | |
| CSF Cervical Percent ID (% ID) | Mean | 10.8321 | 8.47327 | 7.19433 | 6.66709 | 1.25181 | 0.865811 | 0.537386 | 0.284057 |
| CSF Cervical Percent ID/g (% ID/g) | SEM Mean | 0.866516 76.27 | 0.97213 59.4654 | 1.1427 50.4656 | 1.15989 46.7394 | 0.181687 9.35959 | 0.200669 6.01616 | 0.260395 3.29889 | 0.193775 1.55895 |
| CSF Lumbar Percent ID (% ID) | SEM Mean | 5.46944 0.578109 | 5.69153 0.77805 | 7.4367 0.723477 | 7.62121 0.543578 | 1.20537 0.357861 | 1.20406 0.301755 | 1.55303 0.205616 | 1.02219 0.147592 |
| CSF Lumbar Percent ID/g (% ID/g) | SEM Mean | 0.083627 9.35819 | 0.162685 12.5983 | 0.065018 11.6298 | 0.099339 8.69566 | 0.089864 5.99358 | 0.085314 4.74398 | 0.072481 2.40874 | 0.066745 1.49488 |
| CSF Thoracic Percent ID (% ID) | SEM Mean | 1.63028 6.95045 | 2.93894 7.05609 | 1.32603 6.70884 | 1.6503 6.29832 | 1.66635 1.53496 | 1.3636 0.770341 | 1.00223 0.287605 | 0.783811 0.064824 |
| CSF Thoracic Percent ID/g (% ID/g) | SEM Mean | 0.882792 40.8075 | 0.607619 41.4428 | 0.426338 39.4093 | 0.308317 37.017 | 0.254473 9.19442 | 0.100461 4.52467 | 0.065515 1.48717 | 0.036388 0.316396 |
| Deep Cervical Lymph Nodes Percent ID (% ID) | SEM Mean | 4.87729 0.002162 | 3.1295 0.015821 | 1.91031 0.02634 | 1.46663 0.027323 | 1.68638 0.022633 | 0.519338 0.304756 | 0.352275 0.266843 | 0.18884 0.259165 |
| Deep Cervical Lymph Nodes Percent ID/g (% ID/g) | SEM Mean | 0.001526 0.078184 | 0.010442 0.572226 | 0.018233 0.952703 | 0.016429 0.988237 | 0.046625 9.07292 | 0.020172 11.0227 | 0.026647 9.65144 | 0.053091 9.37372 |
| Heart Percent ID (% ID) | SEM Mean | 0.055195 0 | 0.37767 0 | 0.659483 5.74E-05 | 0.594218 5.98E-06 | 1.68638 0.022633 | 0.729592 0.003495 | 0.963801 0.002469 | 1.92026 0 |
| Heart Percent ID/g (% ID/g) | SEM Mean | 0 0 | 0 0 | 5.74E-05 3.41E-05 | 3.85E-06 3.55E-06 | 0.018774 0.013466 | 0.001487 0.002102 | 0.00104 0.00132 | 0 0 |
| Left Kidney Percent ID (% ID) | SEM Mean | 0 0 | 0 0.2285 | 3.41E-05 1.48109 | 2.29E-06 3.79931 | 0.01117 13.2502 | 0.000884 14.9802 | 0.000537 14.8239 | 0 14.6498 |
| | SEM | 0 | 0.2285 | 0.836824 | 0.946707 | 0.551601 | 0.182297 | 0.319957 | 0.404948 |

TABLE 14-continued

| Time (h) | | 0 | 0.25 | 0.5 | 0.75 | 6 | 24 | 168 | 336 |
|---|---|---|---|---|---|---|---|---|---|
| Left Kidney Percent ID/g (% ID/g) | Mean | 0 | 0.120413 | 0.780397 | 2.00179 | 6.98143 | 7.89354 | 7.81194 | 7.71641 |
| Liver Percent ID (% ID) | SEM | 0 | 0.120413 | 0.440991 | 0.498757 | 0.29024 | 0.096685 | 0.171932 | 0.214333 |
| | Mean | 0 | 6.83E-06 | 0.034992 | 0.427209 | 2.2748 | 2.27037 | 1.5343 | 0.577397 |
| Liver Percent ID/g (% ID/g) | SEM | 0 | 6.83E-06 | 0.03359 | 0.225124 | 0.179946 | 0.130887 | 0.052462 | 0.214105 |
| | Mean | 0 | 6.62E-06 | 0.033893 | 0.413791 | 2.20335 | 2.19906 | 1.48612 | 0.559262 |
| Right Kidney Percent ID (% ID) | SEM | 0 | 6.62E-06 | 0.032535 | 0.218053 | 0.174294 | 0.126776 | 0.050804 | 0.207381 |
| | Mean | 0 | 0.534098 | 2.54753 | 4.46871 | 13.0671 | 15.5683 | 14.6128 | 14.4735 |
| Right Kidney Percent ID/g (% ID/g) | SEM | 0 | 0.534098 | 0.871366 | 0.684733 | 0.939278 | 0.407473 | 0.264569 | 0.543962 |
| | Mean | 0 | 0.278768 | 1.32942 | 2.33193 | 6.81815 | 8.12938 | 7.625 | 7.45214 |
| Superficial Cervical Lymph Nodes Percent ID (% ID) | SEM | 0 | 0.278768 | 0.454796 | 0.357303 | 0.490355 | 0.212582 | 0.136791 | 0.246694 |
| | Mean | 0 | 0.046892 | 0.076572 | 0.061611 | 0.145891 | 0.202045 | 0.1679 | 0.136729 |
| Superficial Cervical Lymph Nodes Percent ID/g (% ID/g) | SEM | 0 | 0.043098 | 0.061371 | 0.044305 | 0.030862 | 0.059684 | 0.02844 | 0.024512 |
| | Mean | 0 | 0.043098 | 5.5827 | 4.49193 | 10.6365 | 14.7306 | 12.2412 | 9.96856 |
| Whole Brain Percent ID (% ID) | SEM | 0 | 3.41878 | | | | | | |
| | Mean | 22.6306 | 3.14216 | 4.47443 | 3.23018 | 2.25008 | 4.35143 | 2.07352 | 1.78707 |
| Whole Brain Percent ID/g (% ID/g) | SEM | 1.68624 | 18.8312 | 16.329 | 14.815 | 8.66836 | 7.84457 | 6.01653 | 5.66245 |
| | Mean | 13.6667 | 1.35974 | 1.61868 | 1.73388 | 0.673152 | 0.358564 | 0.670171 | 0.594421 |
| CSF Cervical Percent ID (% ID) | SEM | 1.05573 | 11.3745 | 9.8642 | 8.95243 | 5.23969 | 4.71044 | 3.37774 | 2.9616 |
| | | | 0.870626 | 1.01123 | 1.08442 | 0.4077 | 0.215852 | 0.355915 | 0.271713 |

Comparative GAPmer G

| Time (h) | | 0 | 0.25 | 0.5 | 0.75 | 6 | 24 | 168 | 336 |
|---|---|---|---|---|---|---|---|---|---|
| CSF Cervical Percent ID (% ID) | Mean | 11.152 | 9.78028 | 9.14125 | 8.59638 | 1.9599 | 1.31077 | 1.2578 | 1.00442 |
| | SEM | 0.715641 | 0.795605 | 1.21719 | 1.38085 | 0.111631 | 0.099487 | 0.079583 | 0.056467 |
| | Mean | 69.7207 | 61.0495 | 57.0796 | 53.7526 | 13.4481 | 9.02884 | 7.68471 | 5.66153 |
| CSF Cervical Percent ID/g (% ID/g) | SEM | 5.26996 | 5.0583 | 7.88092 | 9.14163 | 1.06733 | 0.713906 | 0.479601 | 0.22366 |
| | | | | | | | | | 7 |

TABLE 14-continued

| Time (h) | | 0 | 0.25 | 0.5 | 0.75 | 6 | 24 | 168 | 336 |
|---|---|---|---|---|---|---|---|---|---|
| CSF Lumbar Percent ID (% ID) | Mean | 2.11315 | 2.30045 | 2.20845 | 2.08811 | 0.876204 | 0.635229 | 0.614291 | 0.545859 |
| CSF Lumbar Percent ID/g (% ID/g) | SEM | 0.618352 | 0.652777 | 1.03885 | 1.15341 | 0.412648 | 0.250849 | 0.32343 | 0.308902 |
| | Mean | 24.3213 | 26.6065 | 25.1407 | 23.8978 | 11.1123 | 8.07892 | 5.77421 | 3.99638 |
| CSF Thoracic Percent ID (% ID) | SEM | 3.8726 | 4.01662 | 8.94291 | 10.8027 | 4.14563 | 2.4462 | 2.66268 | 1.97635 |
| | Mean | 10.9876 | 11.8052 | 11.3563 | 10.3865 | 3.01616 | 1.81053 | 1.69423 | 1.29347 |
| CSF Thoracic Percent ID/g (% ID/g) | SEM | 1.59735 | 2.20522 | 2.52628 | 2.30952 | 0.802764 | 0.513927 | 0.637544 | 0.60702 |
| | Mean | 61.5725 | 66.1599 | 63.7407 | 58.4808 | 16.3486 | 9.67105 | 7.78233 | 5.39928 |
| Deep Cervical Lymph Nodes Percent ID (% ID) | SEM | 8.52219 | 12.087 | 14.1188 | 13.1369 | 4.11143 | 2.56419 | 2.70691 | 2.47457 |
| | Mean | 0.002608 | 0.003654 | 0.00735 | 0.01125 | 0.230341 | 0.309695 | 0.297415 | 0.277717 |
| Deep Cervical Lymph Nodes Percent ID/g (% ID/g) | SEM | 0.000961 | 0.002209 | 0.005015 | 0.004754 | 0.02465 | 0.015466 | 0.029098 | 0.032069 |
| | Mean | 0.09433 | 0.132166 | 0.265826 | 0.406905 | 8.33121 | 11.2014 | 10.7572 | 10.0447 |
| Heart Percent ID (% ID) | SEM | 0.034745 | 0.079915 | 0.18137 | 0.171952 | 0.891567 | 0.559385 | 1.05244 | 1.15989 |
| | Mean | 0 | 0 | 0 | 2.83E-07 | 0.000858 | 0.000364 | 1.19E-05 | 0 |
| Heart Percent ID/g (% ID/g) | SEM | 0 | 0 | 0 | 2.83E-07 | 0.000396 | 0.000262 | 5.77E-05 | 0 |
| | Mean | 0 | 0 | 0 | 1.73E-07 | 0.000514 | 0.000219 | 3.66E-05 | 0 |
| Left Kidney Percent ID (% ID) | SEM | 0 | 0 | 0 | 1.73E-07 | 0.000238 | 0.000159 | 8.74E-06 | 0 |
| | Mean | 0 | 0 | 0 | 1.98E-07 | 6.35087 | 9.57737 | 7.10E-06 | 7.18053 |
| Left Kidney Percent ID/g (% ID/g) | SEM | 0 | 0 | 0 | 1.98E-07 | 0.425138 | 0.291836 | 5.20E-06 | 0.192997 |
| | Mean | 0 | 0 | 0 | 1.04E-07 | 3.34559 | 5.04636 | 8.41903 | 3.78354 |
| Liver Percent ID (% ID) | SEM | 0 | 0 | 0.049536 | 1.04E-07 | 0.224155 | 0.15366 | 0.091393 | 0.101955 |
| | Mean | 0 | 7.87E-07 | 0.049536 | 0.236671 | 2.22754 | 2.18954 | 4.43653 | 0.679184 |
| Liver Percent ID/g (% ID/g) | SEM | 0 | 7.87E-07 | 0.049536 | 0.236671 | 0.331124 | 0.179805 | 0.048046 | 0.131306 |
| | Mean | 0 | 7.62E-07 | 0.04798 | 0.229237 | 2.15758 | 2.12077 | 1.72129 | 0.657853 |
| | SEM | 0 | 7.62E-07 | 0.04798 | 0.229237 | 0.320724 | 0.174158 | 0.194392 | 0.127182 |
| | | | | | | | | 1.66723 | |
| | | | | | | | | 0.188287 | |

TABLE 14-continued

| Time (h) | | 0 | 0.25 | 0.5 | 0.75 | 6 | 24 | 168 | 336 |
|---|---|---|---|---|---|---|---|---|---|
| Right Kidney Percent ID (% ID) | Mean | 0 | 5.51E-07 | 0.03343 | 0.30096 | 6.55483 | 9.28232 | 8.78883 | 7.03309 |
| Right Kidney Percent ID/g (% ID/g) | SEM | 0 | 5.51E-07 | 0.03343 | 0.30096 | 0.40552 | 0.237102 | 0.135909 | 0.145122 |
|  | Mean | 0 | 2.87E-07 | 0.017443 | 0.157039 | 3.41996 | 4.84335 | 4.58643 | 3.67066 |
| Superficial Cervical Lymph Nodes Percent ID (% ID) | SEM | 0 | 2.87E-07 | 0.017443 | 0.157039 | 0.211939 | 0.124033 | 0.070543 | 0.075382 |
|  | Mean | 0 | 0 | 0 | 0 | 0.083634 | 0.119283 | 0.079562 | 0.065506 |
| Superficial Cervical Lymph Nodes Percent ID/g (% ID/g) | SEM | 0 | 0 | 0 | 0 | 0.009542 | 0.003165 | 0.009958 | 0.012893 |
|  | Mean | 0 | 0 | 0 | 0 | 6.09754 | 8.69663 | 5.8007 | 4.77585 |
| Whole Brain Percent ID (% ID) | SEM | 0 | 0 | 0 | 0 | 0.695718 | 0.230759 | 0.725998 | 0.939968 |
|  | Mean | 6.64123 | 9.64981 | 11.2795 | 12.5369 | 12.9323 | 11.3917 | 10.5087 | 9.42048 |
| Whole Brain Percent ID/g (% ID/g) | SEM | 2.56605 | 2.14697 | 1.5151 | 1.90975 | 1.21462 | 0.926368 | 0.787061 | 0.878424 |
|  | Mean | 3.88961 | 5.63422 | 6.57098 | 7.29032 | 7.62932 | 6.62764 | 5.81735 | 4.91559 |
|  | SEM | 1.53724 | 1.29676 | 0.901465 | 1.07932 | 0.683575 | 0.493438 | 0.38773 | 0.393178 |

TABLE 15

| Time (h) | | 0 | 0.25 | 0.5 | 0.75 | 6 | 24 | 168 | 336 |
|---|---|---|---|---|---|---|---|---|---|
| | | | | | GAPmer E | | | | |
| Amygdala Percent ID (% ID) | Mean | 0.558254 | 0.465608 | 0.374387 | 0.363604 | 0.193671 | 0.145925 | 0.162403 | 0.132189 |
| | SEM | 0.146486 | 0.085887 | 0.061355 | 0.06376 | 0.01351 | 0.019712 | 0.018415 | 0.03282 |
| Amygdala Percent ID/g (% ID/g) | Mean | 12.4998 | 10.4293 | 8.40708 | 8.20394 | 4.3689 | 3.30213 | 3.45771 | 2.5974 |
| | SEM | 3.271 | 1.86942 | 1.3765 | 1.50888 | 0.219988 | 0.428221 | 0.34317 | 0.596509 |
| Basal Ganglia Percent ID (% ID) | Mean | 0.767519 | 0.62213 | 0.549693 | 0.510218 | 0.297928 | 0.264213 | 0.203043 | 0.225742 |
| | SEM | 0.068608 | 0.083157 | 0.062964 | 0.055868 | 0.019889 | 0.007221 | 0.011892 | 0.017126 |
| Basal Ganglia Percent ID/g (% ID/g) | Mean | 7.25586 | 5.88199 | 5.19664 | 4.82425 | 2.82807 | 2.46257 | 1.77921 | 1.8301 |
| | SEM | 0.67508 | 0.804694 | 0.611555 | 0.54622 | 0.229958 | 0.085794 | 0.115155 | 0.104202 |
| Cerebellum Percent ID (% ID) | Mean | 2.25101 | 2.49838 | 2.55948 | 2.42798 | 1.57106 | 1.66827 | 0.814148 | 0.825403 |
| | SEM | 1.04215 | 1.01889 | 0.900513 | 0.90006 | 0.372103 | 0.229306 | 0.281224 | 0.239811 |
| Cerebellum Percent ID/g (% ID/g) | Mean | 8.96768 | 9.93683 | 10.1651 | 9.64754 | 6.18103 | 6.58847 | 2.98996 | 2.83458 |
| | SEM | 4.22932 | 4.12692 | 3.65992 | 3.65352 | 1.44985 | 0.938476 | 1.02327 | 0.777901 |
| Corpus Callosum Percent ID (% ID) | Mean | 0.139098 | 0.137391 | 0.165203 | 0.142788 | 0.201672 | 0.202275 | 0.181619 | 0.161023 |
| | SEM | 0.063509 | 0.040645 | 0.030314 | 0.018416 | 0.006557 | 0.015083 | 0.014325 | 0.012048 |
| Corpus Callosum Percent ID/g (% ID/g) | Mean | 2.52116 | 2.49178 | 3.00274 | 2.59406 | 3.59332 | 3.60851 | 3.05074 | 2.50267 |
| | SEM | 1.15695 | 0.739006 | 0.558865 | 0.341001 | 0.064465 | 0.260085 | 0.1886 | 0.162241 |
| Cortex Percent ID (% ID) | Mean | 1.84462 | 1.96281 | 2.07334 | 2.01485 | 2.27264 | 2.15832 | 1.53834 | 1.35196 |
| | SEM | 0.688596 | 0.505144 | 0.440341 | 0.311568 | 0.065798 | 0.138068 | 0.179699 | 0.159366 |
| Cortex Percent ID/g (% ID/g) | Mean | 3.75097 | 3.99196 | 4.21446 | 4.09784 | 4.62061 | 4.35001 | 2.90653 | 2.37314 |
| | SEM | 1.39426 | 1.02969 | 0.895021 | 0.647193 | 0.113702 | 0.272193 | 0.300372 | 0.222281 |
| Hippocampus Percent ID (% ID) | Mean | 1.67603 | 1.44975 | 1.3333 | 1.24861 | 0.753141 | 0.621775 | 0.655031 | 0.622615 |
| | SEM | 0.395049 | 0.320656 | 0.247148 | 0.243271 | 0.042542 | 0.093431 | 0.051347 | 0.069541 |
| Hippocampus Percent ID/g (% ID/g) | Mean | 13.3312 | 11.5318 | 10.6079 | 9.93388 | 6.04367 | 4.96917 | 4.88174 | 4.32414 |
| | SEM | 3.11226 | 2.52497 | 1.94088 | 1.91141 | 0.22641 | 0.739201 | 0.319607 | 0.503837 |

TABLE 15-continued

| Time (h) | | 0 | 0.25 | 0.5 | 0.75 | 6 | 24 | 168 | 336 |
|---|---|---|---|---|---|---|---|---|---|
| Hypothalamus Percent ID (% ID) | Mean | 1.79208 | 1.26239 | 0.822021 | 0.791454 | 0.309715 | 0.211226 | 0.232952 | 0.209212 |
| | SEM | 0.018149 | 0.044894 | 0.084551 | 0.084724 | 0.038108 | 0.02012 | 0.019585 | 0.00656 |
| Hypothalamus Percent ID/g (% ID/g) | Mean | 31.8662 | 22.4567 | 14.6046 | 14.0554 | 5.4763 | 3.65892 | 3.80714 | 3.15945 |
| | SEM | 0.622153 | 0.985153 | 1.47659 | 1.45413 | 0.653269 | 0.367921 | 0.285807 | 0.194668 |
| Midbrain Percent ID (% ID) | Mean | 8.43844 | 6.14699 | 4.92599 | 4.21695 | 1.50607 | 1.25278 | 1.06369 | 1.03389 |
| | SEM | 0.549632 | 0.264854 | 0.452126 | 0.348737 | 0.115545 | 0.117172 | 0.118459 | 0.088184 |
| Midbrain Percent ID/g (% ID/g) | Mean | 29.2339 | 21.3004 | 17.0721 | 14.6209 | 5.22178 | 4.3333 | 3.41371 | 3.10658 |
| | SEM | 1.78711 | 0.839541 | 1.54884 | 1.22482 | 0.371463 | 0.409401 | 0.363526 | 0.234564 |
| Olfactory Percent ID (% ID) | Mean | 3.09383 | 2.72917 | 2.23702 | 1.91561 | 1.01767 | 0.868984 | 0.679099 | 0.624027 |
| | SEM | 0.423405 | 0.335251 | 0.27618 | 0.246519 | 0.119007 | 0.04595 | 0.047811 | 0.010891 |
| Olfactory Percent ID/g (% ID/g) | Mean | 38.9729 | 34.3305 | 28.1563 | 24.1244 | 12.8281 | 10.802 | 7.93742 | 6.82911 |
| | SEM | 5.78777 | 4.48914 | 3.75756 | 3.37889 | 1.61001 | 0.633288 | 0.584199 | 0.18264 |
| Other (Ventricles) Percent ID (% ID) | Mean | 0.343633 | 0.279426 | 0.239164 | 0.209768 | 0.100025 | 0.08652 | 0.085407 | 0.085755 |
| | SEM | 0.059376 | 0.046773 | 0.034903 | 0.025436 | 0.005734 | 0.009182 | 0.004352 | 0.009717 |
| Other (Ventricles) Percent ID/g (% ID/g) | Mean | 15.7006 | 12.7644 | 10.9255 | 9.58606 | 4.63014 | 3.97221 | 3.61689 | 3.41809 |
| | SEM | 2.70418 | 2.12314 | 1.58033 | 1.15794 | 0.165485 | 0.42827 | 0.121301 | 0.373455 |
| Septal Area Percent ID (% ID) | Mean | 0.073996 | 0.058791 | 0.063152 | 0.050917 | 0.02835 | 0.026065 | 0.016707 | 0.018377 |
| | SEM | 0.045267 | 0.028474 | 0.016226 | 0.011536 | 0.002718 | 0.002504 | 0.001675 | 7.06E−05 |
| Septal Area Percent ID/g (% ID/g) | Mean | 6.01601 | 4.78158 | 5.12945 | 4.13132 | 2.29807 | 2.04259 | 1.24867 | 1.33379 |
| | SEM | 3.70113 | 2.33093 | 1.33813 | 0.949408 | 0.276602 | 0.182851 | 0.154458 | 0.0225 |
| Thalamus Percent ID (% ID) | Mean | 0.355264 | 0.293372 | 0.267919 | 0.271126 | 0.16181 | 0.136424 | 0.194221 | 0.189016 |
| | SEM | 0.107897 | 0.058708 | 0.039629 | 0.057802 | 0.017602 | 0.027896 | 0.006076 | 0.011428 |
| Thalamus Percent ID/g (% ID/g) | Mean | 5.2993 | 4.37887 | 4.00206 | 4.04775 | 2.40781 | 2.02639 | 2.69809 | 2.39589 |
| | SEM | 1.59833 | 0.871224 | 0.598227 | 0.861554 | 0.226053 | 0.394538 | 0.073301 | 0.192872 |
| White Matter Percent ID (% ID) | Mean | 1.29678 | 0.924978 | 0.718283 | 0.651161 | 0.254615 | 0.201785 | 0.189864 | 0.183236 |
| | SEM | 0.078326 | 0.045632 | 0.010753 | 0.044752 | 0.018402 | 0.019568 | 0.008725 | 0.017793 |

TABLE 15-continued

| Time (h) | | 0 | 0.25 | 0.5 | 0.75 | 6 | 24 | 168 | 336 |
|---|---|---|---|---|---|---|---|---|---|
| White Matter Percent ID/g (% ID/g) | Mean | 24.0762 | 17.1758 | 13.3413 | 12.1025 | 4.75988 | 3.7307 | 3.28689 | 2.97632 |
| | SEM | 1.35368 | 0.787724 | 0.180212 | 0.879991 | 0.390942 | 0.330414 | 0.145634 | 0.272604 |
| Whole Brain Percent ID (% ID) | Mean | 22.6306 | 18.8312 | 16.329 | 14.815 | 8.66836 | 7.84457 | 6.01653 | 5.66245 |
| | SEM | 1.68624 | 1.35974 | 1.61868 | 1.73388 | 0.673152 | 0.358564 | 0.670171 | 0.594421 |
| Whole Brain Percent ID/g (% ID/g) | Mean | 13.6667 | 11.3745 | 9.8642 | 8.95243 | 5.23969 | 4.71044 | 3.37774 | 2.9616 |
| | SEM | 1.05573 | 0.870626 | 1.01123 | 1.08442 | 0.4077 | 0.215852 | 0.355915 | 0.271713 |
| Comparative GAPmer G | | | | | | | | | |
| Amygdala Percent ID (% ID) | Mean | 0.07025 | 0.157133 | 0.182216 | 0.204618 | 0.343688 | 0.239396 | 0.238917 | 0.269154 | 0.233677 |
| | SEM | 0.063589 | 0.103704 | 0.085755 | 0.077849 | 0.030438 | 0.005162 | 0.01289 | 0.008577 | 0.01741 |
| Amygdala Percent ID/g (% ID/g) | Mean | 1.59871 | 3.55317 | 4.09803 | 4.58765 | 7.5081 | 5.19617 | 5.055 | 5.67473 | 4.60241 |
| | SEM | 1.45175 | 2.37755 | 1.9771 | 1.79353 | 0.641745 | 0.156614 | 0.257744 | 0.207565 | 0.250856 |
| Basal Ganglia Percent ID (% ID) | Mean | 0.117021 | 0.21681 | 0.26589 | 0.306323 | 0.381952 | 0.370599 | 0.337719 | 0.336959 | 0.313839 |
| | SEM | 0.076931 | 0.088946 | 0.044903 | 0.051348 | 0.066725 | 0.023366 | 0.027073 | 0.005895 | 0.040156 |
| Basal Ganglia Percent ID/g (% ID/g) | Mean | 1.0588 | 1.96201 | 2.40278 | 2.76795 | 3.51276 | 3.33342 | 2.95949 | 2.87515 | 2.55187 |
| | SEM | 0.696112 | 0.806687 | 0.414127 | 0.475621 | 0.611781 | 0.196289 | 0.218288 | 0.033142 | 0.308451 |
| Cerebellum Percent ID (% ID) | Mean | 0.377037 | 1.0096 | 1.6223 | 1.9812 | 2.21016 | 2.45293 | 2.25788 | 1.87032 | 1.68511 |
| | SEM | 0.190099 | 0.127709 | 0.076476 | 0.217865 | 0.397162 | 0.248084 | 0.392909 | 0.16277 | 0.129536 |
| Cerebellum Percent ID/g (% ID/g) | Mean | 1.43098 | 3.80814 | 6.10942 | 7.43788 | 8.66211 | 9.3077 | 8.35519 | 6.85223 | 5.74023 |
| | SEM | 0.73404 | 0.520186 | 0.338803 | 0.743845 | 1.65949 | 0.83535 | 1.37758 | 0.568067 | 0.397753 |
| Corpus Callosum Percent ID (% ID) | Mean | 0.022238 | 0.055967 | 0.080598 | 0.09326 | 0.320271 | 0.284835 | 0.303873 | 0.289287 | 0.24998 |
| | SEM | 0.02222 | 0.041424 | 0.041437 | 0.037288 | 0.063501 | 0.024991 | 0.027853 | 0.028854 | 0.028791 |
| Corpus Callosum Percent ID/g (% ID/g) | Mean | 0.39108 | 0.9794 | 1.40316 | 1.61839 | 5.59917 | 4.88872 | 5.14219 | 4.79623 | 3.87539 |
| | SEM | 0.39077 | 0.730546 | 0.730645 | 0.654849 | 1.08746 | 0.386997 | 0.447732 | 0.457439 | 0.399475 |
| Cortex Percent ID (% ID) | Mean | 0.220028 | 0.633967 | 0.867894 | 1.11482 | 2.9228 | 2.62081 | 2.57875 | 2.38031 | 2.0868 |
| | SEM | 0.20834 | 0.32453 | 0.269076 | 0.261392 | 0.426537 | 0.262245 | 0.251051 | 0.250084 | 0.291286 |

TABLE 15-continued

| Time (h) | | 0 | 0.25 | 0.5 | 0.75 | 6 | 24 | 168 | 336 |
|---|---|---|---|---|---|---|---|---|---|
| Cortex Percent ID/g (% ID/g) | Mean | 0.436481 | 1.2498 | 1.70512 | 2.18607 | 5.78025 | 5.13609 | 4.93298 | 4.41018 | 
| | | | | | | | | | | 3.66582 |
| | SEM | 0.413775 | 0.648254 | 0.538842 | 0.519404 | 0.806778 | 0.471369 | 0.420487 | 0.441617 |
| Hippo-campus Percent ID (% ID) | Mean | 0.35119 | 0.748223 | 0.836605 | 1.01328 | 1.24774 | 0.976929 | 0.9861 | 1.09848 |
| | | | | | | | | | | 0.461271 |
| | | | | | | | | | | 0.96287 |
| | SEM | 0.308774 | 0.413338 | 0.32756 | 0.327609 | 0.201253 | 0.042564 | 0.049536 | 0.086952 |
| Hippo-campus Percent ID/g (% ID/g) | Mean | 2.75325 | 5.82967 | 6.49002 | 7.83626 | 9.76959 | 7.54148 | 7.41702 | 8.09684 |
| | | | | | | | | | | 0.061749 |
| | | | | | | | | | | 6.64111 |
| | SEM | 2.43034 | 3.26845 | 2.58722 | 2.55293 | 1.5319 | 0.392925 | 0.41303 | 0.588516 |
| Hypo-thalamus Percent ID (% ID) | Mean | 0.310676 | 0.556035 | 0.632061 | 0.647227 | 0.468645 | 0.316754 | 0.294092 | 0.307265 |
| | | | | | | | | | | 0.324495 |
| | | | | | | | | | | 0.277475 |
| | SEM | 0.19552 | 0.167087 | 0.086168 | 0.096156 | 0.072388 | 0.015545 | 0.029589 | 0.00855 |
| Hypo-thalamus Percent ID/g (% ID/g) | Mean | 5.45031 | 9.68302 | 10.9582 | 11.188 | 7.93032 | 5.33595 | 4.83903 | 4.86859 |
| | | | | | | | | | | 0.052414 |
| | | | | | | | | | | 4.20649 |
| | SEM | 3.45552 | 2.98698 | 1.56155 | 1.64189 | 1.23903 | 0.312465 | 0.488397 | 0.069093 |
| Midbrain Percent ID (% ID) | Mean | 4.33614 | 4.6489 | 4.70957 | 4.77253 | 2.81178 | 2.22989 | 2.22287 | 2.24199 |
| | | | | | | | | | | 0.753838 |
| | | | | | | | | | | 2.04046 |
| | SEM | 1.09108 | 0.472434 | 0.556198 | 0.860335 | 0.311395 | 0.227459 | 0.239223 | 0.196013 |
| Midbrain Percent ID/g (% ID/g) | Mean | 14.6252 | 15.6356 | 15.8197 | 16.0115 | 9.51511 | 7.46745 | 7.27228 | 7.12792 |
| | | | | | | | | | | 0.167723 |
| | | | | | | | | | | 6.11257 |
| | SEM | 3.79365 | 1.65574 | 1.83494 | 2.81171 | 0.986306 | 0.733658 | 0.693298 | 0.567999 |
| Olfac-tory Percent ID (% ID) | Mean | 0.149962 | 0.632525 | 1.03599 | 1.26658 | 1.24326 | 1.13771 | 0.958425 | 0.900536 |
| | | | | | | | | | | 0.444177 |
| | | | | | | | | | | 0.821473 |
| | SEM | 0.145638 | 0.32823 | 0.247651 | 0.241037 | 0.123074 | 0.089789 | 0.128224 | 0.064184 |
| Olfac-tory Percent ID/g (% ID/g) | Mean | 1.87276 | 7.74847 | 12.5673 | 15.3101 | 15.3729 | 13.899 | 11.474 | 10.5042 |
| | | | | | | | | | | 0.067165 |
| | | | | | | | | | | 9.0143 |
| | SEM | 1.82129 | 4.07012 | 2.99221 | 2.78286 | 1.67593 | 0.859927 | 1.24418 | 0.559225 |
| Other (Vent-ricles) Percent ID (% ID) | Mean | 0.103703 | 0.185432 | 0.194473 | 0.217117 | 0.197903 | 0.151701 | 0.149739 | 0.171693 |
| | | | | | | | | | | 0.567696 |
| | | | | | | | | | | 0.151244 |
| | SEM | 0.064701 | 0.053473 | 0.042229 | 0.048518 | 0.031704 | 0.012028 | 0.013804 | 0.020145 |
| Other (Vent-ricles) Percent ID/g (% ID/g) | Mean | 4.78859 | 8.43852 | 8.78707 | 9.76454 | 8.6628 | 6.77372 | 6.44925 | 7.21803 |
| | | | | | | | | | | 0.013969 |
| | | | | | | | | | | 5.96959 |
| | SEM | 3.07256 | 2.59532 | 1.96278 | 2.10578 | 1.32337 | 0.539855 | 0.494456 | 0.807697 |
| Septal Area Percent ID (% ID) | Mean | 0.001539 | 0.006606 | 0.015932 | 0.018396 | 0.039833 | 0.035454 | 0.030647 | 0.032093 |
| | | | | | | | | | | 0.44098 |
| | | | | | | | | | | 0.029051 |
| | SEM | 0.001539 | 0.003583 | 8.82E−05 | 0.003932 | 0.01193 | 0.003715 | 0.009077 | 0.001693 |
| Septal Area Percent ID/g (% ID/g) | Mean | 0.120801 | 0.527008 | 1.27118 | 1.46742 | 3.10952 | 2.7415 | 2.29345 | 2.38383 |
| | | | | | | | | | | 0.005864 |
| | | | | | | | | | | 1.99012 |
| | SEM | 0.120767 | 0.282368 | 0.015955 | 0.309541 | 0.891273 | 0.298319 | 0.674918 | 0.108081 | 0.356811 |

TABLE 15-continued

| Time (h) | | 0 | 0.25 | 0.5 | 0.75 | 6 | 24 | 168 | 336 |
|---|---|---|---|---|---|---|---|---|---|
| Thalamus Percent ID (% ID) | Mean | 0.092871 | 0.150887 | 0.196566 | 0.219307 | 0.330367 | 0.230327 | 0.239492 | 0.267022 | 0.259107 |
| | SEM | 0.087919 | 0.09502 | 0.106559 | 0.089875 | 0.103733 | 0.028211 | 0.016836 | 0.038453 | 0.035847 |
| Thalamus Percent ID/g (% ID/g) | Mean | 1.35285 | 2.1754 | 2.82156 | 3.12705 | 4.75564 | 3.29927 | 3.32141 | 3.61865 | 3.31424 |
| | SEM | 1.28417 | 1.39631 | 1.56503 | 1.3048 | 1.432 | 0.397001 | 0.246257 | 0.503694 | 0.400364 |
| White Matter Percent ID (% ID) | Mean | 0.488571 | 0.647725 | 0.639413 | 0.682258 | 0.413888 | 0.344319 | 0.331351 | 0.343591 | 0.309396 |
| | SEM | 0.165272 | 0.08416 | 0.056944 | 0.104846 | 0.047088 | 0.032138 | 0.028182 | 0.022572 | 0.029752 |
| White Matter Percent ID/g (% ID/g) | Mean | 8.95911 | 11.7844 | 11.5942 | 12.3289 | 7.60563 | 6.27336 | 5.76995 | 5.89313 | 4.99564 |
| | SEM | 3.18773 | 1.61296 | 0.885738 | 1.64353 | 0.721249 | 0.575411 | 0.454626 | 0.362268 | 0.449234 |
| Whole Brain Percent ID (% ID) | Mean | 6.64123 | 9.64981 | 11.2795 | 12.5369 | 12.9323 | 11.3917 | 10.9299 | 10.5087 | 9.42048 |
| | SEM | 2.56605 | 2.14697 | 1.5151 | 1.90975 | 1.21462 | 0.926368 | 1.03752 | 0.787061 | 0.878424 |
| Whole Brain Percent ID/g (% ID/g) | Mean | 3.88961 | 5.63422 | 6.57098 | 7.29032 | 7.62932 | 6.62764 | 6.20152 | 5.81735 | 4.91559 |
| | SEM | 1.53724 | 1.29676 | 0.901465 | 1.07932 | 0.683575 | 0.493438 | 0.519785 | 0.38773 | 0.393178 |

Evaluation of TAU GAPmers in Human iPSC-Derived Neurons

Next, the efficacy of one of the lead GAPmers (GAPmer E) was compared with the efficacy of the Ionis TAU GAPmer (GAPmer G) in reducing TAU mRNA in human iPSC-derived neurons (iNeurons). iNeurons were treated with various doses of both GAPmers for a total period of 72 hours and collected total cellular RNA. TAU mRNA was measured with 6 different assays as well as with 3R and 4R TAU specific assays (Table 16). Both compounds dose-dependently reduced TAU mRNA levels. However, GAPmer E consistently showed ~4-5 times smaller $IC_{50}$ values indicating that the GAPmer is more potent than GAPmer G.

TABLE 16

| Log Dose (mM) | GAPmer G | | | GAPmer E | | |
|---|---|---|---|---|---|---|
| | Avg | SEM | N | Avg | SEM | N |
| total TAU mRNA assay JPNV-1 | | | | | | |
| −4.41 | 100.00 | 5.26 | 2.00 | 100.00 | 8.90 | 2.00 |
| −4.11 | 105.73 | 7.76 | 2.00 | 66.20 | 7.97 | 2.00 |
| −3.81 | 76.81 | 3.49 | 2.00 | 57.05 | 0.89 | 2.00 |
| −3.51 | 59.15 | 5.15 | 2.00 | 53.71 | 4.27 | 2.00 |
| −3.20 | 73.86 | 3.19 | 2.00 | 56.45 | 3.76 | 2.00 |
| −2.90 | 75.20 | 1.16 | 2.00 | 52.56 | 2.43 | 2.00 |
| −2.60 | 60.12 | 3.61 | 2.00 | 42.05 | 2.25 | 2.00 |
| −2.30 | 51.36 | 4.79 | 2.00 | 39.61 | 3.82 | 2.00 |
| −2.00 | 43.01 | 2.99 | 2.00 | 30.64 | 1.39 | 2.00 |
| −1.70 | 43.88 | 1.82 | 2.00 | 33.58 | 1.55 | 2.00 |
| total TAU mRNA assay JPNV-2 | | | | | | |
| −4.41 | 100.00 | 6.41 | 2.00 | 100.00 | 6.21 | 2.00 |
| −4.11 | 24.84 | 1.80 | 2.00 | 20.00 | 1.19 | 2.00 |
| −3.81 | 56.59 | 2.16 | 2.00 | 48.73 | 4.79 | 2.00 |
| −3.51 | 51.51 | 3.69 | 2.00 | 35.98 | 1.63 | 2.00 |
| −3.20 | 51.49 | 1.82 | 2.00 | 36.62 | 2.60 | 2.00 |
| −2.90 | 53.65 | 1.19 | 2.00 | 37.02 | 0.96 | 2.00 |
| −2.60 | 40.99 | 2.12 | 2.00 | 29.15 | 1.35 | 2.00 |
| −2.30 | 39.59 | 1.79 | 2.00 | 29.71 | 2.44 | 2.00 |
| −2.00 | 34.02 | 1.03 | 2.00 | 25.37 | 1.82 | 2.00 |
| −1.70 | 29.58 | 2.78 | 2.00 | 24.24 | 0.94 | 2.00 |
| 3R TAU mRNA assay | | | | | | |
| −4.41 | 100.00 | 5.06 | 2.00 | 100.00 | 6.68 | 2.00 |
| −4.11 | 98.52 | 6.40 | 2.00 | 70.06 | 4.91 | 2.00 |
| −3.81 | 67.36 | 2.95 | 2.00 | 51.92 | 1.81 | 2.00 |
| −3.51 | 73.28 | 5.54 | 2.00 | 46.44 | 2.02 | 2.00 |
| −3.20 | 78.75 | 7.03 | 2.00 | 54.94 | 4.38 | 2.00 |
| −2.90 | 72.16 | 3.92 | 2.00 | 49.60 | 1.83 | 2.00 |
| −2.60 | 55.58 | 6.73 | 2.00 | 36.87 | 3.68 | 2.00 |
| −2.30 | 55.57 | 2.90 | 2.00 | 38.88 | 1.99 | 2.00 |
| −2.00 | 46.08 | 3.19 | 2.00 | 31.61 | 3.47 | 2.00 |
| −1.70 | 46.00 | 2.33 | 2.00 | 28.60 | 1.53 | 2.00 |
| 4R TAU mRNA assay | | | | | | |
| −4.41 | 100.00 | 8.07 | 2.00 | 100.00 | 8.66 | 2.00 |
| −4.11 | 98.95 | 10.45 | 2.00 | 68.72 | 10.10 | 2.00 |
| −3.81 | 71.44 | 7.35 | 2.00 | 66.14 | 9.41 | 2.00 |
| −3.51 | 86.77 | 10.41 | 2.00 | 45.76 | 5.40 | 2.00 |
| −3.20 | 89.66 | 4.77 | 2.00 | 59.82 | 4.93 | 2.00 |
| −2.90 | 75.93 | 5.07 | 2.00 | 51.76 | 4.18 | 2.00 |

TABLE 16-continued

| Log Dose (mM) | GAPmer G | | | GAPmer E | | |
|---|---|---|---|---|---|---|
| | Avg | SEM | N | Avg | SEM | N |
| −2.60 | 74.03 | 5.98 | 2.00 | 44.10 | 5.51 | 2.00 |
| −2.30 | 62.73 | 4.05 | 2.00 | 43.65 | 5.14 | 2.00 |
| −2.00 | 60.46 | 5.68 | 2.00 | 38.37 | 4.26 | 2.00 |
| −1.70 | 61.52 | 5.36 | 2.00 | 28.82 | 1.55 | 2.00 |
| total TAU mRNA assay B01 | | | | | | |
| −4.41 | 100.00 | 4.14 | 2.00 | 100.00 | 5.90 | 2.00 |
| −4.11 | 111.85 | 13.42 | 2.00 | 67.28 | 2.70 | 2.00 |
| −3.81 | 58.26 | 1.91 | 2.00 | 45.92 | 1.66 | 2.00 |
| −3.51 | 57.40 | 5.01 | 2.00 | 39.63 | 3.68 | 2.00 |
| −3.20 | 51.69 | 1.20 | 2.00 | 37.51 | 1.63 | 2.00 |
| −2.90 | 49.11 | 3.05 | 2.00 | 35.71 | 3.17 | 2.00 |
| −2.60 | 43.08 | 2.04 | 2.00 | 29.67 | 1.24 | 2.00 |
| −2.30 | 36.56 | 3.01 | 2.00 | 27.05 | 1.49 | 2.00 |
| −2.00 | 33.47 | 1.85 | 2.00 | 25.92 | 1.70 | 2.00 |
| −1.70 | 31.96 | 1.35 | 2.00 | 23.63 | 1.12 | 2.00 |
| total TAU mRNA assay B02 | | | | | | |
| −4.41 | 100.00 | 18.06 | 2.00 | 100.00 | 16.10 | 2.00 |
| −4.11 | 89.43 | 13.92 | 2.00 | 86.50 | 6.39 | 2.00 |
| −3.81 | 76.62 | 4.87 | 2.00 | 73.14 | 3.78 | 2.00 |
| −3.51 | 76.28 | 5.80 | 2.00 | 70.26 | 5.44 | 2.00 |
| −3.20 | 57.42 | 22.00 | 2.00 | 62.15 | 22.69 | 2.00 |
| −2.90 | 56.07 | 17.26 | 2.00 | 66.44 | 25.75 | 2.00 |
| −2.60 | 56.68 | 5.62 | 2.00 | 50.53 | 6.40 | 2.00 |
| −2.30 | 56.02 | 5.75 | 2.00 | 54.94 | 3.18 | 2.00 |
| −2.00 | 58.70 | 4.16 | 2.00 | 48.44 | 2.30 | 2.00 |
| −1.70 | 60.05 | 4.55 | 2.00 | 50.47 | 2.71 | 2.00 |
| total TAU mRNA assay B04 | | | | | | |
| −4.41 | 100.00 | 6.21 | 2.00 | 100.00 | 9.22 | 2.00 |
| −4.11 | 99.83 | 7.72 | 2.00 | 71.27 | 4.72 | 2.00 |
| −3.81 | 91.52 | 9.34 | 2.00 | 59.20 | 3.96 | 2.00 |
| −3.51 | 91.28 | 6.40 | 2.00 | 62.05 | 3.23 | 2.00 |
| −3.20 | 96.69 | 3.34 | 2.00 | 65.94 | 4.10 | 2.00 |
| −2.90 | 88.52 | 4.15 | 2.00 | 57.63 | 4.19 | 2.00 |
| −2.60 | 73.91 | 6.53 | 2.00 | 47.11 | 1.37 | 2.00 |
| −2.30 | 72.26 | 3.42 | 2.00 | 46.09 | 3.69 | 2.00 |
| −2.00 | 71.32 | 2.46 | 2.00 | 43.76 | 2.19 | 2.00 |
| −1.70 | 74.91 | 5.87 | 2.00 | 42.52 | 3.95 | 2.00 |
| total TAU mRNA assay B06 | | | | | | |
| −4.41 | 100.00 | 105.59 | 2.00 | 100.00 | 110.27 | 2.00 |
| −4.11 | 124.26 | 111.64 | 2.00 | 51.19 | 72.99 | 2.00 |
| −3.81 | 150.32 | 81.10 | 2.00 | 42.93 | 62.90 | 2.00 |
| −3.51 | 103.10 | 62.46 | 2.00 | 34.99 | 59.23 | 2.00 |
| −3.20 | 53.75 | 77.99 | 2.00 | 44.52 | 62.24 | 2.00 |
| −2.90 | 66.83 | 79.40 | 2.00 | 45.46 | 57.96 | 2.00 |
| −2.60 | 105.07 | 63.48 | 2.00 | 14.83 | 46.37 | 2.00 |
| −2.30 | 55.09 | 54.23 | 2.00 | 39.97 | 43.68 | 2.00 |
| −2.00 | 39.68 | 45.41 | 2.00 | 23.71 | 33.79 | 2.00 |
| −1.70 | 94.51 | 46.33 | 2.00 | 42.82 | 37.02 | 2.00 |

Method of Treatment

An adult human suffering from a tauopathy such as Alzheimer's disease (AD) is administered via any suitable route of administration such as intrathecal or intracerebroventricular route of administration a therapeutically effective compound of an oligonucleotide of the present disclosure, for example, an oligonucleotide having a nucleobase sequence corresponding to SEQ ID NO: 1 and modified according to the present disclosure. Suitable routes of administration may include systemic administration such as intravenous or subcutaneous routes of administration or administration directly to the CNS via intrathecal or intracerebroventricular routes of administration. Treatment is continued until one or more symptoms of tauopathy such as AD is ameliorated, or for example, tau protein levels are reduced.

What is claimed is:

1. A chimeric oligonucleotide complementary to at least a portion of the MAPT gene represented by Formula (VI):

$$5'X-Y-Z3' \quad (VI),$$

wherein

X-Y-Z is a chimeric oligonucleotide comprising a sequence of 18 to 22 nucleosides, and is optionally conjugated at the 5' and/or 3' end to a ligand targeting group;

X is a domain comprising a sequence of modified nucleosides that is 3-10 nucleosides in length;

Z is a domain comprising a sequence of modified nucleosides that is 3-10 nucleosides in length; and Y is a domain comprising a sequence of 2 to 10 2'-deoxy-nucleosides linked through thiophosphate intersubunit linkages, and wherein the oligonucleotide shows affinity to at least one of SEQ ID NO: 3, SEQ ID NO: 4, SEQ ID NO:5 or SEQ ID NO:6, wherein the X and/or Z domain comprises one or more oligonucleotide where the modification is 2'-O-methoxyethoxy-N3'→P5'.

2. The chimeric oligonucleotide of claim 1, wherein the Y domain is 6 to 10 nucleosides in length.

3. The chimeric oligonucleotide of claim 1, wherein the X and/or Z domains comprise a sequence of modified nucleosides linked through N3'→P5' phosphoramidate or N3'→P5' thiophosphoramidate intersubunit linkages.

4. The chimeric oligonucleotide of claim 1, wherein the Y domain comprises at least one phosphodiester intersubunit linkage.

5. The chimeric oligonucleotide of claim 1, wherein the Y domain consists of 2'-deoxy-nucleosides linked through thiophosphate intersubunit linkages, and optionally one or two phosphodiester intersubunit linkage.

6. The chimeric oligonucleotide of claim 1, wherein the X domain comprises modified nucleosides where the modification is independently selected from the group consisting of 2'-F, 2'-F—N3'→P5', 2'-OMe, 2'-OMe-N3'→P5', 2'-O-methoxyethoxy, 2'-O-methoxyethoxy-N3'→P5', conformationally restricted nucleosides, 2'-OH—N3'→P5' thiophosphoramidate and 2'-OH—N3'→P5' phosphoramidate.

7. The chimeric oligonucleotide of claim 1, wherein the functional domain of Z comprises modified nucleosides where the modification is selected from the group consisting of 2'-F, 2'-F—N3'→P5', 2'-OMe, 2'-OMe-N3'→P5', 2'-O-methoxyethoxy, 2'-O-methoxyethoxy-N3'→P5', conformationally restricted nucleosides, 2'-OH—N3'→P5' thiophosphoramidate and 2'-OH—N3'→P5' phosphoramidate.

8. The chimeric oligonucleotide of claim 1, wherein the X and/or Z domains comprise one or more 2'-deoxy-nucleosides linked through a N3'→P5' phosphoramidate intersubunit linkage.

9. The chimeric oligonucleotide of claim 1, wherein the X and Z domains comprise one or more 2'-arabino-F and/or 2'-ribo-F modified nucleoside, wherein each said nucleoside is independently linked through at least one of an N3'→P5' phosphoramidate or N3'→P5' thiophosphoramidate intersubunit linkage.

10. The chimeric oligonucleotide of claim 1, wherein the X and Z domains comprise one or more 2'-OMe modified nucleosides, wherein each said nucleoside is independently linked through at least one of N3'→P5' phosphoramidate, N3'→P5' thiophosphoramidate, or thiophosphate intersubunit linkages.

11. The chimeric oligonucleotide of claim 1, wherein the modified nucleosides in each of the X and Z domains are 2'-OMe modified nucleosides linked through thiophosphate intersubunit linkages, and wherein the modified nucleosides include 5-methylcytosine nucleobases.

12. The chimeric oligonucleotide of claim 1, wherein the modified nucleosides include 2,6-diaminopurine nucleobases.

13. The chimeric oligonucleotide of claim 1, wherein the modified nucleosides include 5-methyluracil nucleobases.

14. The chimeric oligonucleotide of claim 1, wherein the modified nucleosides include 2,6-diaminopurine nucleobases, but not adenine and 5-methyluracil nucleobases.

15. The chimeric oligonucleotide of claim 1, wherein the Y domain comprises 6-8 2'-deoxy-nucleosides.

16. The chimeric oligonucleotide of claim 1, wherein the modified nucleosides in each of the X and Z domains comprise 2'-OMe modified nucleosides and conformationally restricted nucleosides optionally linked through thiophosphate intersubunit linkages, and wherein the 2'-OMe modified nucleosides include 5-methylcytosine nucleobases.

17. The chimeric oligonucleotide of claim 1, wherein the modified nucleosides in each of the X and Z domains comprise 2'-OMe and conformationally restricted nucleosides.

18. The chimeric oligonucleotide of claim 1, wherein the modified nucleosides in each of the X and Z domains comprise conformationally restricted nucleosides and, wherein at least one modified nucleoside includes a N3'→P5' phosphoramidate or a N3'→P5' thiophosphoramidate intersubunit linkage.

19. The chimeric oligonucleotide of claim 1, wherein the Y domain comprises 7-8 2'-deoxy-nucleosides.

20. The chimeric oligonucleotide of claim 1, wherein the modified nucleosides include 2'-OMe modified nucleosides, and the 2'-OMe modified nucleosides include 5-methyluracil nucleobases.

21. The chimeric oligonucleotide of claim 1, wherein the Y domain comprises 9-10 2'-deoxy-nucleosides.

22. The chimeric oligonucleotide of claim 1, wherein the X and Z domains comprise nucleotides represented by the Formula (A1):

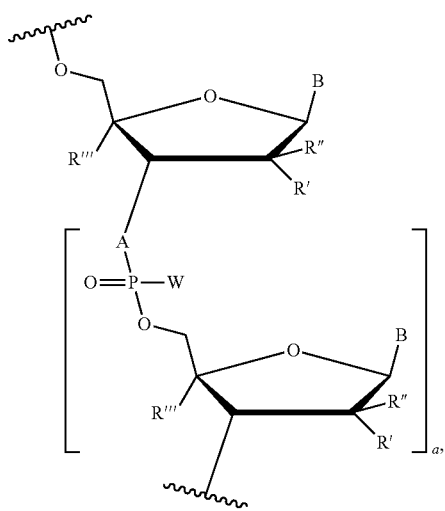

(A1)

wherein

A is independently in each instance NH or O;

B is independently in each instance an unmodified or modified nucleobase;

W is independently in each instance OR or SR, where R is H or a positively charged counter ion;

R' and R" are each independently in each instance selected from the group consisting of H, F, Cl, OH, OMe, Me, and O-methoxyethoxy;

R'" is H, or R' and R'" together form —O—CH$_2$— or —O—(CH$_2$)$_2$—, and a is an integer of 3 to 9, wherein when R', R" and R'" are each H, then A is NH, and optionally when A is O, then W is SR.

23. The chimeric oligonucleotide of claim 1, wherein the X domain comprises one or more oligonucleotide where the modification is 2'-O-methoxyethoxy-N3'→P5'.

24. The chimeric oligonucleotide of claim 1, wherein the Z domain comprises one or more oligonucleotide where the modification is 2'-O-methoxyethoxy-N3'→P5'.

25. The chimeric oligonucleotide of claim 1, wherein the nucleobase sequence of the oligonucleotide corresponds to SEQ ID NO: 1, SEQ ID NO: 40, SEQ ID NO: 41 or SEQ ID NO: 42.

26. A pharmaceutical composition comprising an oligonucleotide of claim 1 and a pharmaceutically acceptable excipient.

27. The pharmaceutical composition of claim 26, wherein the composition is suitable for intrathecal or intracerebroventricular delivery.

28. A method of inhibiting MAPT gene expression in a CNS cell comprising contacting the cell with an oligonucleotide of claim 1.

29. A method of inhibiting transcription of MAPT mRNA in a CNS cell comprising contacting the cell with an oligonucleotide of claim 1.

30. The oligonucleotide of claim 1, wherein said oligonucleotide complexed with an MAPT gene has a melting temperature (Tm) of >37° C.

31. A method of inhibiting expression of a MAPT mRNA in a CNS cell comprising contacting the cell with an oligonucleotide or composition comprising an oligonucleotide of claim 1, wherein the oligonucleotide contains a nucleobase sequence that is complementary or hybridizes to at least a portion of the MAPT mRNA.

32. A method of modulating expression of a MAPT gene by contacting a target nucleic acid with an antisense compound comprising an oligonucleotide of claim 1, wherein the oligonucleotide contains a nucleobase sequence that is complementary or hybridizes to at least a portion of the MAPT gene.

* * * * *

SEQUENCE LISTING

<160> NUMBER OF SEQ ID NOS: 44

<210> SEQ ID NO 1
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1
gcttttactg accatgcgag                                                    20

<210> SEQ ID NO 2
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 2
gcuuutactg accatgcgag                                                    20

<210> SEQ ID NO 3
<211> LENGTH: 20
<212> TYPE: DNA
<213> ORGANISM: Homo sapiens

<400> SEQUENCE: 3
ctcgcatggt cagtaaaagc                                                    20

<210> SEQ ID NO 4
<211> LENGTH: 20
<212> TYPE: DNA
<213> ORGANISM: Homo sapiens

<400> SEQUENCE: 4
ggaagcgatg acaaaaaagc                                                    20

<210> SEQ ID NO 5
<211> LENGTH: 20
<212> TYPE: DNA
<213> ORGANISM: Homo sapiens

<400> SEQUENCE: 5
ggctcaaagg ataatatcaa                                                    20

<210> SEQ ID NO 6
<211> LENGTH: 20
<212> TYPE: DNA
<213> ORGANISM: Homo sapiens

<400> SEQUENCE: 6
ggtccctgga caatatcacc                                                    20

<210> SEQ ID NO 7
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 7
ccttccctga aggttcctcc                                                    20

<210> SEQ ID NO 8
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 8
cctccaagtg tggctcatta                                                    20

<210> SEQ ID NO 9
<211> LENGTH: 17
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

```
<400> SEQUENCE: 9
cagtggtccg tactcca                                                    17

<210> SEQ ID NO 10
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 10
attgaaaccc acaagctgac                                                 20

<210> SEQ ID NO 11
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 11
tcaggtgaac tttgaaccag                                                 20

<210> SEQ ID NO 12
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 12
ccaagtgtgg ctcattaggc a                                               21

<210> SEQ ID NO 13
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 13
gagtccagtc gaagattggg t                                               21

<210> SEQ ID NO 14
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 14
aggcgggaag gtgcaaata                                                  19

<210> SEQ ID NO 15
<211> LENGTH: 21
<212> TYPE: DNA
<213> ORGANISM: Artificial Sequence
```

-continued

```
<220> FEATURE:
<221> NAME/KEY: source
<223> OTHER INFORMATION: /note="Description of Artificial Sequence:
      Synthetic primer"

<400> SEQUENCE: 15
cgggaaggtg cagataatta a                                            21

<210> SEQ ID NO 16
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 16
caatcttcga ctggactctg                                              20

<210> SEQ ID NO 17
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 17
tggacttgac attcttcagg                                              20

<210> SEQ ID NO 18
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 18
gaggagacat tgctgagatg                                              20

<210> SEQ ID NO 19
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 19
cttccatcac ttcgaactcc                                              20

<210> SEQ ID NO 20
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 20
ccaatcttcg actggactct gt                                           22
```

<210> SEQ ID NO 21
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 21
ggcgagtcta ccatgtcgat g    21

<210> SEQ ID NO 22
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 22
gccacctcct ggtttatgat g    21

<210> SEQ ID NO 23
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 23
tatttgcaca ctgccgcct    19

<210> SEQ ID NO 24
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 24
aaggtgaagg tcggagtcaa c    21

<210> SEQ ID NO 25
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 25
ggggtcattg atggcaacaa ta    22

<210> SEQ ID NO 26
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 26
ttatcccgga agctaaacag tgg                                           23

<210> SEQ ID NO 27
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 27
gtagcctcat attctcctgt gc                                            22

<210> SEQ ID NO 28
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 28
gggagaccca aagggagta t                                              21

<210> SEQ ID NO 29
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 29
ggagcggaat ctctctagtg ag                                            22

<210> SEQ ID NO 30
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 30
actataatgc aacgactccc ct                                            22

<210> SEQ ID NO 31
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 31
cttcctgctg aatacgggct g                                             21

<210> SEQ ID NO 32
<211> LENGTH: 21
<212> TYPE: DNA

```
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 32
cacctccaca gtacatccac c                                              21

<210> SEQ ID NO 33
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 33
tgatagggat ctagtgctga agg                                            23

<210> SEQ ID NO 34
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 34
tcattgtgga agttttcgag ca                                             22

<210> SEQ ID NO 35
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 35
tgcggtaacc agacagatac a                                              21

<210> SEQ ID NO 36
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 36
tagccgctca ttccgatcac                                                20

<210> SEQ ID NO 37
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 37
gggatgccat tcccgcttt                                                 19
```

```
<210> SEQ ID NO 38
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 38
tcacgtcatg tacgacatcc c                                              21

<210> SEQ ID NO 39
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 39
gtggcagctt gagggctaag                                                20

<210> SEQ ID NO 40
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 40
gcuuutttgt catcgcuucc                                                20

<210> SEQ ID NO 41
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 41
uugauattat cctttgagcc                                                20

<210> SEQ ID NO 42
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"
```

```
<400> SEQUENCE: 42
ggugatattg tccagggacc                                              20

<210> SEQ ID NO 43
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 43
ccgttttctt accaccct                                                18

<210> SEQ ID NO 44
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 44
ccguuttctt accacccu                                                18
```